(12) United States Patent
Clemens et al.

(10) Patent No.: US 11,505,784 B2
(45) Date of Patent: Nov. 22, 2022

(54) CELL CULTURE MEDIUM

(71) Applicant: BOEHRINGER INGELHEIM INTERNATIONAL GMBH, Ingelheim am Rhein (DE)

(72) Inventors: Christoph Clemens, Biberach an der Riss (DE); Jochen Schaub, Schemmerhofen (DE); Marie Link, Biberach an der Riss (DE); Peter Schorn, Langenau (DE); Torsten Schulz, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 341 days.

(21) Appl. No.: 15/562,288

(22) PCT Filed: Mar. 31, 2016

(86) PCT No.: PCT/EP2016/057036
§ 371 (c)(1),
(2) Date: Sep. 27, 2017

(87) PCT Pub. No.: WO2016/156476
PCT Pub. Date: Oct. 6, 2016

(65) Prior Publication Data
US 2018/0346881 A1   Dec. 6, 2018

(30) Foreign Application Priority Data

Apr. 1, 2015  (EP) ................................ 15162228

(51) Int. Cl.
*C12N 5/071*  (2010.01)
*C07K 16/28*  (2006.01)
*C12N 5/00*  (2006.01)

(52) U.S. Cl.
CPC ........ *C12N 5/0682* (2013.01); *C07K 16/2887* (2013.01); *C12N 5/0031* (2013.01); *C07K 2317/24* (2013.01); *C12N 2500/02* (2013.01); *C12N 2500/24* (2013.01); *C12N 2500/32* (2013.01); *C12N 2500/46* (2013.01); *C12N 2511/00* (2013.01)

(58) Field of Classification Search
CPC .............. C12N 5/0682; C12N 2500/46; C12N 2500/32; C12N 2511/00; C12N 5/0037
See application file for complete search history.

(56) References Cited

U.S. PATENT DOCUMENTS

| 3,809,733 A | 5/1974 | Sandiford et al. |
| 4,657,866 A | 4/1987 | Kumar |
| 5,871,999 A * | 2/1999 | Boraston ............... C12N 5/00 435/240.25 |
| 6,048,728 A * | 4/2000 | Inlow ................. C12N 5/0037 435/325 |
| 2006/0121569 A1* | 6/2006 | Drapeau et al. ......... C12N 5/06 435/69.1 |
| 2011/0229933 A1 | 9/2011 | Krishnan et al. |
| 2012/0309056 A1* | 12/2012 | Leon ................... A61K 39/145 435/69.6 |
| 2016/0264940 A1* | 9/2016 | Broly .................. C12N 5/0682 |

FOREIGN PATENT DOCUMENTS

| WO | 9845411 A1 | 10/1998 |
| WO | 2008090290 A2 | 7/2008 |
| WO | 2009014272 A1 | 1/2009 |
| WO | 2010036767 A1 | 4/2010 |
| WO | 2011134921 A1 | 11/2011 |
| WO | 2014110433 A1 | 7/2014 |

OTHER PUBLICATIONS

Ghaffari, Navid, "Effect of amino acid limitation and supplementation in Chinese hamster ovary fed-batch cultures", https://open.library.ubc.ca/clRcle/collections/ubctheses/24/items/1.0167128 , Fenruary 2015, pp. i-xviii, 1-133. (Year: 2015).*
Sanders et al., "Influence of Amino Acids on Growth of Datura Embryos in Culture", Proc. N. A. S., 1948, pp. 516-526 (Year: 1948).*
International Search Report PCT/EP2016/057036 dated Jun. 30, 2016, 7 pgs.
Ill, Charles R. et al. "Species Specificity of Iron Delivery in Hybridomas" (1998) In Vitro Cellular & Developmental Biology, vol. 24, No. 5, 413-419.
Keenan, J. et al. "Letter to the Editor: Replacement of Transferrin By Simple Iron Compounds for MDCK Cells Grown and Subcultured in Serum-Free Medium" In Vitro Cell. Dev. Biol.(1996) Animal, vol. 32 451-453.
Kishishita et al., "Optimization of Chemically Defined Feed Media for Monoclonal Antibody Production in Chinese Hamster Ovary Cells", Journal of Bioscience and Bioengineering, vol. 120, Issue 1, Jul. 2015, pp. 78-84.

* cited by examiner

*Primary Examiner* — Kara D Johnson
(74) *Attorney, Agent, or Firm* — Shelley A. Jones

(57) ABSTRACT

The present invention provides a basal cell culture medium and a feed medium with novel amino acid ratios and/or iron choline citrate as iron carrier that result in improved performance of mammalian cell culture processes, such as CHO cultivation and protein production processes, in particular in increased product titer (e.g. of monoclonal antibodies). Also provided are methods for culturing mammalian cells and producing a protein of interest using said basal cell culture medium and optionally feed medium. The invention also provides for a medium platform that comprises (i) the basal cell culture medium and (ii) the feed medium.

7 Claims, 21 Drawing Sheets
Specification includes a Sequence Listing.

(E) Product Conc. [mg/L]

(F) Product Conc. [mg/L]

(G) Product Conc. [mg/L]

(A) Viable Cell Conc. [e$^5$ c/mL]

Time [day]

(B) Viability [%]

Time [day]

(C) Product Conc. [mg/L]

Time [day]

(K) Viable Cell Conc. [e$^5$ c/mL]

Time [day]

(L) Viability [%]

Time [day]

(M) Product Conc. [mg/L]

Time [day]

(D) Viable Cell Conc. [e⁵ c/mL]

(E) Viability [%]

(F) Product Conc. [mg/L]

(G) Viable Cell Conc. [e$^5$ c/mL]

(H) Viability [%]

(I) Product Conc. [mg/L]

(A) Viable Cell Conc. [e⁵ c/mL]

Time [day]

(B) Viability [%]

Time [day]

(C) Product Conc. [mg/L]

Time [day]

(D) Product Conc. [mg/L]

Time [day]

(A) Viable Cell Conc. [e$^5$ c/mL]

(B) Product Conc. [mg/L]

(C) Product Conc. [mg/L]

(D) Product Conc. [mg/L]

(A) Product Conc. [mg/L]

(B) Product Conc. [mg/L]

(C) Product Conc. [mg/L]

(D) Product Conc. [mg/L]

(A) Viable Cell Conc. [e$^5$ c/mL]

(B) Viability [%]

(C) Product Conc. [mg/L]

(D) Product Conc. [mg/L]

(A) Viable Cell Conc. [e⁶ c/mL]

(B) Viability [%]

(C) Product Conc. [mg/L]

CELL CULTURE MEDIUM

BACKGROUND OF THE INVENTION

Technical Field

The invention concerns the field of cell culture and recombinant protein production in mammalian cells. It specifically concerns a novel basal cell culture medium as well as a novel feed medium for optimal production (e.g. titer) and performance (e.g. cell growth) in mammalian cell culture for products such as (poly)peptides, antibodies, antibody fragments and antibody derived molecules using recombinant mammalian host cells.

BACKGROUND

The development of mammalian cell culture processes for large-scale industrial manufacturing of therapeutic proteins (e.g. monoclonal antibodies) began about 25 years ago. An efficient bioprocess for the production of biopharmaceuticals mainly requires (i) a high-producing, stable and regulatory-accepted (typically mammalian) cell line, (ii) optimal cell culture media to support cell growth and production in different (typically mammalian) host cells and in different cultivation systems and process modes (for example at different scales and as e.g. batch, fed batch and perfusion processes), and (iii) an optimal technical bioprocess, characterized by e.g. optimal supply of oxygen by an adequate configuration of stirrers and gas supply, automated control of all relevant process parameters to ensure consistent product quality, or process designs that can be scaled-up from small-scale process development (mL- to L-scale) to large-scale manufacturing (>2.000 L) without compromising performance and product quality.

In this context, cell culture media have a key role and have to fulfill the complex nutritional requirements of mammalian cells cultivated in suspension in technical systems in contrast to their natural origin. For example, the most widely used cell line for biopharmaceutical production was originally derived from the Chinese hamster ovary (CHO cell).

In the past, serum was used as medium additive to provide nutrients or carrier proteins that are typically not present in cell culture media, e.g. cholesterol and transferrin or factors for cell-substrate attachment (for example fibronectin), other hormones and growth factors, but also a protection of certain essential nutrients and binding of toxic components within the culture medium. However, in cell culture media used for production of therapeutics, serum can potentially introduce animal viruses and it may introduce other undesirable contaminants into cell culture processes (for example antibiotics or proteases) due to the undefined origin of the raw material. These compounds were successfully replaced and serum-free cell culture media have become industrial practice for process development and recombinant production of biopharmaceuticals. For example, CHO (Chinese hamster ovary) cells were serially propagated in serum-free medium containing human insulin as the only medium protein component (Keen and Rapson, Cytotechnology, October 17(3): 153-63, 1995).

Another group of media components that is commonly used in biopharmaceutical production are hydrolysates, either derived from animal origin or derived from plants. Due to the associated safety risk, hydrolysates from animal origin are removed from the process whenever possible. Hydrolysates usually contain a mixture of amino acids, small peptides, inorganic ions, trace elements, carbohydrates and vitamins and are widely used to enrich the culture medium with a variety of (essential) nutrients to increase overall growth and productivity. Another disadvantage, besides safety aspects, is the fact that hydrolysates are not chemically defined, thus the exact composition between lots can change (lot-to-lot variability) and, for that reason, have a negative impact on process reproducibility. Since hydrolysates contain many compounds and have a complex (in every detail unknown) composition they cannot easily be replaced without effecting cell culture performance (e.g. product yields). It is a persisting and unsolved challenge for bioprocess development to screen and subsequently replace such undefined raw materials with chemical-defined components and maintaining consistent product quality and high product titers at the same time. Not only the exact chemical composition needs to be determined, but also the exact concentrations of every component. Due to safety aspects, today, mainly hydrolysates from plant origin are used (e.g. soy bean hydrolysates). However, the problem of undefined composition remains.

Currently biopharmaceutical process development aims for chemically defined media (serum-free, animal component-free, chemically defined). This leads to a further reduced risk of contaminants (e.g. reduction of organic materials, endotoxins, unknown metals and trace elements derived from unknown nutrient sources) and also fosters an increased control over all aspects of upstream and downstream processing with respect to consistent raw materials without any risks related to safety and lot-to-lot variability. Only recently, "chemically defined" (note that there is no industry standard that clearly defines this term yet) media became commercially available for mammalian cell culture but application in industrial manufacturing currently still is limited.

The exact composition of such "chemically defined" hydrolysates or media supplements are known (but typically only to the media supplier) so that no undefined raw materials are in use. These chemically defined media are still complex and contain up to about 40-50 "key components". But they are made up of different building blocks. To design such complex "chemically defined" media it is necessary to mimic plant or animal derived hydrolysates as close as possible which requires extensive fractionation of those hydrolysates followed by high-end analytics. A major challenge in this field is given by the tremendous diversity of compounds present in cell culture media.

Optimal design of high-performance cell culture media is further complicated by the fact that many processes are performed in the so-called fed batch mode, i.e., a cell culture is inoculated in a basal start medium and then (typically after about 0 to 3 days) a concentrated feed medium is supplied to sustain growth and production when media substrates get depleted due to cell growth. Providing all media compounds from the beginning (batch mode) results in suboptimal process performance since then cells are overfed in the beginning (for example resulting in high formation of the unwanted by-product lactate which in turn has an adverse effect on cell growth and viability). The major challenge in this context is to design an optimal batch medium (basal cell culture medium) and an optimal fed batch medium (feed medium) that perfectly match for optimal growth and production in a cell culture process throughout the cultivation run time. Since viable cell concentration, viability of the cell culture and nutritional requirements of a cell culture process significantly change over the time course of a cultivation process (on an hourly to daily basis), the design of optimal batch and fed batch media (basal cell culture medium and feed medium) is a demanding task. It is even more difficult since typically one feed medium is designed that provides the optimal solution for every single hour and every single day of a fermentation process which lasts in total up to about 2-3 weeks.

The state of the art in industrial mammalian cell culture medium design using a "rational" approach has been summarized by Fletcher (Fletcher T., BioProcess International 3(1), 30-36, 2005), and this approach can still be considered as the state of the art concept for rational media design in industrial practice. It is pointed out that the complexity of rational medium design is not only given by the fact that many components are involved but also that the specific concentrations and the complex interactions of media compounds need to be considered.

According to Fletcher three basic approaches exist in medium design. These are i) (single) component titration (experiments to define a dose response e.g. on titer), ii) media blending (simply blend existing (complex) media and identify the best blend), iii) spent media analysis (describe nutrient depletion by chemical analysis of spent medium vs. fresh medium; note that specific metabolic needs on a cell basis are not considered in this approach), iv) automated screening (robotic fluid handling with strong focus on throughput e.g. in multi-well plates). None of these methods is best in every way, and each has its own particular weaknesses according to Fletcher. For example, i) component titration causes immense amounts of samples to be analyzed which is not feasible in industrial practice for many reasons (e.g. capacity, costs, resources), ii) media blending leads to improved throughput but this approach is poorly instructive and very limited in scope, iii) spent media analysis can provide important information how culture chemistry changes over time, but it cannot provide a complete picture of the cell culture requirements based on the fact that typically spent media analysis focuses only on a quite limited number of components (note that, for example, a complete amino acid analysis of all 20 amino acids is typically not performed and only the two most important amino acids glutamine and glutamate are routinely measured), iv) automated screening increases throughput by minimizing the cultivation system but, in turn, has adverse effects on (correctly) modeling a large-scale process since such miniaturized systems fail to correctly predict cell culture performance in the large-scale. Hence, Fletcher concluded that real rational media design can be described as multidimensional approach. Instead of relying on a single technique, rational media design makes use of several complementary methods, namely DoE (Design of experiments) and full factorial designs that capture the complex interactions of multiple components and use various statistical tools. Although this concept integrates previous media design concepts and applies advanced DoE approaches for optimal design of experiments, it clearly lacks the cell-specific requirements, i.e. the cellular perspective of nutritional supply and cellular metabolism. Hence, there is still a need for improved cell culture media.

Cell Culture Media:

In mammalian cell cultivation, cell culture media can comprise up to about 100 compounds and more. For example, carbohydrates (e.g. for generation of energy by catabolic reactions or as building blocks by anaplerotic reactions), amino acids (e.g. building blocks for cellular protein and product in case of therapeutic protein production), lipids and/or fatty acids (e.g. for cellular membrane synthesis), DNA and RNA (e.g. for growth and cellular mitosis and meiosis), vitamins (e.g. as co-factors for enzymatic reactions), trace elements, different salts, growth factors, carriers and transporters etc. These components or compound groups are required to fulfill the complex nutritional requirements of mammalian cells in a technical cultivation environment. There exist classical cell culture media such as DMEM (Dulbecco's Modified Eagle's Medium) where all components and all concentrations are published. Development of such cell culture media go back to the late 1950s and are comprehensively described in the academic literature. Another example is Ham's F12 (Ham's Nutrient Mixture F12) that was developed in the 1970s, or mixtures/modifications of such classical cell culture such as DMEM:F12 (Dulbecco's Modified Eagle's Medium/Ham's Nutrient Mixture F12) that were developed in the 1970s and 1980s. Another widely used cell culture medium with known composition and concentrations is RPMI. RPMI was developed in the 1970s by Moore et al. at the Roswell Park Memorial Institute (hence the acronym RPMI). Different variants are used in animal cell culture, for example RPMI-1640. Although many of these classical media were developed decades ago, these formulations still form the basis for much of the cell culture research occurring today and represent state of the art in animal cell culture for media with completely known composition and completely known concentrations for each compound. All of these media are commercially available and can be obtained from suppliers (e.g. from Sigma-Aldrich). Due to the increasing business in biopharmaceuticals, commercial media suppliers developed own cell culture media for use in mammalian cell culture over the past years.

However, in contrast to classical cell culture media, the exact formulations of such commercial cell culture media are proprietary to the vendors. For this reason, such commercial media cannot be used as a reference and starting point for rational media design since the exact formulation is not known (even for the major compounds such as amino acids). For example, the commercially available medium ActiCHO (by PAA) consisting of a basal medium (ActiCHO P) and a feed medium (ActiCHO Feed A+B) is chemically defined according to supplier definition (only single chemicals, free of animal derived substances, growth factors, peptides, and peptones). But the exact formulation is proprietary. The two feeds consist of concentrated amino acids, vitamins, salts trace elements and carbon source (Feed A) and selected amino acids in concentrated form (Feed B). Another example is Ex-Cell CD CHO (SAFC Biosciences). This medium is animal component free, chemically defined according to SAFC, serum-free, and formulation is also proprietary. A third example medium that is widely used in mammalian cell culture using CHO is CD CHO (Life technologies). This medium is protein free, serum-free, and chemically defined according to Life technologies. It does not contain proteins/peptides of animal, plant or synthetic origin or undefined lysates/hydrolysates. Again formulation is proprietary. This CD CHO basal medium can be combined with feed media named Efficient Feed A, B, and C. Also for the feeds the formulation is proprietary. The feeds are animal origin-free and the components are contained in higher concentrations. The feeds are chemically defined. No proteins, no lipids, no growth factors, no hydrolysates and no components of unknown composition are used. It contains a carbon source, concentrated amino acids, vitamins and trace elements. Another feed that is commercially available can be obtained by Thermo Fisher, named Cell Boost 1-6. Again, the formulation is proprietary. It is chemically defined according to Thermo Fisher, protein free, and animal derived components free. Cell Boost 1 and 2 contain amino acids, vitamins, and glucose. Cell Boost 3 contains amino acids, vitamins, glucose, and trace elements. Cell Boost 4 contains amino acids, vitamins, glucose, trace elements, and growth factors. And Cell Boost 5 and 6 contain amino acids, vitamins, glucose, trace elements, growth factors, lipids, and cholesterol.

Amino Acids

Amino acids have an essential role for protein synthesis, both for cellular protein and for the production of the product in case of recombinant proteins or protein derived substances. For examples, proteins are synthesized by the cellular machinery from single amino acids molecules to form larger proteins or protein complexes. In mammalian cell cultivation the essential amino acids need to be provided with the cell culture medium, since mammalian cells are not able to synthesize essential amino acids from other precursors and building blocks. Amino acids are also biochemically important because these molecules have two functional groups (amino group and an acidic group) which enables them to interact with other biological molecules. For these reasons cell culture media containing amino acids are often also supplemented with a variety of (defined and undefined) small peptides, hydrolysates, proteins and protein mixtures from different origins (animal derived, plant derived or chemically defined).

In the context of the present invention it was found that specific amino acid compositions and novel amino acid ratios both in the (basal) cell culture medium and in the feed medium significantly increase final product titers. This new amino acid composition and amino acid ratios significantly differ from the state of the art of commercially available cell culture media (e.g. RPMI, DMEM:F12 1:1) and provide higher product titers.

Iron and Iron Carrier

Iron is an essential ingredient in mammalian cell culture media (i) as a trace element and (ii) as a transferrin replacement (e.g. iron as iron chelators). Transferrin is typically derived from plasma. This compound is typically supplied as a lyophilized powder of human transferrin which is partially iron-saturated. Transferrin is a glycoprotein with homologous N-terminal and C-terminal iron-binding domains and is related to several other iron-binding proteins including lactoferrin, melanotransferrin, and ovotransferrin. Transferrin is commercially available for use in animal cell culture (e.g. by Sigma-Aldrich, CAS number 11096-37-0). There exist several other iron compounds that are used as transferrin replacement. These exist in II/III forms, as various salts, as hydrated/dehydrated forms. Examples are iron (III) phosphate, iron (III) pyrophosphate, iron (III) nitrate, iron (II) sulfate, iron (III) chloride, iron (II) lactate, ferric (III) citrate, ammonium ferric (III) citrate, iron-dextran, or ethylenediaminetetraacetic acid ferric sodium salt.

We identified iron choline citrate (iron/ferric choline citrate, CAS-Number 1336-80-7, molecular weight Mw=991.5 g/mol+/−49.57 g/mol due to 5% crystal water content, iron complex with iron content of about 10.2-12.4%, molecule ratio for iron:choline:citrate of 2:3:3, molecule formula $C_{33}H_{57}Fe_2N_3O_{24}$). However, other suitable iron choline citrate complexes are known such as iron:choline:citrate at a ratio of 1:1:1, molecular weight of Mw=348.11 g/mol. Compared to state of the art iron sources used in commercially available cell culture media such as iron phosphate, iron pyrophosphate or iron citrate, the usage of iron choline citrate contributes to significantly higher product titers. This effect also depends on the iron choline citrate concentration in the media.

SUMMARY OF THE INVENTION

The present invention provides a basal cell culture medium and a feed medium with novel amino acid ratios and/or iron choline citrate as iron carrier that improve the performance of mammalian cell culture processes, such as CHO cultivation and protein production processes, in particular product titers (e.g., monoclonal antibody (mAb) titres). Also provided are methods for culturing mammalian cells and producing a protein of interest using said basal cell culture medium and/or feed medium. The invention also provides for a medium platform that comprises (i) the basal cell culture medium and (ii) the feed medium. Preferably, both the (basal) cell culture medium and the feed medium are chemically defined.

In one aspect the invention relates to a basal cell culture medium for culturing mammalian cells comprising the following amino acids at a molar ratio relative to isoleucine (mM/mM) of: L-leucine/L-isoleucine of about 1.2-2.2, L-phenylalanine/L-isoleucine of about 0.5-0.9, L-tyrosine/L-isoleucine of about 1.5-2.7, L-threonine/I-isoleucine of about 1.0-1.9, and L-valine/L-isoleucine of about 1.0-1.9, wherein the basal cell culture medium has a total amino acid content of about 25 to 150 mM. In one embodiment the basal cell culture medium further comprises L-lysine at a molar ratio relative to isoleucine of about 1.6-2.9 (mM/mM). The basal cell culture medium may further comprise at least one of the following amino acids at a molar ratio relative to isoleucine (mM/mM) of: L-tryptophan/L-isoleucine of about 0.3-0.5, L-proline/L-isoleucine of about 1.6-3.0; or L-methionine/L-isoleucine of about 0.4-0.7. Preferably the basal cell culture medium comprises L-tryptophan, L-proline and L-methionine each at said molar ratios as defined above. The basal cell culture medium of the invention is a serum-free medium, preferably a chemically defined medium or a chemically defined and protein-free medium. In one embodiment the basal cell culture medium additionally comprises iron choline citrate at a concentration of about 0.1 to 5.0 mM, about 0.2 to 2.0 mM, about 0.2 to 1.0 mM or about 0.4 to 1.0 mM. In certain embodiments the basal cell culture medium has a total amino acid content of about 30 to about 130, preferably about 35 to about 120, more preferably about 40 to about 100 mM.

The present invention also relates to a basal cell culture medium for culturing mammalian cells comprising iron choline citrate at a concentration of about 0.1 to 5.0 mM, about 0.2 to 2.0 mM, about 0.2 to 1.0 mM or about 0.4 to 1.0 mM.

In another aspect the present invention relates to a feed medium for culturing mammalian cells comprising the following amino acids at a molar ratio relative to isoleucine (mM/mM) of: L-leucine/L-isoleucine of about 2.3-4.2, L-phenylalanine/L-isoleucine of about 0.6-1.1, L-threonine/I-isoleucine of about 1.3-2.4, and L-valine/L-isoleucine of about 1.1-2.0, wherein the feed medium has a total amino acid content of about 100 to 1000 mM. In one embodiment of the present invention the feed medium further comprises the following amino acids at a molar ratio relative to isoleucine (mM/mM) of: L-tyrosine/L-isoleucine of about 0.6-1.1, and/or L-lysine/L-isoleucine of about 1.1-2.1. The feed medium according to the invention may further comprise at least one of the following amino acids at a molar ratio relative to isoleucine (mM/mM) of: L-tryptophan/L-isoleucine of about 0.3-0.6, L-proline/L-isoleucine of about 0.9-1.8; or L-methionine/L-isoleucine of about 0.4-0.8. Preferably the feed medium comprises L-tryptophan, L-proline and L-methionine each at said molar ratios as defined above. The feed medium is typically a concentrated feed medium. Preferably the feed medium of the invention is a serum-free medium, more preferably a chemically defined medium or a chemically defined and protein-free medium. In one embodiment the feed medium additionally comprises iron choline citrate at a concentration of about 0.4 to 5 mM, about 0.4 to 1.0 mM or about 0.5 to 1.0 mM, preferably about 0.5 to 0.6 mM. In one embodiment the feed medium is characterized by a low salt content, preferably a low salt content of about 100 mM or less and more preferably about 50 mM or less. In certain embodiments the feed medium of the invention has a total amino acid content of about 200 to about 900, preferably about 300 to about 800, more preferably about 400 to about 700 mM.

The present invention also relates to a feed medium for culturing mammalian cells comprising iron choline citrate at a concentration of about 0.4 to 5 mM, about 0.4 to 1.0 mM or about 0.5 to 1.0 mM, preferably about 0.5 to 0.6 mM.

In a related aspect the invention relates to a medium platform for culturing mammalian cells comprising the basal cell culture medium of the invention and the feed medium of the invention as described herein.

The basal cell culture medium and the feed medium of the invention are particularly suitable for culturing rodent or human cells, wherein the rodent cell is preferably a Chinese hamster ovary (CHO) cell such as a CHO-K1 cell, a CHO-DG44 cell, a CHO-DUKX B11 cell or a CHO glutamine synthetase (GS) deficient cell, most preferably the cell is a CHO-DG44 or a CHO GS deficient cell.

In yet another aspect the invention relates to a method of generating a basal cell culture medium comprising: a) providing a basal cell culture medium, and b) adding amino acids at or adjusting the amino acid ratios to the final molar ratio according to the invention. The method may further comprise a step of adding or adjusting as an iron source iron choline citrate at a concentration of about 0.1 to 5.0 mM, about 0.2 to 2.0 mM, about 0.2 to 1.0 mM, or about 0.4 to 1.0 mM.

In yet another aspect the invention relates to a method of generating a feed medium comprising: providing a feed medium, and adding amino acids at or adjusting the amino acid ratios to the final molar ratios according to the invention. The method may further comprise a step of adding or adjusting as an iron source iron choline citrate at a concentration of about 0.4 to 5 mM, about 0.4 to 1.0 mM, or about 0.5 to 1 mM, preferably about 0.5 to 0.6 mM.

The invention further relates to a method of culturing a mammalian cell comprising the following steps: a) providing mammalian cells, b) culturing the cells in the basal cell culture medium of the invention, and c) optionally adding the feed medium of the invention to the basal cell culture medium; wherein the cells are cultured under conditions that allow the cells to proliferate.

The invention also relates to a method of producing a protein of interest comprising the following steps: a) providing mammalian cells comprising a gene of interest encoding the protein of interest, b) culturing the cells in the basal cell culture medium of the invention, and c) optionally adding the feed medium of the invention to the basal cell culture medium, and d) optionally separating and/or isolating and/or purifying said protein of interest from the cell culture; wherein the cells are cultured under conditions that allow expression of the protein of interest. The protein of interest may be a secreted protein, preferably the protein of interest is an antibody or Fc-fusion protein.

The mammalian cell used in any of the methods of the invention may be a rodent or human cell, preferably the rodent cell is a Chinese hamster ovary (CHO) cell such as a CHO-K1 cell, a CHO-DG44 cell, a DuxB11 cell or a CHO GS deficient cell, most preferably the cell is a CHO-DG44 or a CHO GS deficient cell. The feed medium used in any of the methods of the invention is to be added to the cells cultured in the basal cell culture medium, wherein (a) the feed medium is added at about 10-50 ml/L/day based on the culture starting volume to the basal cell culture medium, (b) the feed medium is added starting on day 0, 1, 2 or 3, and/or (c) the feed medium is added continuously, or as a bolus several times a day, two times a day, once per day, every second day or every third day.

In yet another aspect the invention relates to a kit of parts comprising the basal cell culture medium of the invention and/or the feed medium of the invention, and optionally a mammalian cell.

The invention further relates to a use of the basal cell culture medium of the invention for producing a protein comprising culturing mammalian cells that produce a protein of interest in said medium for a period of time and conditions suitable for cell growth and protein production, harvesting the protein of interest and recovering the protein from the culture medium or cell lysate. The use may further comprise feeding the cells with the feed medium of the invention during said culture period.

The invention also relates to a use of the feed medium of the invention for producing a protein comprising culturing mammalian cells that produce the protein of interest in the basal cell culture medium of the invention for a period of time and conditions suitable for cell growth and protein production, feeding the cells with said feed medium, harvesting the protein of interest and recovering the protein from the culture medium.

Also referred to is a use of iron choline citrate as iron carrier in a mammalian cell culture medium, wherein the iron choline citrate is present in the mammalian cell culture medium at a concentration of about 0.2 to 2.0 mM.

Figure 1:
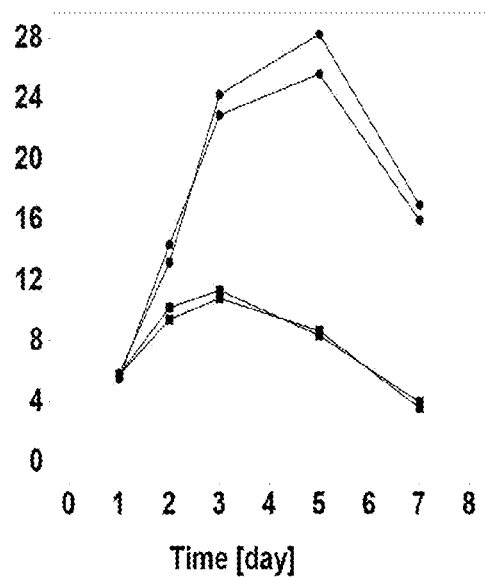
FIG. 1: RPMI based basal medium with and without optimized amino acid adjustment in a batch experiment at different total amino acid concentrations.
Figure 1:
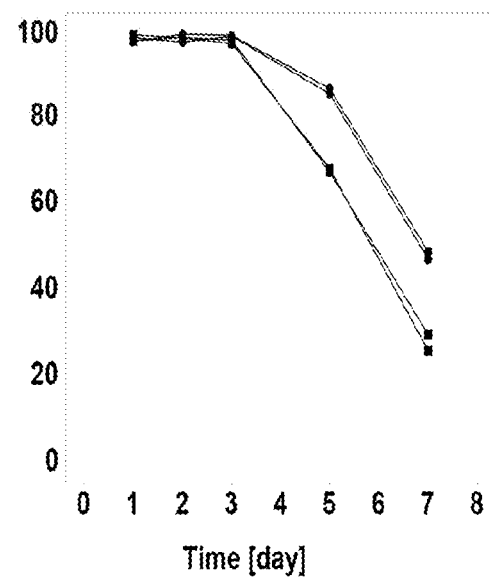
Figure 1:
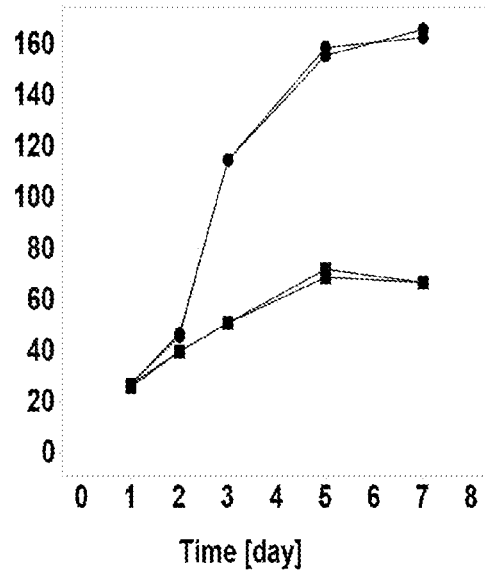
Figure 1:
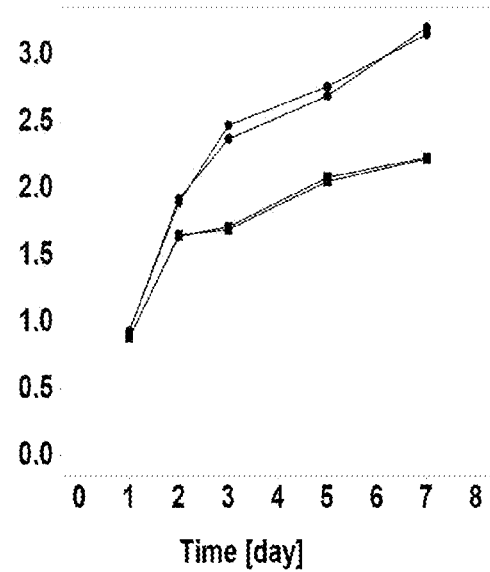
Figure 1:
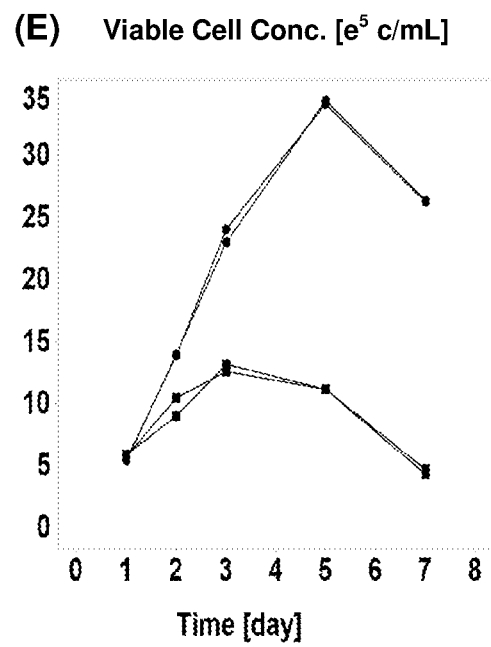
Figure 1:
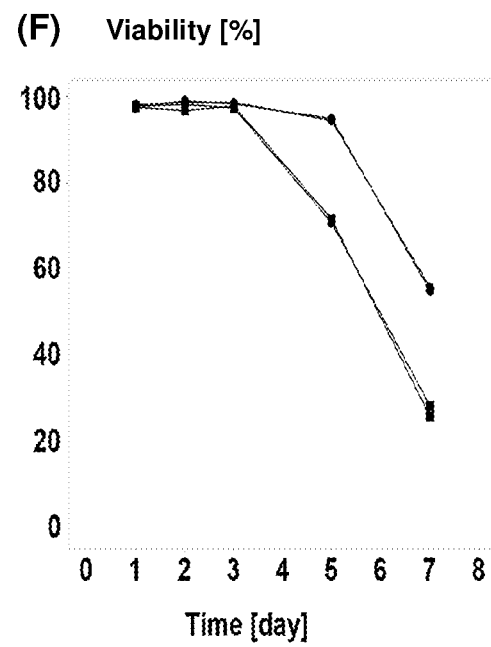
Figure 1:
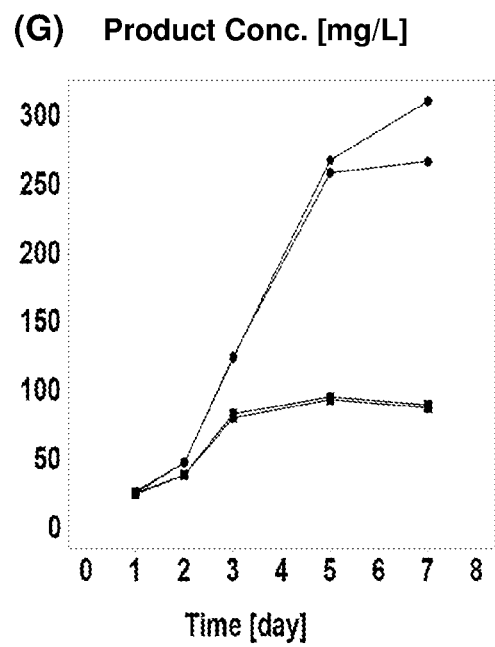
Figure 1:
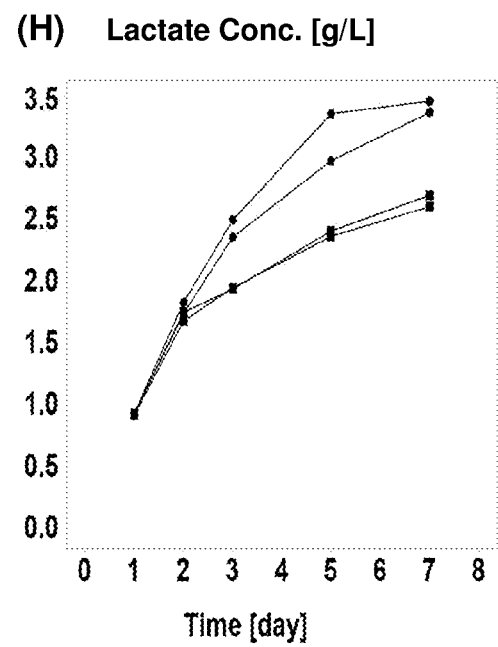
Figure 1:
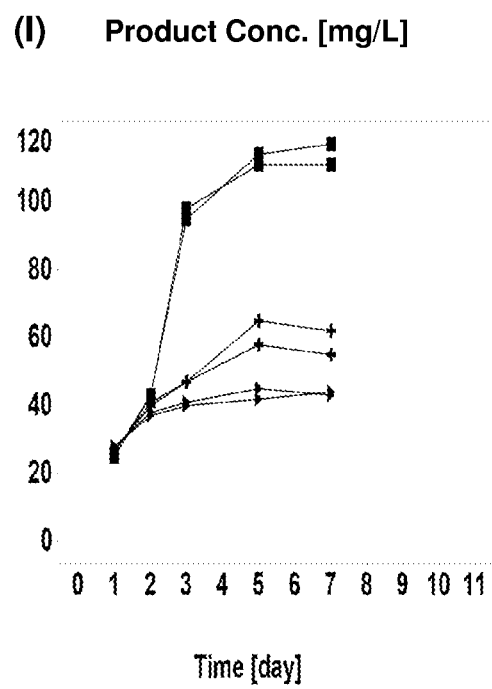
Figure 1:
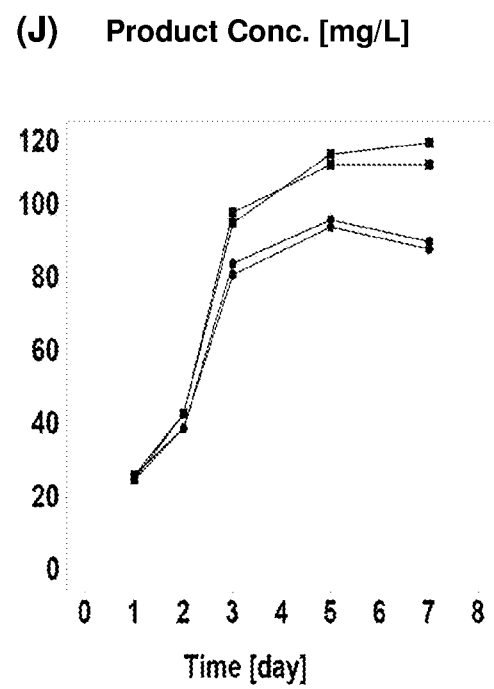

(A-D): CHO2 (CHO-DG44) Rituximab cells were cultured in RPMI based medium 4.1 and medium 5.0 without and with optimized amino acid ratios in duplicates (N=2) with a total amino acid concentration of 44 mM, culture in medium 5.0, with optimized amino acid ratios (44 mM), ■ culture in medium 4.1, without optimized amino acid ratios (44 mM). Shown are (A) viable cell concentration [$1 \times 10^5$ cell/mL] CHO2 (CHO-DG44) Rituximab cells, (B) viability [%] CHO2 (CHO-DG44) Rituximab cells and (C) product concentration [mg/L] CHO2 (CHO-DG44) Rituximab, (D) Lactate concentration [g/L] CHO2 (CHO-DG44) Rituximab.

(E-H): CHO2 (CHO-DG44) Rituximab cells were cultured in RPMI based medium 4.2 and medium 5.1 without and with optimized amino acid ratios in duplicates (N=2) with a total amino acid concentration of 66 mM, ● culture in medium 5.1, with optimized amino acid ratios (66 mM), ■ culture in medium 4.2, without optimized amino acid ratios (66 mM). Shown are (E) viable cell concentration [$1 \times 10^5$ cell/mL] CHO2 (CHO-DG44) Rituximab cells, (F)

viability [%] CHO2 (CHO-DG44) Rituximab cells and (G) product concentration [mg/L] CHO2 (CHO-DG44) Rituximab, (H) Lactate concentration [g/L] CHO2 (CHO-DG44) Rituximab.

(I): CHO2 (CHO-DG44) Rituximab cells were cultured in RPMI based medium 4.3 and medium 5.2 without and with optimized amino acid ratios in duplicates (N=2) with a total amino acid concentration of 22 or 36 mM, ■ culture in medium 5.2, with optimized amino acid ratios (22 mM), ▶ culture in medium 4.3, without optimized amino acid ratios (22 mM), ✦ culture in medium 4.0, without optimized amino acid ratios (36 mM). Shown is (I) product concentration [mg/L] CHO2 (CHO-DG44) Rituximab.

(J): CHO2 (CHO-DG44) Rituximab cells were cultured in RPMI based medium 4.2 and medium 5.2 without and with optimized amino acid ratios in duplicates (N=2) with a total amino acid concentration of 22 and 66 mM, ■ culture in medium 5.2, with optimized amino acid ratios (22 mM), ● culture in medium 4.2, without optimized amino acid ratios (66 mM). Shown is (J) product concentration [mg/L] CHO2 (CHO-DG44) Rituximab.

Figure 2:
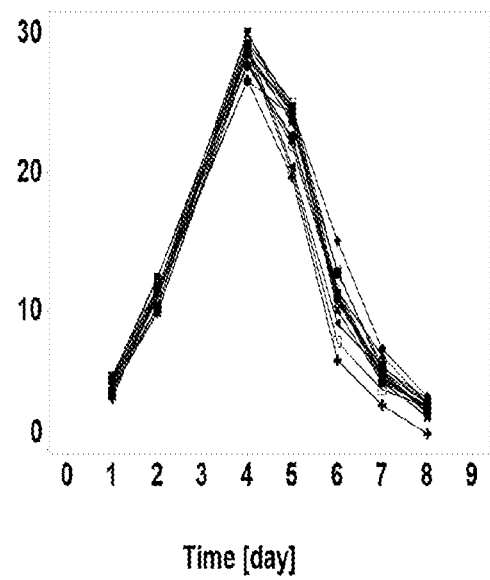
Figure 2:
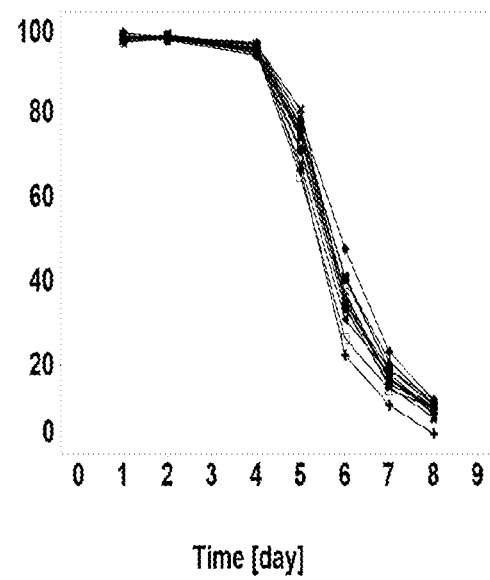
Figure 2:
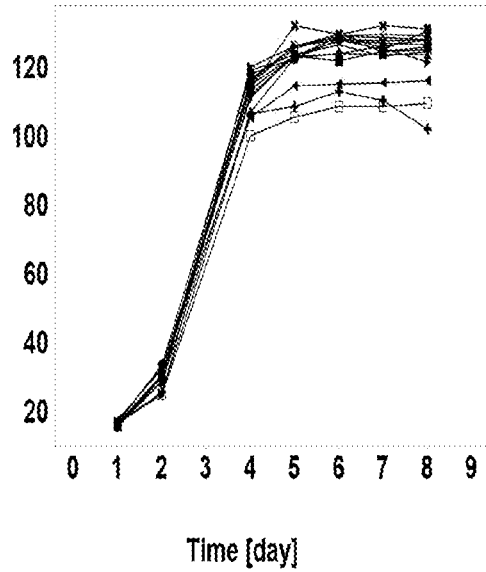
Figure 2:
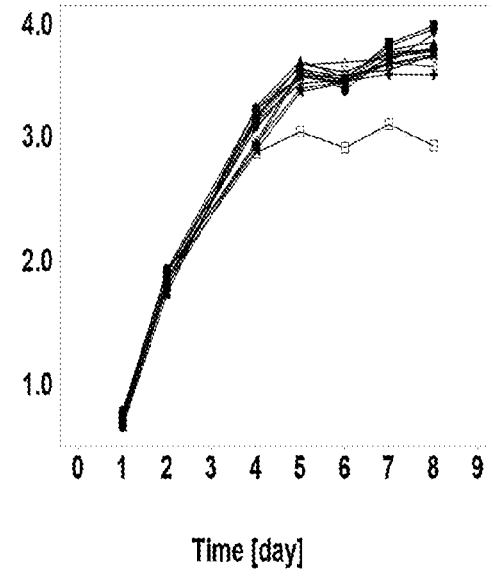
Figure 2:
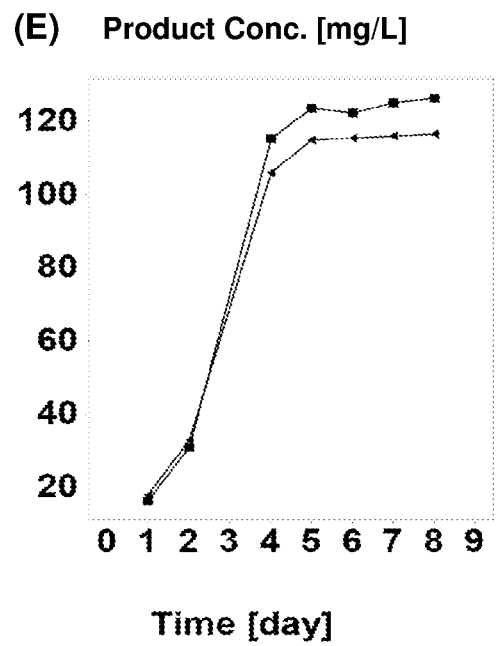
Figure 2:
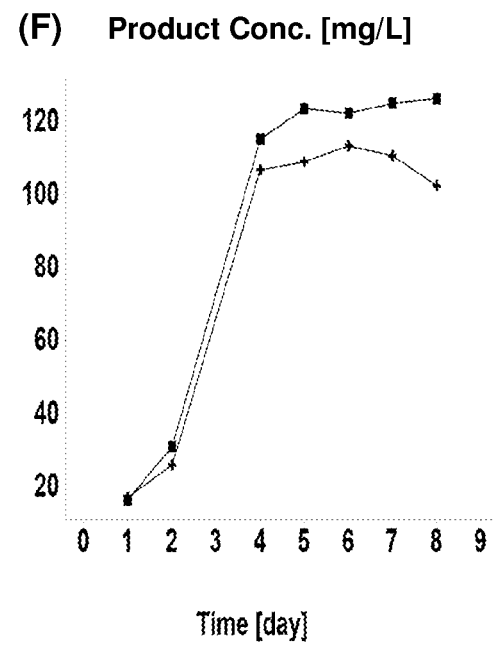
Figure 2:
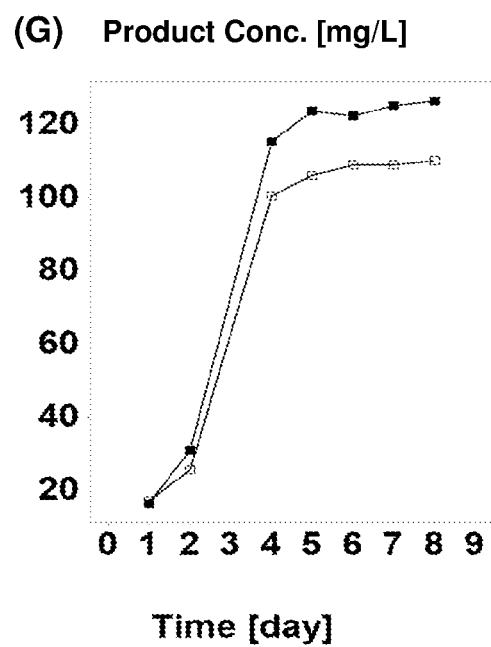
Figure 2:
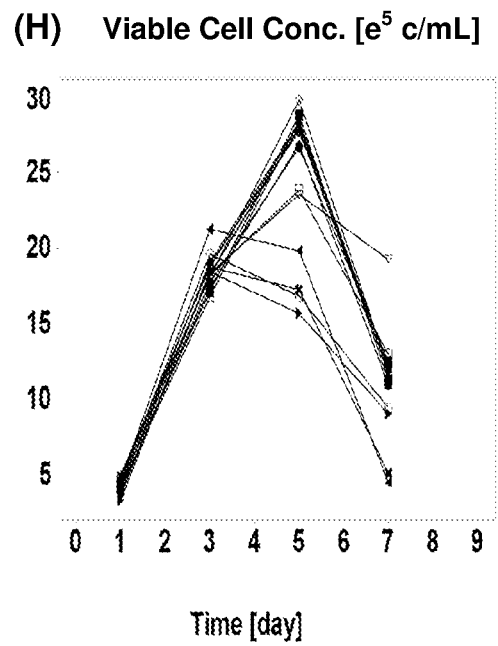
Figure 2:
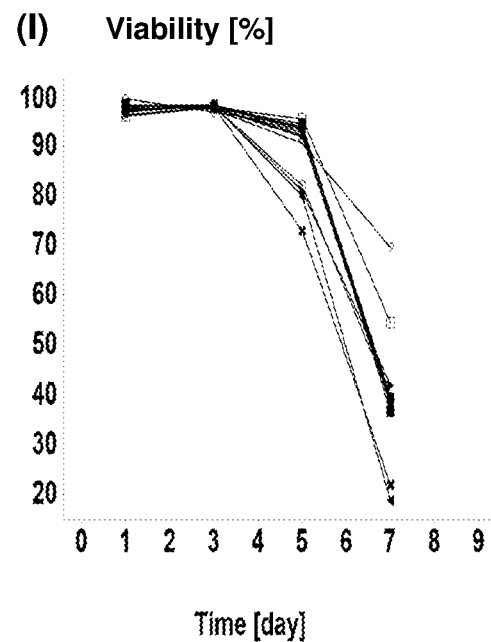
Figure 2:
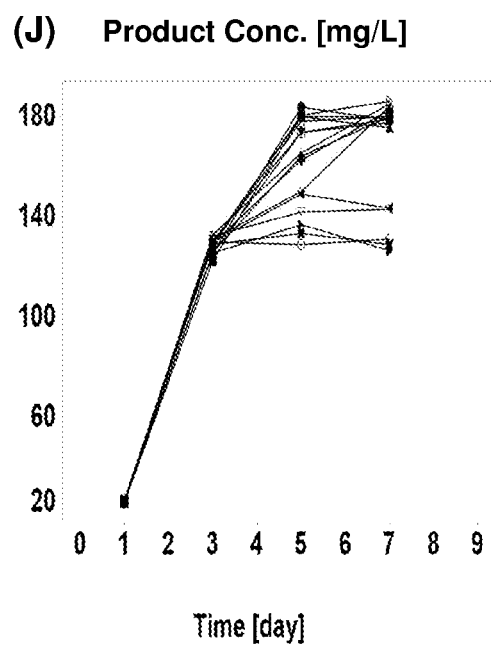
Figure 2:
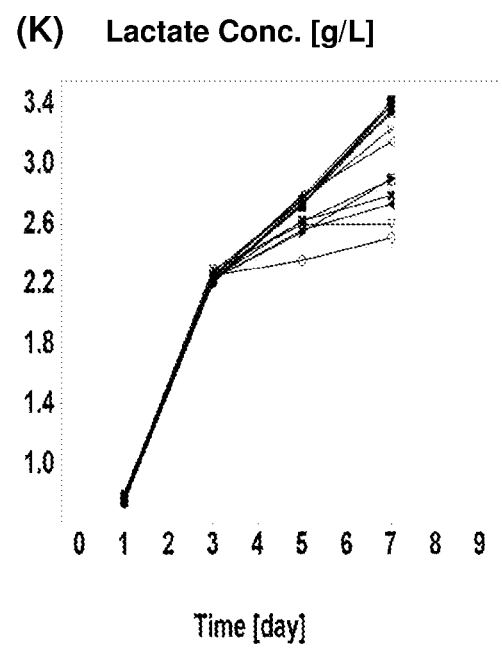
Figure 2:
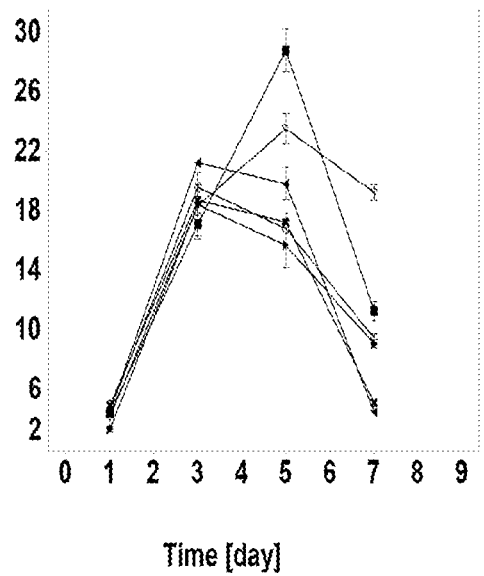
Figure 2:
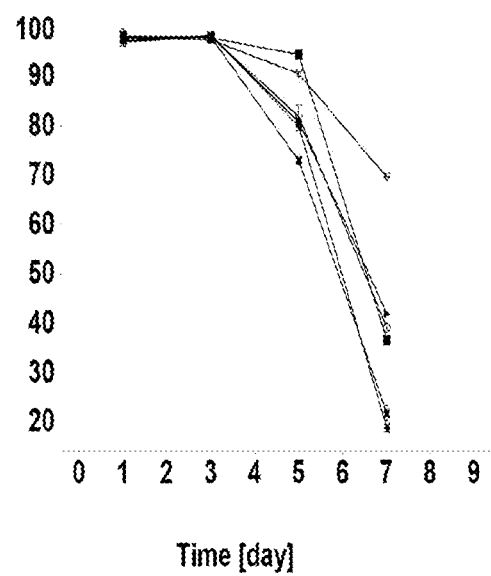
Figure 2:
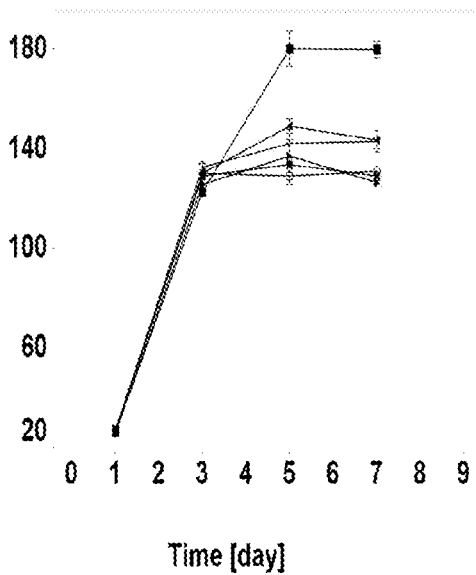
Figure 2:
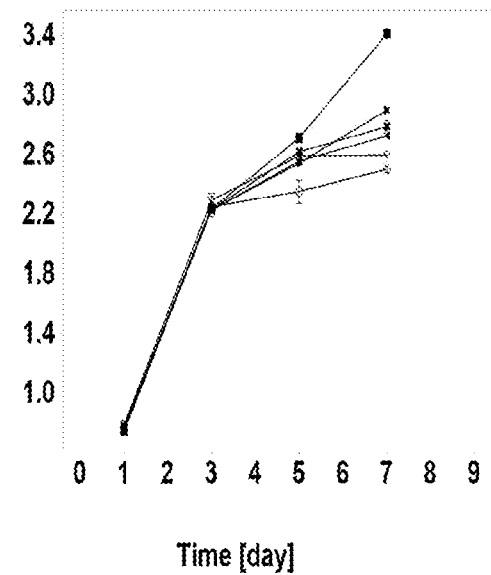

FIG. 2: RPMI based basal medium with a variation of single amino acids by −20% or −40% based on optimized amino acid ratios in a batch experiment.

(A-D): CHO2 (CHO-DG44) Rituximab cells were cultured in RPMI based medium 5.3 (with all amino acids at optimized ratios, control) and medium 5.3.1 (only a single amino acid is modified by −20%), ◀ culture in medium 5.3.1 (L-leucine −20%), + culture in medium 5.3.1 (L-valine −20%), ☐ culture in medium 5.3.1 (L-phenylalanine −20%), ■ culture in medium 5.3 (with all amino acids, control), ● culture in medium 5.3.1 (L-arginine −20%), ◆ culture in medium 5.3.1 (L-asparagine −20%), ▲ culture in medium 5.3.1 (L-aspartic acid −20%), ▼ culture in medium 5.3.1 (L-histidine −20%), ▶ culture in medium 5.3.1 (L-lysine −20%), ✱ culture in medium 5.3.1 (L-methionine −20%), ○ culture in medium 5.3.1 (L-proline −20%), ◇ culture in medium 5.3.1 (L-serine −20%), Δ culture in medium 5.3.1 (L-threonine −20%), ∇ culture in medium 5.3.1 (L-tryptophan −20%), (triangle left, empty) culture in medium 5.3.1 (L-tyrosine −20%). Shown are (A) viable cell concentration [1×10$^5$ cell/mL] CHO2 (CHO-DG44) Rituximab cells, (B) viability [%] CHO2 (CHO-DG44) Rituximab cells, (C) product concentration [mg/L] CHO2 (CHO-DG44) Rituximab, (D) lactate concentration [mg/L] CHO2 (CHO-DG44) Rituximab, controls were performed in triplicate (N=3) and test runs in duplicates (N=2).

(E-G): CHO2 (CHO-DG44) Rituximab cells were cultured in RPMI based medium 5.3 (with all amino acids at optimized ratios, control) and medium 5.3.1 (only a single amino acid, e.g., L-leucine, L-valine or L-phenylalanine, is modified by −20%), ■ culture in medium 5.3 (with all amino acids, control), ☐ culture in medium 5.3.1 (L-phenylalanine −20%), ◀ culture in medium 5.3.1 (L-leucine −20%), + culture in medium 5.3.1 (L-valine by −20%), shown are (E-G) product concentration [mg/L] CHO2 (CHO-DG44) Rituximab, controls were performed in triplicate (N=3) and test runs in duplicates (N=2).

(H-K): CHO2 (CHO-DG44) Rituximab cells were cultured in RPMI based medium 5.3 (with all amino acids at optimized ratios, control) and medium 5.3.1 (only a single amino acid, e.g., L-arginine, L-asparagine, L-aspartic acid, L-histidine, L-isoleucine, L-leucine, L-lysine, L-methionine, L-phenylalanine, L-proline, L-serine, L-threonine, L-tryptophan, L-tyrosine or L-valine, is reduced by −40%), ■ culture in medium 5.3 (with all amino acids, control), ● culture in medium 5.3.1 (L-arginine −40%), ◆ culture in medium 5.3.1 (L-asparagine −40%), ▲ culture in medium 5.3.1 (L-aspartic acid −40%), ▼ culture in medium 5.3.1 (L-histidine −40%), ◀ culture in medium 5.3.1 (L-isoleucine −40%), ▶ culture in medium 5.3.1 (L-leucine −40%), + culture in medium 5.3.1 (L-lysine −40%), ☐ culture in medium 5.3.1 (L-methionine −40%), ○ culture in medium 5.3.1 (L-phenylalanine −40%), ◇ culture in medium 5.3.1 (L-proline −40%), Δ culture in medium 5.3.1 (L-serine −40%), ∇ culture in medium 5.3.1 (L-threonine −40%), (triangle left, empty) culture in medium 5.3.1 (L-tryptophan −40%), (triangle right, empty) culture in medium 5.3.1 (L-tyrosine −40%), × culture in medium 5.3.1 (L-valine −40%), shown are (H) viable cell concentration [1×10$^5$ cell/mL] CHO2 (CHO-DG44) Rituximab cells, (I) viability [%] CHO2 (CHO-DG44) Rituximab cells, (J) product concentration [mg/L] CHO2 (CHO-DG44) Rituximab, (K) lactate concentration [mg/L] CHO2 (CHO-DG44) Rituximab, controls were performed in triplicate (N=3) and test runs in duplicates (N=2).

(L-O): CHO2 (CHO-DG44) Rituximab cells were cultured in RPMI based medium 5.3 (with all amino acids at optimized ratios, control) and medium 5.3.1 (only a single amino acid, e.g., L-phenylalanine, L-valine, L-leucine, L-threonine or L-isoleucine, is reduced by −40%), ■ culture in medium 5.3 (with all amino acids, control), ○ culture in medium 5.3.1 (L-phenylalanine −40%), × culture in medium 5.3.1 (L-valine −40%), ▶ culture in medium 5.3.1 (L-leucine is reduced by −40%), ∇ culture in medium 5.3.1 (L-threonine −40%), ◀ culture in medium 5.3.1 (L-isoleucine −40%). Shown are (L) viable cell concentration [1×10$^5$ cell/mL] CHO2 (CHO-DG44) Rituximab cells, (M) viability [%] CHO2 (CHO-DG44) Rituximab cells, (N) product concentration [mg/L] CHO2 (CHO-DG44) Rituximab, (O) lactate concentration [mg/L] CHO2 (CHO-DG44) Rituximab, controls were performed in triplicate (N=3) and test runs in duplicates (N=2).

Figure 3:
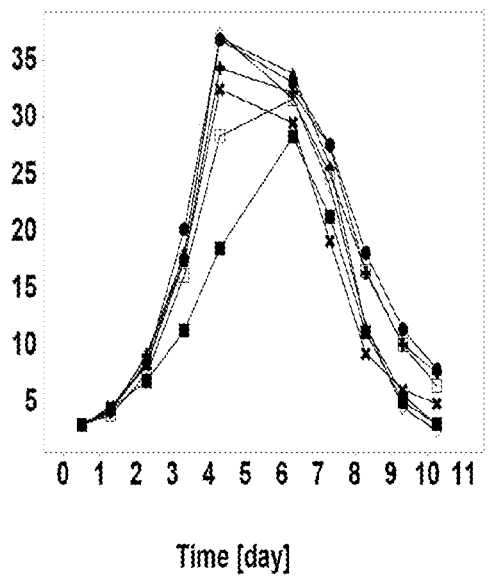
Figure 3:
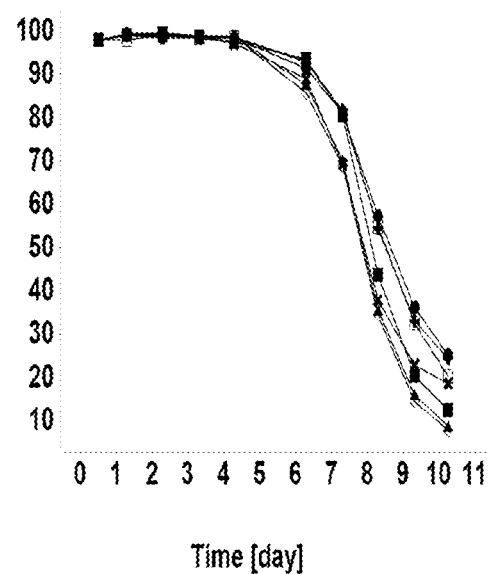
Figure 3:
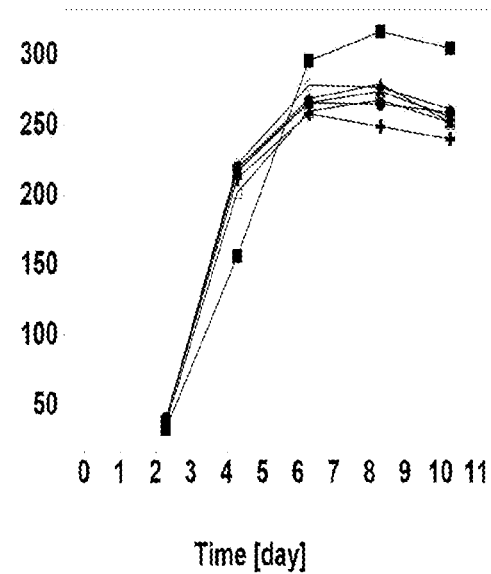

FIG. 3: Variation of a single amino acid by −40% based on optimized amino acid ratios in basal medium in a batch experiment. (A-C): Cells were cultivated in batch mode in medium 6.4.10-6.4.15 (only a single amino acid, e.g., L-lysine, L-methionine, L-proline, L-tryptophan or L-tyrosine, or the two amino L-tyrosine and L-lysine is/are reduced by −40%) or in control medium 6.4.0.1 (with optimized amino acid ratios), ■ culture in medium 6.4.0.1 (with all amino acids, control), + culture in medium 6.4.10 (L-tyrosine and L-lysine −40%), ▲ culture in medium 6.4.11 (L-tyrosine −40%), ☐ culture in medium 6.4.12 (L-lysine −40%), ● culture in medium 6.4.13 (L-methionine −40%), ◇ culture in medium 6.4.14 (L-tryptophan −40%), (×) culture in medium 6.4.15 (L-proline −40%). Shown are (A) viable cell concentration [1×10$^5$ cell/mL] CHO2 (CHO-DG44) Rituximab cells, (B) viability [%] CHO2 (CHO-DG44) Rituximab cells and (C) product concentration [mg/L] CHO2 (CHO-DG44) Rituximab, all experiments were performed in duplicates (N=2).

Figure 4:
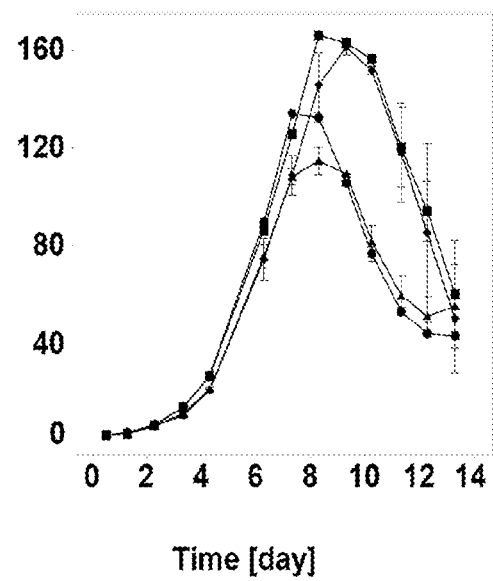
Figure 4:
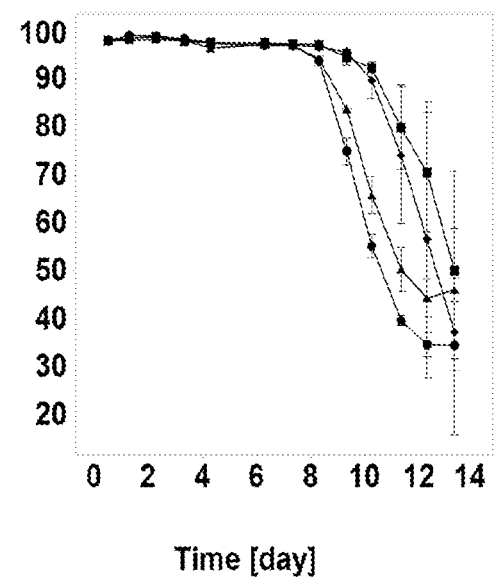
Figure 4:
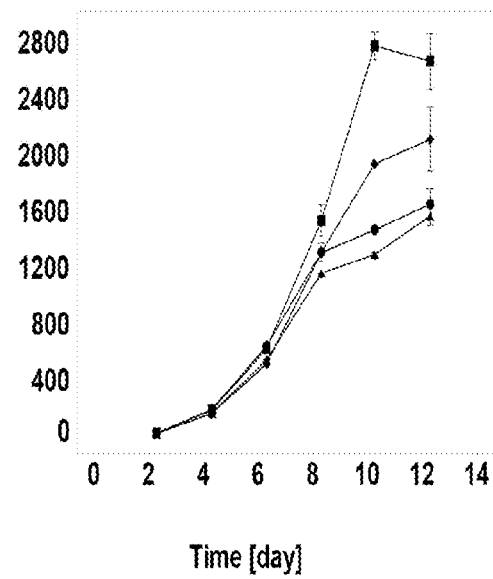
Figure 4:
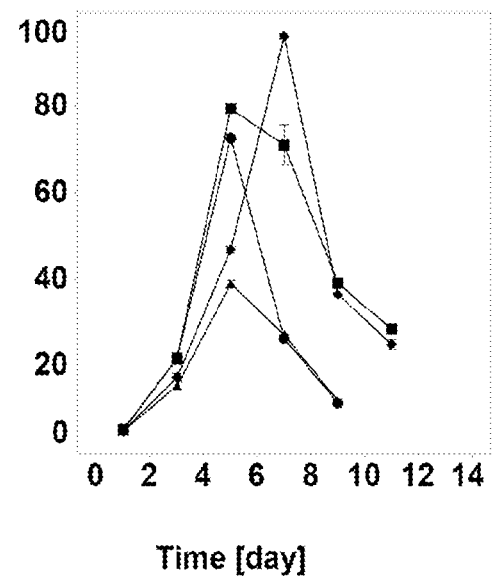
Figure 4:
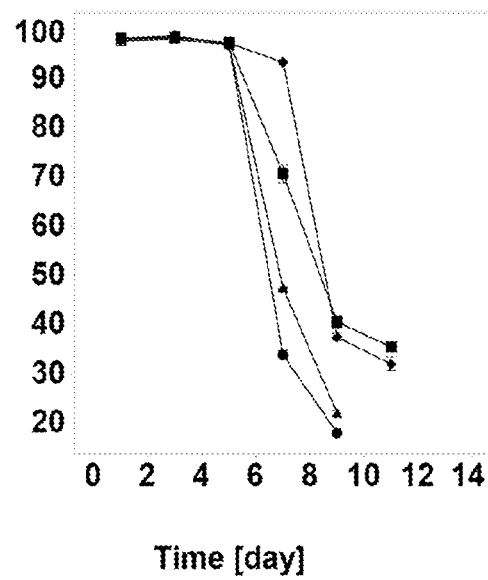
Figure 4:
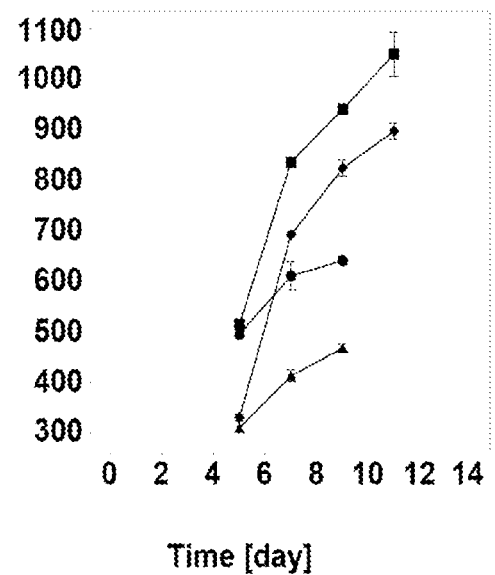
Figure 4:
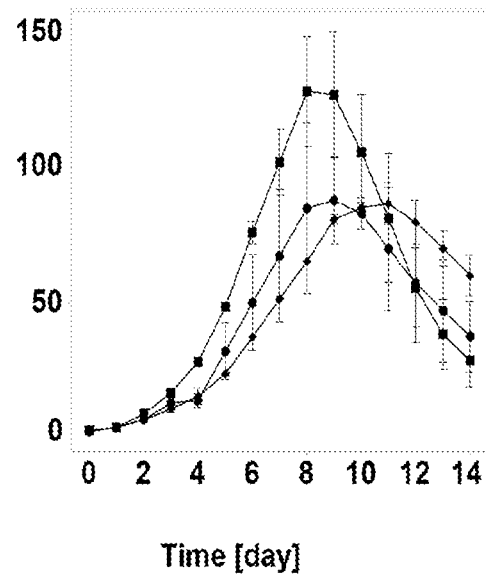
Figure 4:
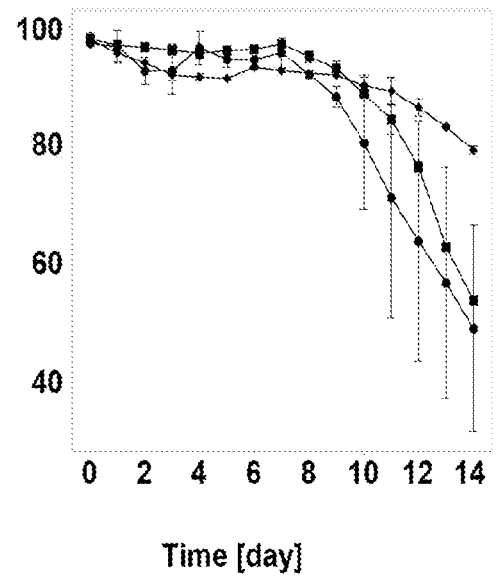
Figure 4:
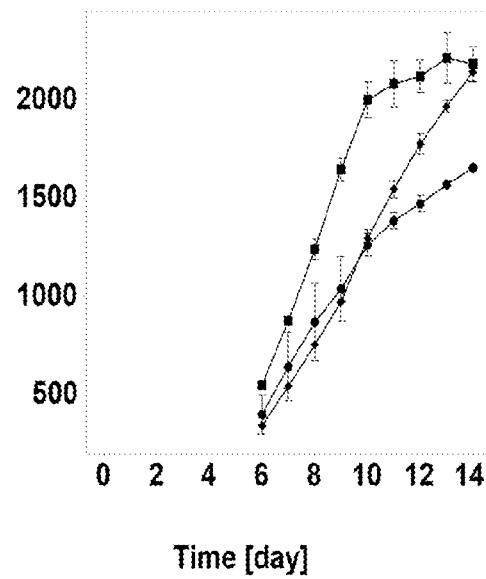
Figure 4:
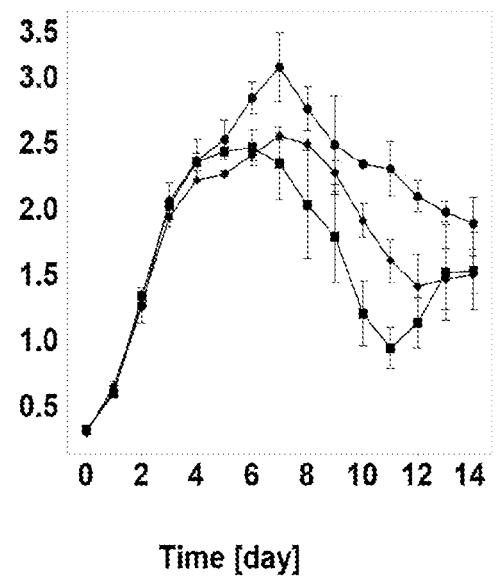
Figure 4:
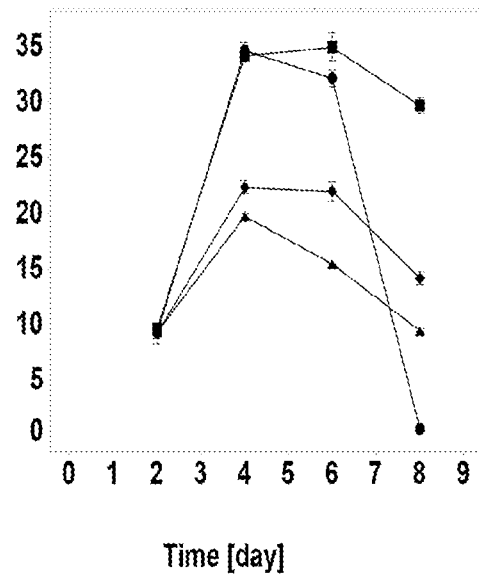
Figure 4:
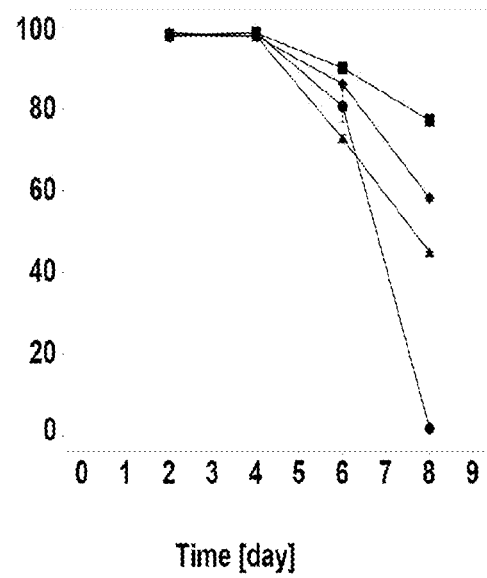
Figure 4:
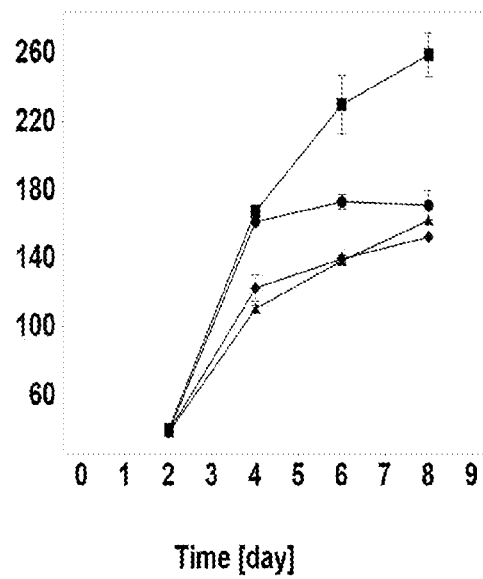
Figure 4:
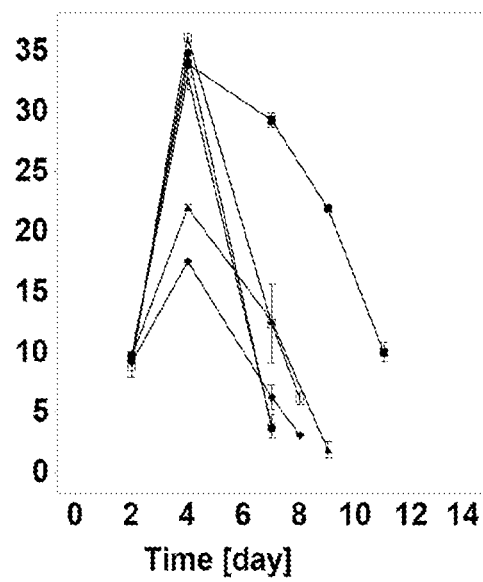
Figure 4:
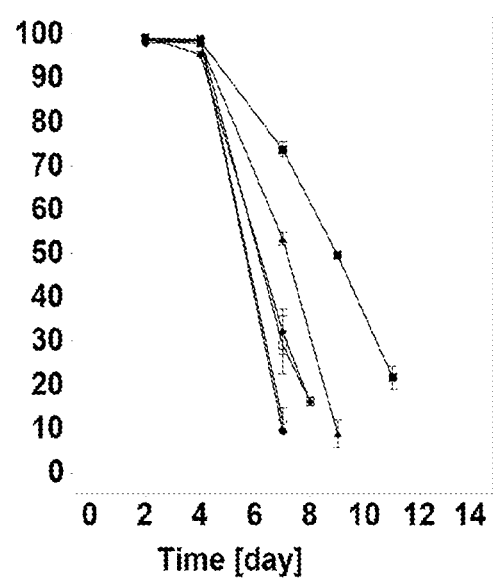
Figure 4:
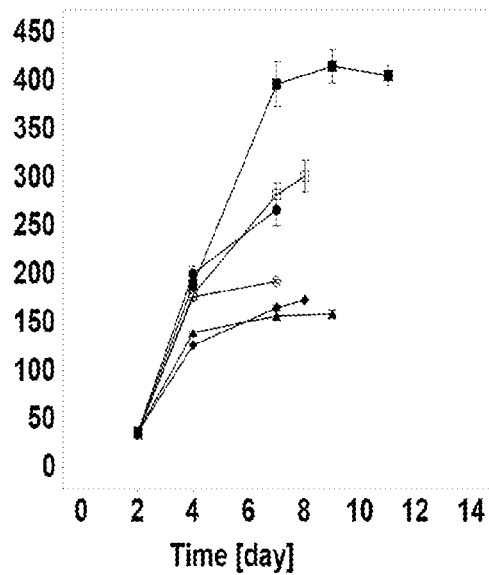

FIG. 4: Effect of optimized medium and feed medium in a fed-batch experiment at a standard or reduced feed rate.

(A-C): Effect of optimized basal medium and feed medium in a fed-batch experiment at a standard feed rate. Cells were cultivated in basal medium 6.2 (with optimized amino acid ratios), medium 6.3 (without optimized amino acid ratios), feed medium 6.2 (with optimized amino acid ratios) and feed medium 6.3 (without optimized amino acid ratios). CHO2 (CHO-DG44) Rituximab cells were cultured in various combinations of basal medium and feed medium, ■ culture in basal medium 6.2 (with optimized amino acid ratios) and feed medium 6.2 (with optimized amino acid ratios), ● culture in basal medium 6.2 (with optimized amino acid ratios) and feed medium 6.3 (without optimized amino acid ratios), ♦ culture in basal medium 6.3 (without optimized amino acid ratios) and feed medium 6.2 (with optimized amino acid ratios), ▲ culture in basal medium 6.3 (without optimized amino acid ratios) and feed medium 6.3 (without optimized amino acid ratios, shown are (A) viable cell concentration [1×10⁵ cell/mL] CHO2 (CHO-DG44) Rituximab cells, (B) viability [%] CHO2 (CHO-DG44) Rituximab cells and (C) product concentration [mg/L] CHO2 (CHO-DG44) Rituximab, all experiments were performed in duplicates (N=2).

(D-F): Effect of optimized basal medium and feed medium at a reduced feed rate. Cells were cultivated in medium 6.2 (with optimized amino acid ratios), medium 6.3 (without optimized amino acid ratios), feed medium 6.2 (with optimized amino acid ratios) and feed medium 6.3 (without optimized amino acid ratios). CHO2 (CHO-DG44) Rituximab cells were cultured in various combinations of basal medium and feed medium. The feed rate for all cultures was reduced to provoke a strong response of the cultures, ■ culture in basal medium 6.2 (with optimized amino acid ratios) and feed medium 6.2 (with optimized amino acid ratios and reduced feed rate, ● culture in basal medium 6.2 (with optimized amino acid ratios) and feed medium 6.3 (without optimized amino acid ratios), ♦ culture in basal medium 6.3 (without optimized amino acid ratios) and feed medium 6.2 (with optimized amino acid ratios), ▲ culture in basal medium 6.3 (without optimized amino acid ratios) and feed medium 6.3 (without optimized amino acid ratios). Shown are (D) viable cell concentration [1×10⁵ cell/mL] CHO2 (CHO-DG44) Rituximab cells, (E) viability [%] CHO2 (CHO-DG44) Rituximab cells and (F) product concentration [mg/L] CHO2 (CHO-DG44) Rituximab, all experiments were performed in duplicates (N=2).

(G-J): Effect of optimized medium and feed medium in 2-L scale. Cells were cultivated in a fully controlled 2-L system in medium 6.2 (with optimized amino acid ratios), medium 6.3 (without optimized amino acid ratios), feed medium 6.2 (with optimized amino acid ratios) and feed medium 6.3 (without optimized amino acid ratios). CHO2 (CHO-DG44) Rituximab cells were cultured in various combinations of optimized basal medium and feed medium, ■ culture in basal medium 6.2 (with optimized amino acid ratios) and feed medium 6.2 (with optimized amino acid ratios, ● culture in basal medium 6.2 (with optimized amino acid ratios) and feed medium 6.3 (without optimized amino acid ratios), ♦ culture in basal medium 6.3 (without optimized amino acid ratios) and feed medium 6.2 (with optimized amino acid ratios), shown are (G) viable cell concentration [1×10⁵ cell/mL] CHO2 (CHO-DG44) Rituximab cells, (H) viability [%] CHO2 (CHO-DG44) Rituximab cells, (I) product concentration [mg/L] CHO2 (CHO-DG44) Rituximab, (J) lactate concentration [g/L] CHO2 (CHO-DG44) Rituximab, all experiments were performed in duplicates (N=2).

(K-M): Effect of optimized RPMI medium and RPMI feed medium. Cells were cultivated in RPMI basal medium 3.1 (without optimized amino acid ratios), RPMI medium 3.9 (with optimized amino acid ratios), RPMI feed medium-2 (without optimized amino acid ratios) and RPMI feed medium-3 (with optimized amino acid ratios). CHO2 (CHO-DG44) Rituximab cells were cultured in various combinations of optimized basal medium and feed medium, ■ culture in RPMI medium 3.9 (with optimized amino acid ratios) and RPMI feed medium-3 (with optimized amino acid ratios, ● culture in RPMI medium 3.9 (with optimized amino acid ratios) and RPMI feed medium-2 (without optimized amino acid ratios), ♦ culture in RPMI medium 3.1 (without optimized amino acid ratios) and RPMI feed medium-3 (with optimized amino acid ratios), ▲ culture in RPMI medium 3.1 (without optimized amino acid ratios) and RPMI feed medium-2 (without optimized amino acid ratios), shown are (K) viable cell concentration [1×10⁵ cell/mL] CHO2 (CHO-DG44) Rituximab cells, (L) viability [%] CHO2 (CHO-DG44) Rituximab cells, (M) product concentration [mg/L] CHO2 (CHO-DG44) Rituximab, all experiments were performed in duplicates (N=2).

(N-P): Effect of optimized RPMI medium and RPMI feed medium compared to basal and feed medium without optimized amino acid (AA) ratios or spend media optimized AA ratios. Cells were cultivated in RPMI medium 3.1 (without optimized amino acid ratios), RPMI medium 3.9 (with optimized amino acid ratios), RPMI feed medium-2 (without optimized amino acid ratios) and RPMI feed medium-3 (with optimized amino acid ratios), RPMI medium 3.5 (with spend media supplemented AAs), RPMI feed medium 3.5 (with spend media supplemented AAs). CHO2 (CHO-DG44) Rituximab cells were cultured in various combinations of RPMI basal medium and RPMI feed medium, ■ culture in RPMI medium 3.9 (with optimized amino acid ratios) and RPMI feed medium-3 (with optimized amino acid ratios, ● culture in RPMI medium 3.9 (with optimized amino acid ratios) and RPMI feed medium-2 (without optimized amino acid ratios, ♦ culture in RPMI medium 3.1 (without optimized amino acid ratios) and RPMI feed medium-2 (without optimized amino acid ratios), ▲ culture in RPMI medium 3.1 (without optimized amino acid ratios) and RPMI feed medium-3 (with optimized amino acid ratios, ○ culture in RPMI medium 3.5 (with spend media supplemented AAs) and RPMI feed medium-2 (without optimized amino acid ratios), □ culture in RPMI medium 3.5 (with spend media supplemented AAs) and RPMI feed medium-3.5 (with spend media supplemented AAs), shown are (N) viable cell concentration [1×10⁵ cell/mL] CHO2 (CHO-DG44) Rituximab cells, (O) viability [%] CHO2 (CHO-DG44) Rituximab cells and (P) product concentration [mg/L] CHO2 (CHO-DG44) Rituximab, all experiments were performed in duplicates (N=2).

Figure 5:
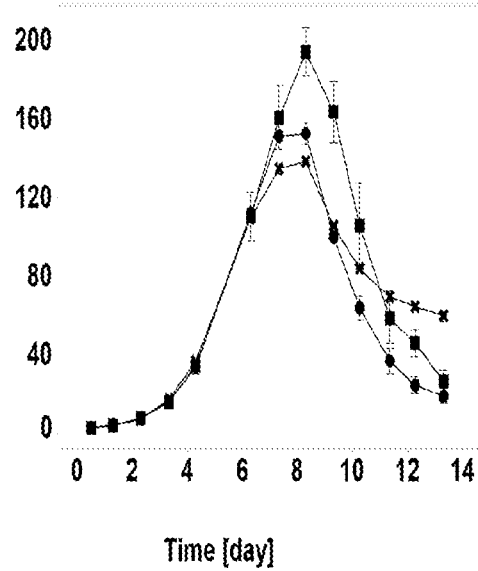
Figure 5:
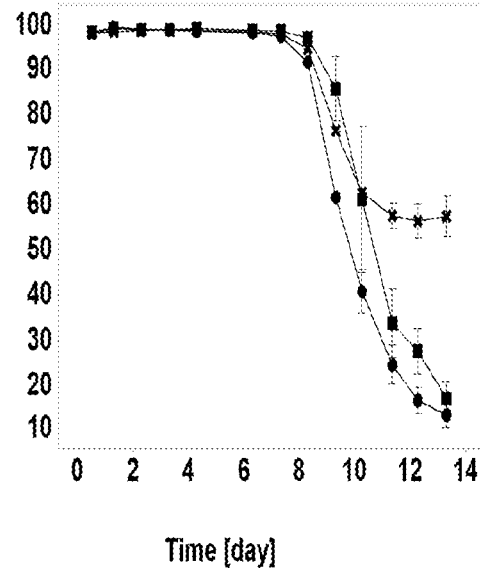
Figure 5:
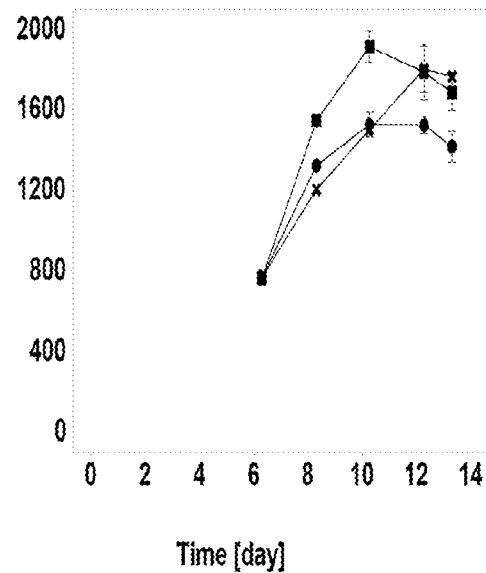
Figure 5:
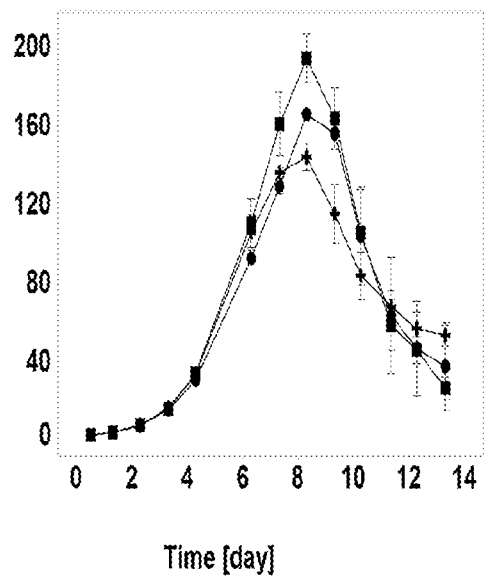
Figure 5:
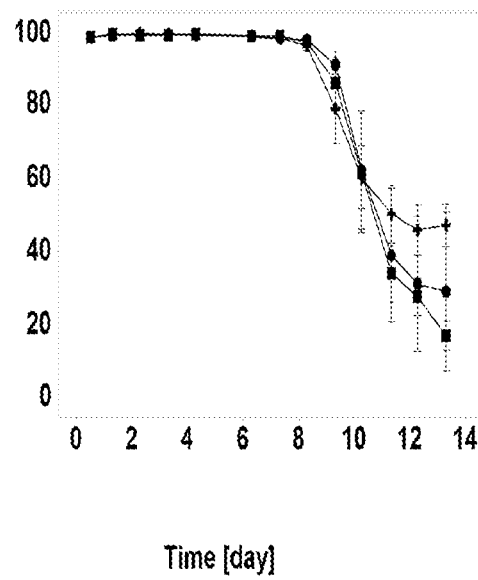
Figure 5:
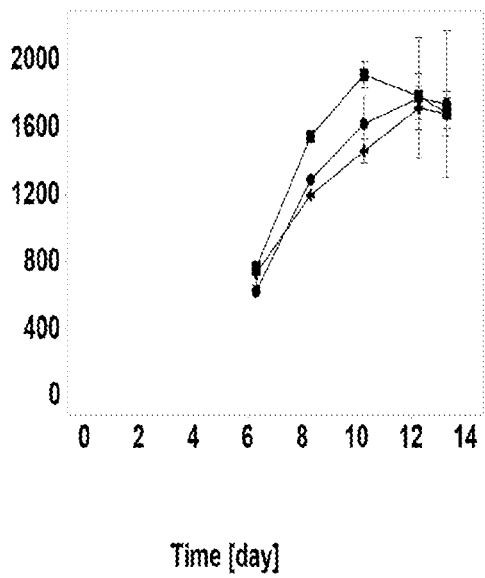
Figure 5:
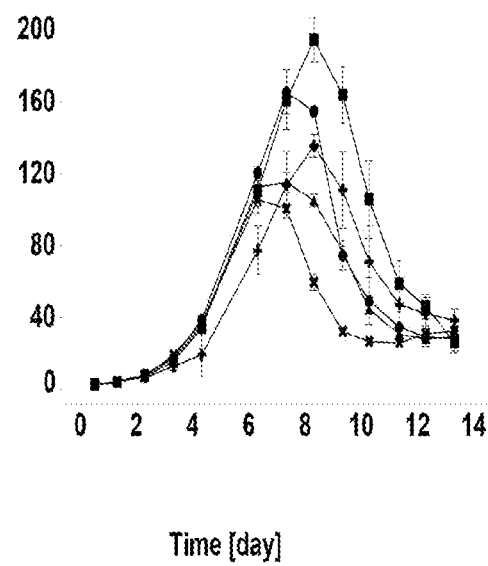
Figure 5:
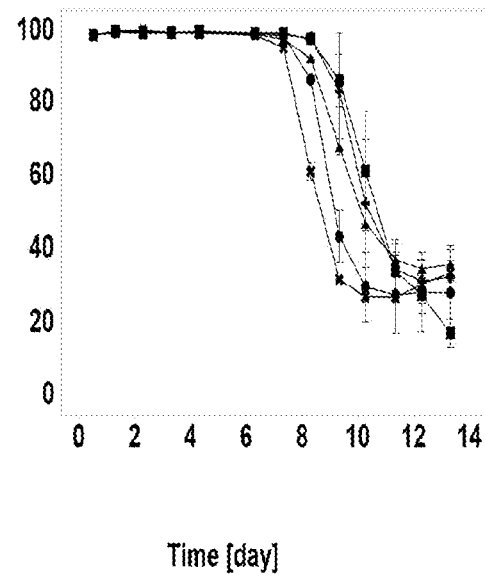
Figure 5:
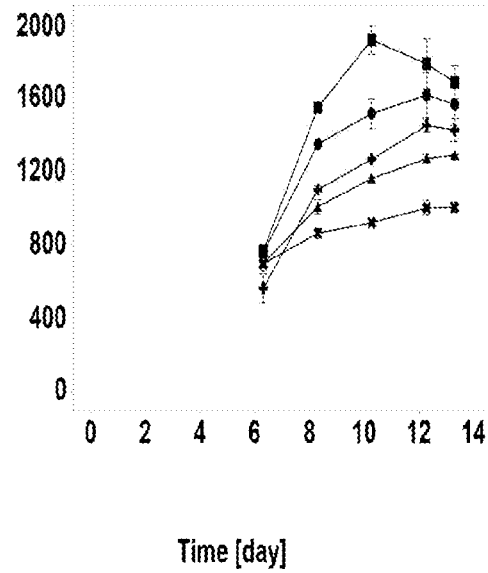

FIG. 5: Variation of 5 or 7 amino acids by +/−20% or +/−40% in a fed batch experiment.

(A-C): Variation of 5 amino acids by +/−40% based on novel amino acid ratios in optimized medium and feed. The amino acids L-phenylalanine, L-valine, L-leucine, L-threonine, L-isoleucine were varied by +/−40% in a positive or negative alternating mode (capital or non-capital AA letters) compared to control (with optimized amino acid ratios). CHO2 (CHO-DG44) Rituximab cells were cultured in fed-batch in medium 6.4.0.1 (with optimized amino acid ratios, control), basal medium 6.4.3 (5 amino acids PHE, val, LEU, thr, ILE varied by +/−40%, positive), basal medium 6.4.4 (5 amino acids phe, VAL, leu, THR, ile varied by +/−40%, negative), feed medium 6.4 (with optimized amino acid ratios, control), feed medium 6.4.3 (5 amino acids PHE, val, LEU, thr, ILE varied by +/−40%, positive), feed medium 6.4.4 (5 amino acids phe, VAL, leu, THR, ile varied by +/−40%, negative), ■ culture in basal medium 6.4.0.1 and feed medium 6.4 (with optimized amino acid ratios, control), × culture in basal medium 6.4.3 and feed medium 6.4.3 (5 amino acids PHE, val, LEU, thr, ILE varied by +/−40%, positive), ● culture in basal medium 6.4.4 and feed medium 6.4.4 (5 amino acids phe, VAL, leu, THR, ile varied by +/−40%, negative), shown are (A) viable cell concentration [1×10⁵ cell/mL] CHO2 (CHO-DG44) Rituximab cells, (B)

viability [%] CHO2 (CHO-DG44) Rituximab cells and (C) product concentration [mg/L] CHO2 (CHO-DG44) Rituximab, all experiments were performed in duplicates (N=2).

(D-F): Variation of 7 amino acids based on novel amino acid ratios in optimized medium and feed. The amino acids L-phenylalanine, L-valine, L-leucine, L-threonine, L-isoleucine, L-tyrosine, L-lysine were varied by +/−40% in a positive or negative alternating mode (capital or non-capital AA letters) compared to control (with optimized amino acid ratios). CHO2 (CHO-DG44) Rituximab cells were cultured in fed-batch in medium 6.4.0.1 (with optimized amino acid ratios, control), basal medium 6.4.7 (7 amino acids PHE, val, LEU, thr, ILE, tyr, LYS varied by +/−40%, positive), basal medium 6.4.8 (7 amino acids phe, VAL, leu, THR, ile, TYR, lys varied by +/−40%, negative), feed medium 6.4 (with optimized amino acid ratios, control), feed medium 6.4.7 (7 amino acids PHE, val, LEU, thr, ILE, tyr, LYS varied by +/−40%, positive), feed medium 6.4.8 (7 amino acids phe, VAL, leu, THR, ile, tyr, lys varied by +/−40%, negative), ■ culture in basal medium 6.4.0.1 and feed medium 6.4 (with optimized amino acid ratios, control), + culture in basal medium 6.4.7 and feed medium 6.4.7 (7 amino acids PHE, val, LEU, thr, ILE, tyr, LYS varied by +/−40%, positive), ● culture in basal medium 6.4.8 (7 amino acids phe, VAL, leu, THR, ile, TYR, lys varied by +/−40%, negative) and feed medium 6.4.8 (7 amino acids phe, VAL, leu, THR, ile, tyr, lys varied by +/−40%, negative), shown are (D) viable cell concentration [1×10$^5$ cell/mL] CHO2 (CHO-DG44) Rituximab cells, (E) viability [%] CHO2 (CHO-DG44) Rituximab cells, (F) product concentration [mg/L] CHO2 (CHO-DG44) Rituximab, all experiments were performed in duplicates (N=2).

(G-H): Variation of 7 amino acids based on novel amino acid ratios in optimized medium and feed. The amino acids L-phenylalanine, L-valine, L-leucine, L-threonine, L-isoleucine, L-tyrosine, L-lysine were varied by +/−20% and +/−40% in a positive or negative alternating mode at reduced feed rates (capital or non-capital AA letters) compared to control (with optimized amino acid ratios). CHO2 (CHO-DG44) Rituximab cells were cultured in fed-batch in medium 6.4.0.1 and feed medium 6.4 (with optimized amino acid ratios, for control standard feed rate and also reduced feed rate), basal medium 6.4.5 (7 amino acids PHE, val, LEU, thr, ILE, tyr, LYS varied by +/−20%, positive), basal medium 6.4.7 (7 amino acids PHE, val, LEU, thr, ILE, tyr, LYS varied by +/−40%, positive), basal medium 6.4.8 (7 amino acids phe, VAL, leu, THR, ile, TYR, lys varied by +/−40%, negative), feed medium 6.4 (with optimized amino acid ratios, control), feed medium 6.4.5 (7 amino acids PHE, val, LEU, thr, ILE, tyr, LYS varied by +/−20%, positive), feed medium 6.4.7 (7 amino acids PHE, val, LEU, thr, ILE, tyr, LYS varied by +/−40%, positive) and feed medium 6.4.8 (7 amino acids phe, VAL, leu, THR, ile, tyr, lys varied by +/−40%, negative) at reduced feed rate, ■ culture in basal medium 6.4.0.1 and feed medium 6.4 (with optimized amino acid ratios, control) at standard feed rate, ● culture in basal medium 6.4.0.1 and feed medium 6.4 (with optimized amino acid ratios, control) and reduced feed rate, + culture in basal medium 6.4.5 (7 amino acids PHE, val, LEU, thr, ILE, tyr, LYS varied by +/−20%, positive) and feed medium 6.4.5 (7 amino acids PHE, val, LEU, thr, ILE, tyr, LYS varied by +/−20%, positive), × culture in basal medium 6.4.7 (7 amino acids PHE, val, LEU, thr, ILE, tyr, LYS varied by +/−40%, positive) and feed medium 6.4.7 (7 amino acids PHE, val, LEU, thr, ILE, tyr, LYS varied by +/−40%, positive), ▲ culture in basal medium 6.4.8 (7 amino acids phe, VAL, leu, THR, ile, TYR, lys varied by +/−40%, negative) and feed medium 6.4.8 (7 amino acids phe, VAL, leu, THR, ile, tyr, lys varied by +/−40%, negative), shown are (G) viable cell concentration [1×10$^5$ cell/mL] CHO2 (CHO-DG44) Rituximab cells, (H) viability [%] CHO2 (CHO-DG44) Rituximab cells, and (I) product concentration [mg/L] CHO2 (CHO-DG44) Rituximab, all experiments were performed in duplicates (N=2).

Figure 6:
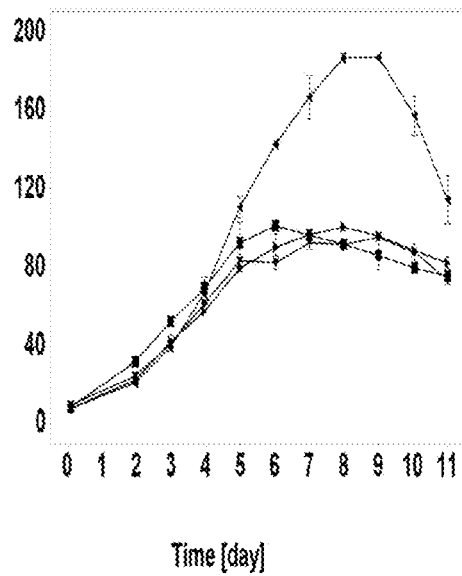
Figure 6:
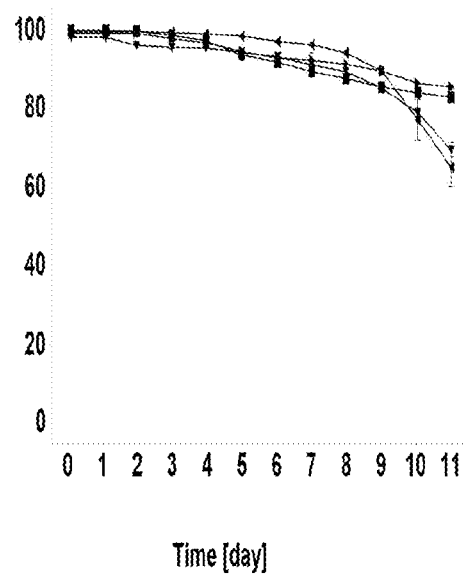
Figure 6:
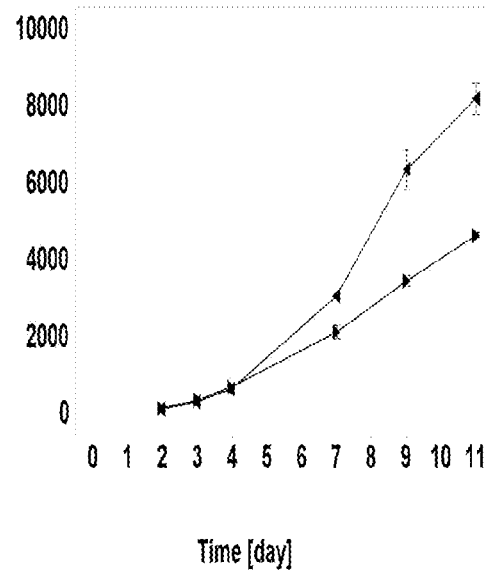
Figure 6:
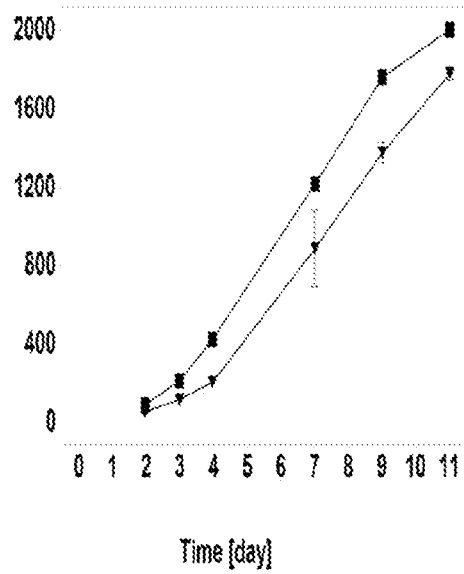

FIG. 6: Fed-Batch of CHO-DG44 derived cell lines producing different therapeutic molecules were cultivated in an optimized basal medium 6.2 and feed medium 6.2 (with optimized amino acid ratios in basal medium and feed medium, without hydroxyl-L-proline), ▼ Fc-fusion protein produced in CHO-DG44 cells, ■ Rituximab (IgG1 kappa) antibody produced in CHO-DG44 cells (CHO2 (CHO-DG44) Rituximab), ▶ mAb5/IgG1 kappa antibody produced in CHO-DG44 cells, ◀ mAb6/IgG1 kappa produced in CHO-DG44 cells. Shown are (A) viable cell concentration [1×10$^5$ cell/mL], (B) viability [%] CHO-DG44, (C) product concentration [mg/L] for mAb5/IgG1 and mAb6/IgG1, and (D) product concentration [mg/L] Fc-fusion protein and Rituximab, all experiments were performed in duplicates (N=2).

Figure 7:
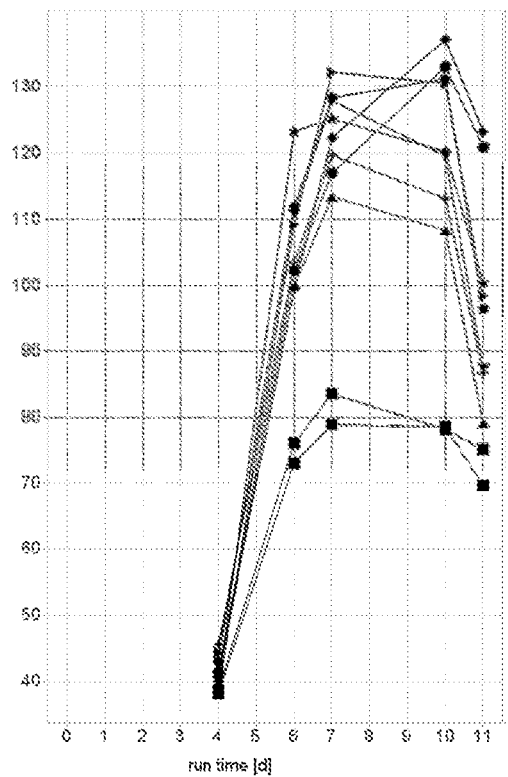
Figure 7:
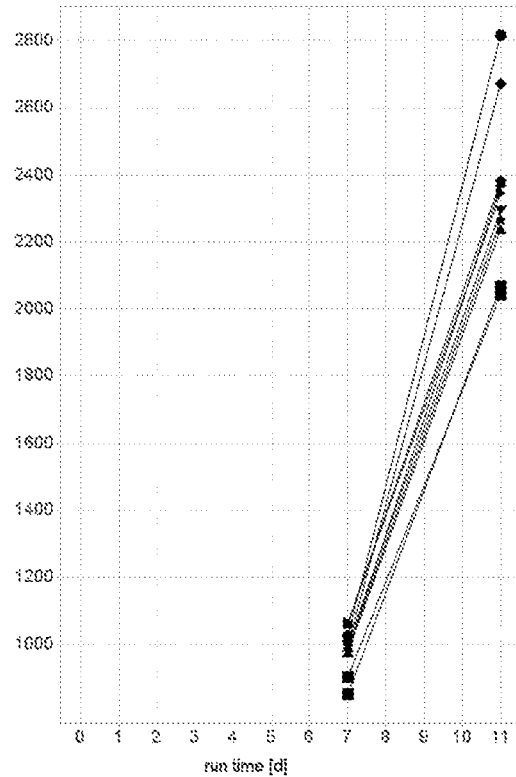
Figure 7:
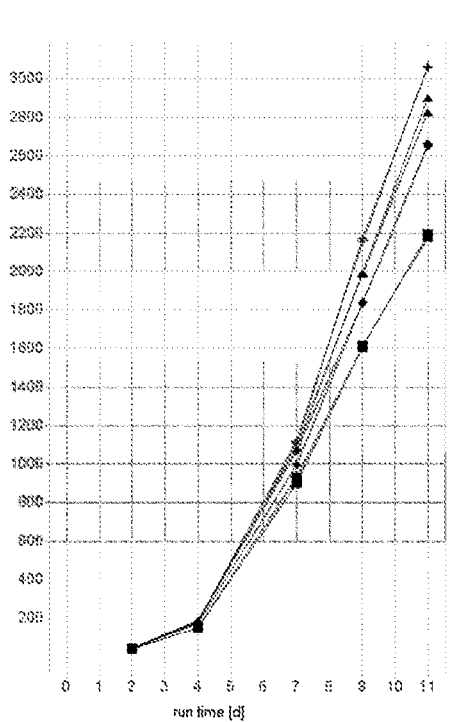
Figure 7:
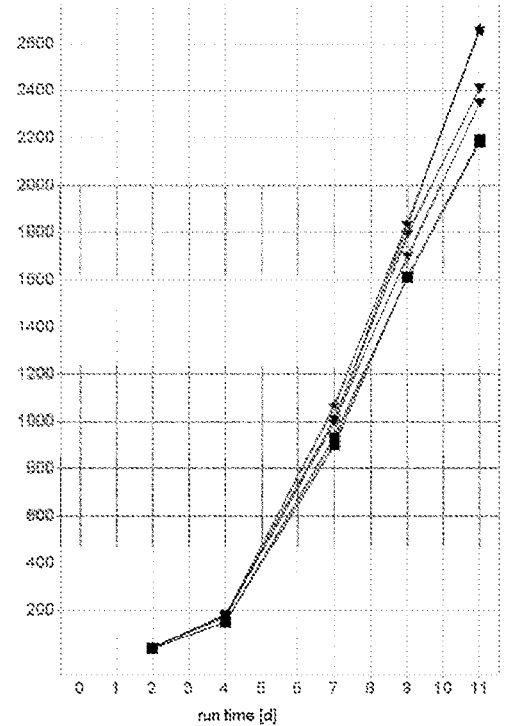

FIG. 7: Comparison of iron choline citrate with other iron carrier at about equimolar amounts.

(A, B) CHO2 (CHO-DG44) Rituximab cells were cultured in basal medium 6.2a with the indicated iron carrier in the basal medium and feed medium 6.2a without iron choline citrate in fed batch mode, ■ culture in basal medium 0.2 g/L iron choline citrate, ● culture in basal medium with 1.0 g/L iron choline citrate; ♦ culture in basal medium with 2.0 g/L iron choline citrate; ▲ culture in basal medium with 0.5 g/L iron pyro phosphate; + culture in basal medium with 0.8 g/L iron pyro phosphate, (filled star) culture in basal medium with 1.3 g/L iron pyro phosphate, ▼ culture in basal medium with 0.3 g/L iron phosphate, (filled pentagon) culture in basal medium with 0.5 g/L iron phosphate, ▶ culture in basal medium with 0.7 g/L iron phosphate. Shown are (A) viable cell concentration [1×10$^5$ cell/mL] CHO2 (CHO-DG44) Rituximab cells, (B) product concentration [mg/L] CHO2 (CHO-DG44) Rituximab, all experiments were performed in duplicates (N=2).

(C) Product concentration [mg/L] of CHO2 (CHO-DG44) Rituximab cells cultured in basal medium 6.2a with different concentrations of iron choline citrate and feed medium 6.2a containing 0.56 g/l iron choline citrate in fed batch mode (N=2), ■ culture in basal medium without iron choline citrate, ♦ culture in basal medium with 0.2 g/L iron choline citrate; ▲ culture in basal medium with 0.4 g/L iron choline citrate; + culture in basal medium with 2.0 g/L iron choline citrate.

(D) Product concentration [mg/L] of CHO2 (CHO-DG44) Rituximab cells cultured in basal medium 6.2a and feed medium 6.2a with iron choline citrate or iron citrate at about equimolar amounts in fed batch mode (N=2), ■ culture in basal medium without iron choline citrate and feed medium with 0.56 g/l iron choline citrate, (filled star) culture in basal medium with 0.2 g/L iron choline citrate and feed medium with 0.56 g/l iron choline citrate; ▼ culture in basal medium with 0.1 g/L iron citrate and feed medium with 0.25 g/l iron citrate.

Figure 8:
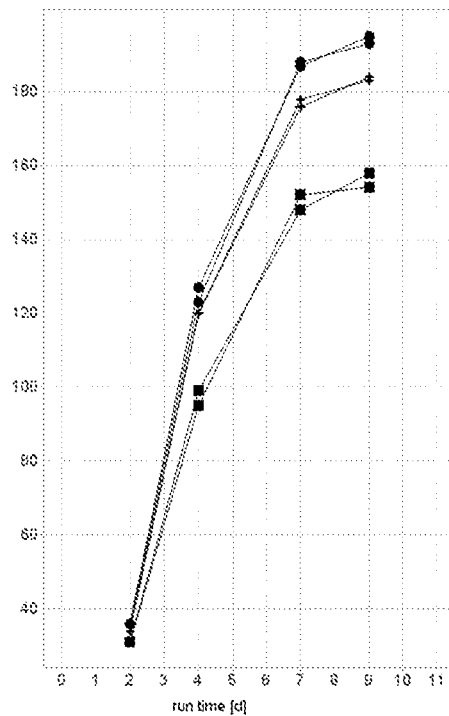
Figure 8:
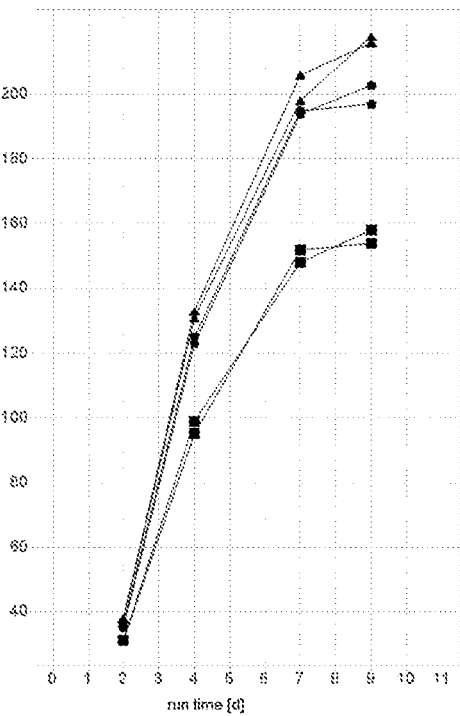
Figure 8:
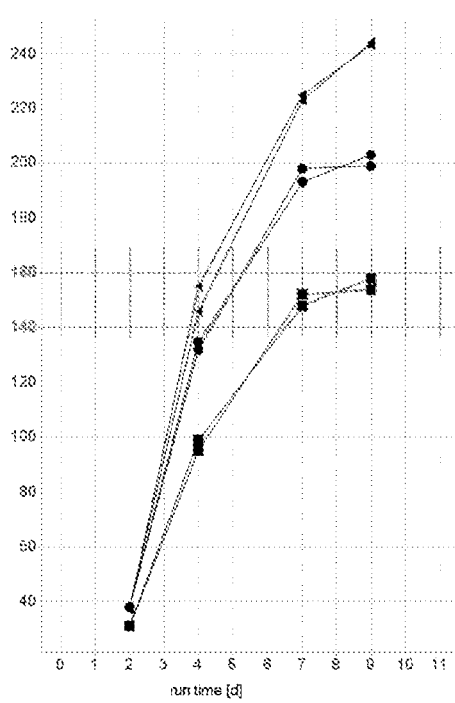
Figure 8:
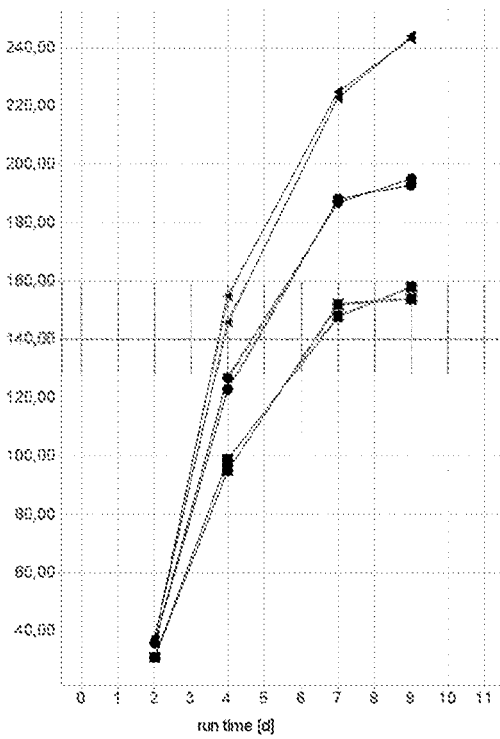

FIG. 8: Comparison of iron choline citrate with iron citrate at about equimolar amounts in RPMI based medium. Product concentration CHO2 (CHO-DG44) Rituximab cells cultured in basal medium 3.1 with iron choline citrate or iron citrate at about equimolar amounts and feed medium 2 containing 0.25 g/l iron citrate in fed batch mode (N=2), ■ culture in basal medium without iron choline citrate, ● culture in basal medium with 0.2 g/L iron choline citrate; + culture in basal medium with 0.1 g/L iron citrate. Shown are product concentration [mg/L] CHO2 (CHO-DG44) Rituximab comparing (A) 0.2 g/l iron choline citrate (●) with 0.1 g/l iron citrate (+), (B) 0.4 g/l iron choline citrate (▲) with 0.2 g/l iron citrate (pentagon) (C) 2 g/l iron choline citrate (◄) with 1 g/l iron citrate (●) and (D) 0.2 g/l (●) and 2 g/l (◄) iron choline citrate.

Figure 9:
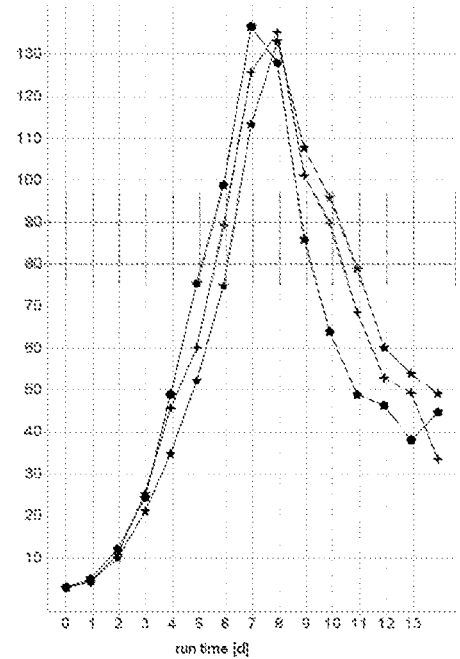
Figure 9:
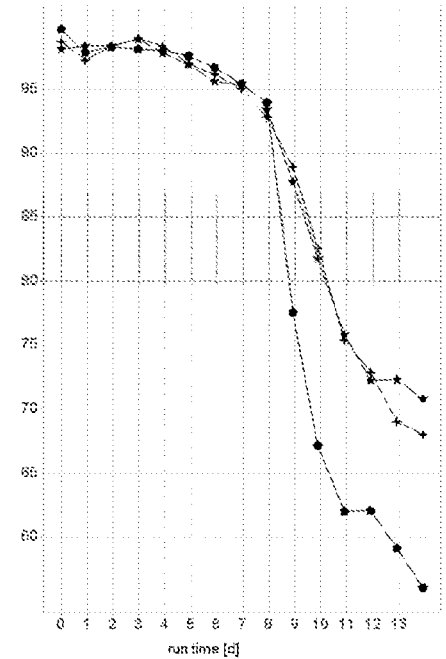
Figure 9:
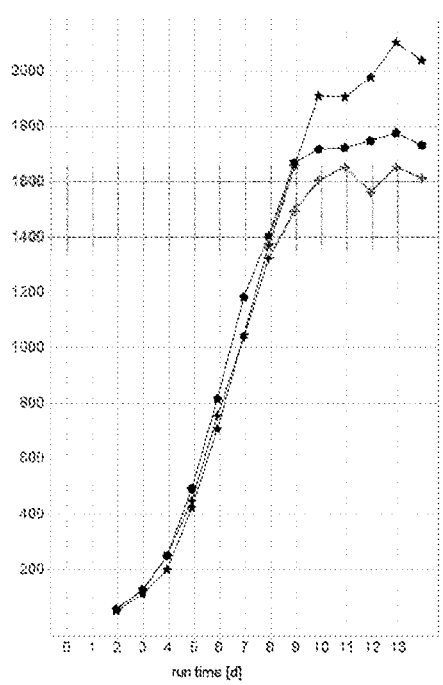
Figure 9:
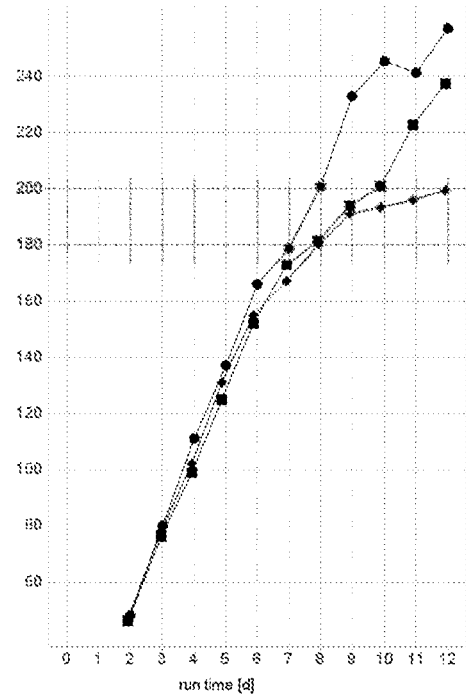

FIG. 9: Comparison of iron choline citrate with iron citrate at about equimolar amounts in medium 6.2a or RPMI based medium in fed batch mode in a 2 L bioreactor. CHO2 (CHO-DG44) Rituximab cells were cultured in (A-C) basal medium 6.2a with iron choline citrate or iron citrate and feed medium 6.2a containing 0.56 g/l iron choline citrate (D) or in basal medium 3.1 with iron choline citrate or iron citrate and feed medium-2 containing 0.25 g/l iron citrate in fed batch mode (N=2), +culture in basal medium 6.2a with 0.2 g/l iron choline citrate and feed medium 6.2a with 0.56 g/l iron choline citrate, (filled star) culture in basal medium 6.2a with 2 g/L iron choline citrate and feed medium 6.2a with 0.56 g/l iron choline citrate; (filled pentagon) culture in basal medium 6.2a with 1 g/L iron citrate and feed medium 6.2a with 0.56 g/l iron choline citrate. ■ culture in RPMI based basal medium 3.1 with 0.2 g/l iron choline citrate and feed medium 2 with 0.25 g/l iron citrate, ● culture in RPMI based basal medium 3.1 with 2 g/L iron choline citrate and feed medium 2 with 0.25 g/l iron citrate; ♦ culture in RPMI based basal medium 3.1 with 1 g/L iron citrate and feed medium 2 with 0.25 g/l iron citrate.

Figure 10:
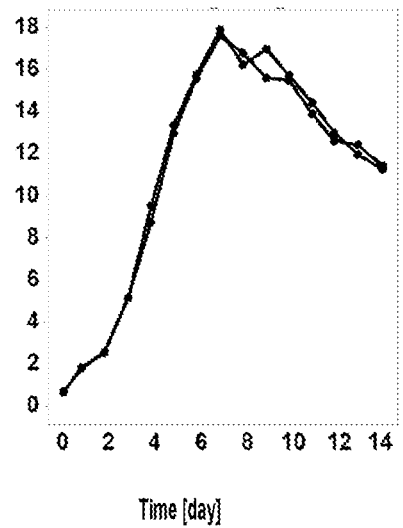
Figure 10:
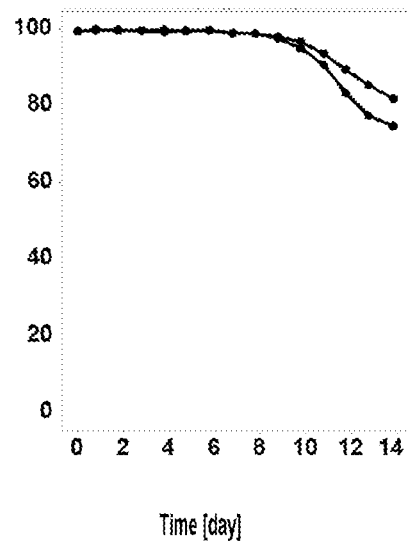
Figure 10:
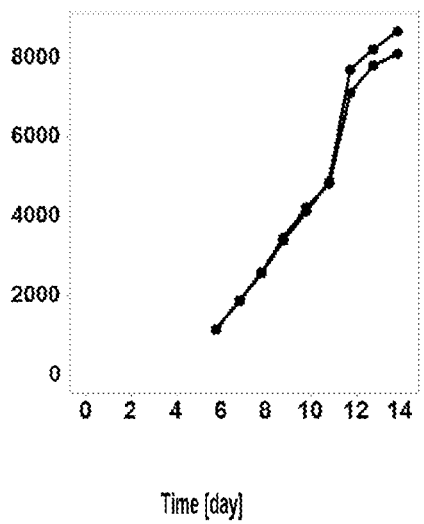

FIG. 10: Two fed-batch cultures of CHO-K1 GS derived cell lines producing Rituximab were cultivated in parallel in basal medium 6.2 GS and feed medium 6.2 GS, both with optimized AA ratios. Shown are (A) viable cell concentration [$1\times10^6$ cell/mL], (B) viability [%] of CHO-K1 GS cells producing Rituximab and (C) final product concentration after a 14 days cultivation process [mg/L].

DETAILED DESCRIPTION

Definitions

The general embodiments "comprising" or "comprised" encompass the more specific embodiment "consisting of". Furthermore, singular and plural forms are not used in a limiting way. Terms used in the course of this present invention have the following meaning.

The term "cell culture medium" as used herein is a medium to culture mammalian cells comprising a minimum of essential nutrients and components such as vitamins, trace elements, salts, bulk salts, amino acids, lipids, carbohydrates in a preferably buffered medium (preferably pH about 7.0, pH=7.3-6.6, pH=7.0). Non limiting examples for such cell culture media include commercially available media like RPMI, DMEM:F12, DMEM, Hams/F12 etc. as well as proprietary media from various sources (e.g. medium 6.2). The cell culture medium may be a basal cell culture medium. The cell culture medium may also be a basal cell culture medium to which the feed medium and/or additives have been added. The cell culture medium may also be referred to as fermentation broth, if the cells are cultured in a fermenter or bioreactor.

The term "basal medium" or "basal cell culture medium" as used herein is a cell culture medium to culture mammalian cells as defined below. It refers to the medium in which the cells are cultured from the start of a cell culture run and is not used as an additive to another medium, although various components may be added to the medium. The basal medium serves as the base to which optionally further additives or feed medium may be added during cultivation, i.e., a cell culture run. The basal cell culture medium is provided from the beginning of a cell cultivation process. In general, the basal cell culture medium provides nutrients such as carbon sources, amino acids, vitamins, bulk salts (e.g. sodium chloride or potassium chloride), various trace elements (e.g. manganese sulfate), pH buffer, lipids and glucose. Major bulk salts are usually provided only in the basal medium and must not exceed a final osmolarity in the cell culture of about 280-350 mOsmo/kg, so that the cell culture is able to grow and proliferate at a reasonable osmotic stress.

The term "feed" or "feed medium" as used herein relates to a concentrate of nutrients/a concentrated nutrient composition used as a feed in a culture of mammalian cells. It is provided as a "concentrated feed medium" to avoid dilution of the cell culture, typically a feed medium is provided at 10-50 ml/L/day, preferably at 15-45 ml/L/day, more preferably at 20-40 ml/L/day and even more preferably at 30 ml/L/day based on the culture starting volume (CSV, meaning the start volume on day 0) in the vessel. The feeding rate is to be understood as an average feeding rate over the feeding period. A feed medium typically has higher concentrations of most, but not all, components of the basal cell culture medium. Generally, the feed medium substitutes nutrients that are consumed during cell culture, such as amino acids and carbohydrates, while salts and buffers are of less importance and are commonly provided with the basal medium. The feed medium is typically added to the (basal) cell culture medium/fermentation broth in fed-batch mode. However, the feed may be added in different modes like continuous or bolus addition or via perfusion related techniques (chemostat or hybrid-perfused system). Preferably, the feed medium is added daily, but may also be added more frequently, such as twice daily or less frequently, such as every second day. The addition of nutrients is commonly performed during cultivation (i.e., after day 0). In contrast to the basal medium, the feed consists of a highly concentrated nutrient solution (e.g. >6x) that provides all the components similar to the basal medium except for 'high-osmolarity-active compounds' such as major bulk salts (e.g., NaCl, KCl, $NaHCO_3$, $MgSO_4$, $Ca(NO_3)_2$). Typically a >6x-fold concentrate or higher of the basal medium without or with reduced bulk salts maintains good solubility of compounds and sufficiently low osmolarity (e.g. 270-1500 mOsmo/kg, preferably 310-800 mOsmo/kg; medium 6.2 feed osmolarity is about 1500 mOsmo/kg due to high glucose, salts and optimized AA) in order to maintain osmolarity in the cell culture at about 270-550 mOsmo/kg, preferably at about 280-450 mOsmo/kg, more preferably at about 280-350 mOsmo/kg.

The cell culture medium, both basal medium and/or feed medium may be serum-free, chemically defined or chemically defined and protein-free. A "serum-free medium" as used herein refers to a cell culture medium for in vitro cell culture, which does not contain serum from animal origin. This is preferred as serum may contain contaminants from said animal, such as viruses, and because serum is ill-defined and varies from batch to batch. The basal medium and the feed medium according to the invention are serum-free.

A "chemically defined medium" as used herein refers to a cell culture medium suitable for in vitro cell culture, in which all components are known. More specifically it does not comprise any supplements such as animal serum or plant, yeast or animal hydrolysates. It may comprise hydrolysates only if all components have been analysed and the exact composition thereof is known and can be reproducibly prepared. The basal medium and the feed medium according to the invention are preferably chemically defined.

A "protein-free medium" as used herein refers to a cell culture medium for in vitro cell culture comprising no proteins, except for proteins produced by the cell to be cultured, wherein protein refers to polypeptides of any length, but excludes single amino acids, dipeptides or tripeptides. Specifically growth factors such as insulin and insulin-like growth factor (IGF) are not present in the medium. Preferably, the basal medium and feed medium according to the present invention are chemically defined and protein-free.

As used herein, the "medium platform", or "media platform" consists of a basal cell culture medium, which is provided from the beginning of a cell cultivation process and a feed medium, which is added to the basal cell culture medium during cultivation. Optionally further additives, such as glucose, may be added during the cell cultivation process. The feed medium may be supplied in any kind of fed batch process mode (e.g. continuous, with changing feed rates or as bolus feed additions).

The term "commercially available media/media systems" as used herein refers to commercially available cell culture media with completely known composition. These media serve as references for the media of the present invention due to the requirement for exact nutrient composition. Commercially available media are, e.g., DMEM:F12 (1:1), DMEM, HamsF12, and RPMI. The feed medium of the commercial media used herein were prepared as a 12-fold concentrate of the basal medium without bulk salts. The term "commercially available media systems" relate to a system comprising of a commercially available basal cell culture medium, such as DMEM:F12 (1:1), DMEM, HamsF12, and RPMI and a feed medium, which is the respective concentrated basal medium (e.g., 12-fold concentrated) without or with reduced bulk salts.

As used herein, "1×" means the standard concentration normally used in a particular basal medium, "2×" means twice the standard concentration, etc. The feed medium is for example preferably a 6× to 20× solution, i.e., 6 to 20-fold the standard concentration in the basal medium that is used for amino acid optimization without considering bulk salts such as sodium chloride or potassium chloride. However, the skilled person will understand that the cell culture requirements are different during, e.g., the exponential growth phase and the protein production phase. Thus, preferably the basal medium and the feed medium are adapted to these altered requirements. Hence, the amino acid ratios in the feed medium are typically different to the amino acid ratios in the basal medium.

The term "cell cultivation" or "cell culture" includes cell cultivation and fermentation processes in all scales (e.g. from micro titer plates to large-scale industrial bioreactors, i.e. from sub mL-scale to >10.000 L scale), in all different process modes (e.g. batch, fed-batch, perfusion, continuous cultivation), in all process control modes (e.g. non-controlled, fully automated and controlled systems with control of e.g. pH, temperature, oxygen content), in all kind of fermentation systems (e.g. single-use systems, stainless steel systems, glass ware systems). In a preferred embodiment of the present invention the cell culture is a mammalian cell culture and is a batch or a fed-batch culture.

The term "fed-batch" as used herein relates to a cell culture in which the cells are fed continuously or periodically with a feed medium containing nutrients. The feeding may start shortly after starting the cell culture on day 0 or more typically one, two or three days after starting the culture. Feeding may follow a preset schedule, such as every day, every two days, every three days etc. Alternatively, the culture may be monitored for cell growth, nutrients or toxic by-products and feeding may be adjusted accordingly. Common monitoring methods for animal cell culture are described in the experimental part below. In general, the following parameters are often determined on a daily basis and cover the viable cell concentration, product concentration and several metabolites such as glucose or lactic acid (an acidic waste metabolite that reduces the pH and is derived from cellular glucose conversion), pH, osmolarity (a measure for salt content) and ammonium (growth inhibitor that negatively affects the growth rate and reduces viable biomass). Compared to batch cultures (cultures without feeding), higher product titers can be achieved in the fed-batch mode. Typically, a fed-batch culture is stopped at some point and the cells and/or the protein of interest in the medium are harvested and optionally purified.

The terms "vitality" and "viability" are synonymously used and refers to the % viable cells in a cell culture as determined by methods known in the art, e.g., trypan blue exclusion with a Cedex device based on an automated-microscopic cell count (Innovatis AG, Bielefeld). However, there exist of number of other methods for the determination of the viability such as fluorometric (such as based on propidium iodide), calorimetric or enzymatic methods that are used to reflect the energy metabolism of a living cell e.g. methods that use LDH lactate-dehydrogenase or certain tetrazolium salts such as alamar blue, MTT (3-(4,5-dimethylthiazol-2-yl-2,5-diphenyltetrazolium bromide) or TTC (tetrazolium chloride).

The term "amino acid" as used herein refers to the twenty natural amino acids that are encoded by the universal genetic code, typically the L-form (i.e., L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine). The amino acids (e.g., glutamine and/or tyrosine) may be provided as dipeptides with increased stability and/or solubility, preferably containing an L-alanine (L-ala-x) or L-glycine extension (L-gly-x), such as glycyl-glutamine and alanyl-glutamine. Further, cysteine may also be provided as L-cystine. The term "amino acids" as used herein encompasses all different salts thereof, such as (without being limited thereto) L-arginine monohydrochloride, L-asparagine monohydrate, L-cysteine hydrochloride monohydrate, L-cystine dihydrochloride, L-histidine monohydrochloride dihydrate, L-lysine monohydrochloride and hydroxyl L-proline, L-tyrosine disodium dehydrate. The exact form of the amino acids is not of importance for this invention, unless characteristics such as solubility, osmolarity, stability, purity are impaired. Typically and preferably, L-arginine is used as L-arginine×HCl, L-asparagine is used as L-asparagine× $H_2O$, L-cysteine is used as L-cysteine×HCl× $H_2O$, L-cystine is used as L-cystine×2 HCl, L-histidine is used as L-histidine×HCl× $H_2O$ and L-tyrosine is used as L-tyrosine×2 Na×2 $H_2O$, wherein each preferred amino acid form may be selected independent of the other or together or any combination thereof. Also encompassed are dipeptides comprising one or two of the relevant amino acids. For example L-glutamine is often added in the form of dipeptides, such as L-alanyl-L-glutamine to the cell culture medium for improved stability and reduced ammonium built up in storage or during long-term culture. This is also valid for L-glycine-containing dipeptides or other L-alanine-containing dipeptides, which are considered for calculation of the amino acid ratios.

The term "all amino acids in the medium" or "total amino acid content" as use herein refers to the sum of the "amino acids" as defined above in mM. In a dipeptide, each amino acid counts separately, thus 1 mM alanyl-glutamine is counted as 1 mM L-alanine and 1 mM L-glutamine (molar ratio 1:1). Likewise in L-cystine each cysteine counts separately, thus 1 mM L-cystine is counted as 2 mM L-cysteine (molar ratio 1:2). Typically the total amino acid content is about 5 to 20-fold, preferably about 7 to 15-fold and more preferably about 10-fold higher in the concentrated feed medium compared to the basal cell culture medium. The total amino acid content of the basal medium according to the invention may be about 25 to 150 mM, preferably about 30 to 130 mM, more preferably about 35 to 120 mM and even more preferably about 40 to 100 mM. The total amino acid content of the feed medium may be about 100 to 1000 mM, preferably about 200 to 900 mM, more preferably about 300 to 800 mM and even more preferably about 400 to 700 mM. Other amino acids that are not directly coded by the universal genetic code, such as L-ornithine, hydroxyl L-proline or metabolites thereof such as taurine may further be present in the basal cell culture medium or the feed medium, but these are not counted for the total amino acid content.

The term "amino acid ratio" as used herein refers to the ratio of the molar concentration of each amino acid related to the molar concentration of the reference amino acid. A molar ratio is calculated for every amino acid related to the reference amino acid (with the unit [mM/mM]). For the calculation of the amino acid ratios according to the present invention L-isoleucine is used as reference amino acid (although theoretically other amino acids can be used as reference amino acids such as phenylalanine or methionine). This may further be referred to as molar ratio relative to isoleucine (mM/mM). Typically, a reference amino acid can be easily measured with statistically low standard variations and is provided in similar concentration ranges in commonly used media.

The term "spent media amino acid ratio adjustment" means that amino acids are adjusted only based on spent media analysis but without consideration of cellular and metabolic demands and specific intracellular or extracellular rates. Thus, an amino acid analysis is performed for samples taken from the cell culture supernatant on various days and amino acids below a certain threshold are to be supplemented in the basal and feed medium.

The term "iron choline citrate" as used herein relates to the chemical compound ferric choline citrate falling under the CAS No. 1336-80-7 that forms an iron choline citrate complex. Common synonyms used are e.g. ferrocholinate citrate, ferric choline citrate, choline citrate, iron (III) choline citrate, choline ferric citrate, tricholine citrate, choline ferric citrate, 2-Hydroxyethyl-trimethyl-ammonium, 2-Hydroxypropane-1,2,3-tricarboxylate, boxylato(4-)ferrate(1-), ethanaminium, 2-hydroxy-n,n,n-trimethyl-,hydroxy(2-hydroxy-1,2,3-propanetricar. This compound may be added as an iron carrier to both the basal and the feed medium. Preferably iron choline citrate with a molar iron: choline: citrate ratio of 2:3:3 (ferric choline citrate, CAS-Number 1336-80-7, molecular weight Mw=991.5 g/mol+/−49.57 g/mol due to 5% crystal water content, iron complex with iron content of about 10.2-12.4%, molecule ratio for iron:choline:citrate of 2:3:3, molecule formula $C_{33}H_{57}Fe_2N_3O_{24}$, which is e.g. obtainable from Dr. Paul Lohmann GmbH KG) is used. However, other suitable iron choline citrate structures may be used at equimolar amounts based on the iron concentration, e.g. iron:choline:citrate at a ratio of 1:1:1, molecular weight of Mw=348.11 g/mol or (iron):choline:citrate at a ratio of (2):3:3, molecular weight of Mw=501.61 g/mol, $C_{21}H_{47}N_3O_{10}$ (sum formula without iron). Compared to the state of the art iron sources used in commercially available cell culture media such as iron phosphate, iron pyrophosphate or iron citrate, the usage of iron choline citrate contributes to significantly higher product titers at equimolar amounts.

The terms "polypeptide" or "protein" or "product" or "product protein" or "amino acid residue sequence" are used interchangeably. These terms "refer to polymers of amino acids of any length. These terms also include proteins that are post-translationally modified through reactions that include, but are not limited to glycosylation, glycation, acetylation, phosphorylation, oxidation, amidation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with similar or modified properties. Amino acid modifications can be prepared for example by performing site-specific mutagenesis or polymerase chain reaction mediated mutagenesis on its underlying nucleic acid sequence. The terms "polypeptide", "protein", "product" and "product protein" thus also include, for example, fusion proteins consisting of an immunoglobulin component (e.g. the Fc component) and a growth factor (e.g. an interleukin), antibodies or any antibody derived molecule formats or antibody fragments.

The term "protein of interest" or "product of interest" or "polypeptide of interest" includes proteins, polypeptides, fragments thereof, peptides, fusion proteins all of which can be expressed in the selected host cell. Typically, the protein of interest is a recombinant protein, i.e., a protein encoded by a recombinant DNA resulting from molecular cloning. Such proteins of interest can be antibodies, enzymes, cytokines, lymphokines, adhesion molecules, receptors and derivatives or fragments thereof, and any other polypeptides that can serve as agonists or antagonists and/or have therapeutic or diagnostic use or can be used as research reagent. Preferably the protein of interest is a secreted protein or protein fragment, more preferably an antibody or antibody fragment or an Fc-fusion protein. The "product of interest" may also be an antisense RNA, tRNA, rRNAs, other RNAs being part of riboproteins or other regulatory RNAs.

The term "gene of interest", "desired sequence", "polynucleotide of interest" or "desired gene" as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or a truncated gene, a fusion or tagged gene, and can be a cDNA, a genomic DNA, or a DNA fragment. It is generally understood that genomic DNA encoding for a polypeptide or RNA includes non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

Cell Culture Media and Amino Acid Ratios

The 20 standard amino acids that are encoded by the universal genetic code (L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine), play an essential role for protein synthesis since they provide the building blocks for both cellular proteins and for the protein of interest (e.g. monoclonal antibodies). Thus, amino acids interact manifold in the cellular metabolism. They are taken up from the cell culture medium in specific amounts, they are inter-converted within cellular metabolism, either directed into host cell proteins or into the product protein, excreted by a cell as by-product, and are connected at various points to the cellular metabolic catabolism and anabolism, e.g., between amino acid metabolism and citric acid cycle. In both basal and feed medium optimal composition, concentrations, and ratios of amino acids need to be provided for optimal nutritional supply throughout the life cycle (seeding, lag phase, exponential growth phase, transition phase, stationary phase, death phase characterized by significant decrease in cell viability) of a cell cultivation. However, the ratio of amino acids seems to be more important than the actual exact concentration of each individual amino acid.

Thus, in one aspect of the present invention a basal cell culture medium for culturing mammalian cells is provided comprising the following amino acids at a molar ratio relative to isoleucine (mM/mM) of: L-leucine/L-isoleucine of about 1.2-2.2; L-phenylalanine/L-isoleucine of about 0.5-0.9, L-tyrosine/L-isoleucine of about 1.5-2.7, L-threonine/I-isoleucine of about 1.0-1.9, and L-valine/L-isoleucine of about 1.0-1.9, wherein the basal cell culture medium has a total amino acid content of about 25 to 150 mM amino acids. In one embodiment the molar ratio relative to isoleucine (mM/mM) is: L-leucine/L-isoleucine of about 1.2-2.1, preferably about 1.3-1.8, more preferably about 1.5-1.8 and even more preferably about 1.7; L-phenylalanine/L-isoleucine of about 0.5-0-9, preferably about 0.6-0.9, more preferably about 0.6-0.8 and even more preferably about 0.7; L-tyrosine/L-isoleucine of about 1.6-2.6, preferably about 1.7-2.5, more preferably about 1.9-2.3 and even more preferably about 2.1; L-threonine/I-isoleucine of about 1.1-1.8, preferably about 1.2-1.8, more preferably about 1.3-1.6 and even more preferably about 1.5; and L-valine/L-isoleucine of about 1.1-1.9, preferably about 1.2-1-8, more preferably about 1.3-1.6 and even more preferably about 1.5. In certain embodiments the medium of the present invention further comprises L-lysine at a molar ratio relative to isoleucine of about 1.6-2.9, preferably of about 1.7-2.8, more preferably of about 1.8-2.7, more preferably of about 2.0 to 2.5 and even more preferably of about 2.2. In certain embodiments the basal medium of the present invention further comprises L-tryptophan at a molar ratio relative to isoleucine of about 0.3-0.5, preferably of about 0.3-0.5, more preferably of about 0.3-0.4, more preferably of about 0.3-0.4 and even more preferably of about 0.4; or L-proline at a molar ratio relative to isoleucine of about 1.6-3.0, preferably of about 1.7-2.8, more preferably of about 1.8-2.7, more preferably of about 2.0-2.5 and even more preferably of about 2.3, or L-methionine at a molar ratio relative to isoleucine of about 0.4-0.7, preferably of about 0.4-0.6, more preferably of about 0.4-0.6, more preferably of about 0.5-0.6 and even more preferably of about 0.5. In certain embodiments the molar ratios of L-tryptophan, L-proline and L-methionine relative to L-isoleucine are as defined above. The total amino acid content in the basal cell culture medium may be about 25-150 mM, preferably about 30-130 mM, more preferably about 35-120 mM, and even more preferably about 40-100 mM.

Preferably the amino acid ratios for L-leucine, L-phenylalanine, L-threonine, L-valine and L-tyrosine and optionally further for L-lysine, L-tryptophane, L-proline and/or L-methionine relative to L-isoleucine are within 30%, 25%, 20% or 10% of the ratios provided for basal medium 6.2 in table 2a.

More specific exemplary amino acid ratios of the basal cell culture medium (basal medium 6.2) of the present invention are provided in table A below in direct comparison to amino acid ratio in selected commercial basal cell culture media.

TABLE A

Amino acid ratios for each amino acid with reference isoleucine (Ile) for basal cell culture medium.

| Amino acid (AA) | Amino acid ratio (concentration AA/concentration reference AA isoleucine [mM/mM]) | | | |
|---|---|---|---|---|---|
| | DMEM_F12 | DMEM | HamsF12 | RPMI | Medium 6.2 |
| L-Alanine | 0.1 | — | 3.3 | — | — |
| L-Arginine | 1.7 | 0.5 | 33.3 | 2.5 | 2.1 |
| L-Asparagine | 0.1 | — | 3.3 | 0.9 | 1.8 |
| L-Aspartic Acid | 0.1 | — | 3.3 | 0.4 | 1.3 |
| L-Cysteine | 0.7 | 0.5 | 6.7 | 1.9 | 1.6 |
| L-Glutamic Acid | 0.1 | — | 3.3 | 0.4 | 0.9 |
| L-Glutamine | 14.1 | 7.3 | 194 | 55.7 | 46.4 |
| L-Glycine | 0.6 | 0.5 | 3.3 | 30.0 | 24.7 |
| L-Histidine | 0.4 | 0.3 | 3.3 | 0.3 | 0.9 |
| L-Isoleucine | 1.0 | 1.0 | 1.0 | 1.0 | 1.0 |
| L-Leucine | 1.1 | 1.0 | 3.3 | 1.0 | 1.7 |
| L-Lysine | 1.2 | 1.0 | 6.75 | 0.6 | 2.2 |
| L-Methionine | 0.3 | 0.3 | 1.0 | 0.3 | 0.5 |
| L-Phenylalanine | 0.5 | 0.5 | 1.0 | 0.2 | 0.7 |
| L-Proline | 0.4 | — | 10.0 | 0.5 | 2.3 |
| L-Serine | 0.6 | 0.5 | 3.3 | 0.8 | 2.1 |
| L-Threonine | 1.1 | 1.0 | 3.3 | 0.4 | 1.5 |
| L-Tryptophan | 0.1 | 0.1 | 0.3 | 0.1 | 0.5 |
| L-Tyrosine | 0.5 | 0.5 | 1.0 | 0.3 | 2.1 |
| L-Valine | 1.1 | 1.0 | 3.3 | 0.5 | 1.5 |

In another aspect of the invention a feed medium for culturing mammalian cells is provided comprising the following amino acids at a molar ratio relative to isoleucine (mM/mM) of: L-leucine/L-isoleucine of about 2.3-4.2, L-phenylalanine/L-isoleucine of about 0.6-1.1, L-threonine/I-isoleucine of about 1.3-2.4, and L-valine/L-isoleucine of about 1.1-2.0, wherein the feed medium has a total amino acid content of about 100 to 1000 mM. In one embodiment the molar ratio relative to isoleucine (mM/mM) is: L-leucine/L-isoleucine of about 2.4-4.0, preferably of about 2.6-3.9, more preferably of about 2.9-3.5 and even more preferably of about 3.2; L-phenylalanine/L-isoleucine of about 0.6-1.1, preferably of about 0.7-1.0, more preferably of about 0.8-0.9 and even more preferably of about 0.9; L-threonine/I-isoleucine of about 1.4-2.3, more preferably of about 1.5-2.2, more preferably of about 1.7-2.0 and even more preferably of about 1.8; and L-valine/L-isoleucine of about 1.2-2.0, preferably of about 1.3-1.9, more preferably of about 1.4-1.7 and more preferably of about 1.6.

In one embodiment the feed medium further comprises L-tyrosine at a molar ratio relative to isoleucine of about 0.6-1-1 and/or L-lysine at a molar ratio relative to isoleucine of about 1.1-2.1. Preferably tyrosine is present in the feed medium at a ratio of about 0.6-1.0, preferably of about 0.7-1.0, more preferably of about 0.7-0.9 and even more preferably of about 0.8. Preferably lysine is present in the feed medium at a ratio of about 1.2-2.0, preferably of about 1.3-1.9, more preferably of about 1.4-1.8 and even more preferably of about 1.6. Preferably the molar ratio of L-tyrosine and L-lysine are as defined above. In certain embodiments the feed medium of the present invention further comprises L-tryptophan at a molar ratio relative to isoleucine of about 0.3-0.6, preferably of about 0.3-0.6, more preferably of about 0.4-0.5, more preferably of about 0.4-0.5 and even more preferably of about 0.5; or L-proline at a molar ratio relative to isoleucine of about 0.9-1.8, preferably of about 1.0-1.7, more preferably of about 1.1-1.6, more preferably of about 1.2-1.5 and even more preferably of about 1.4, or L-methionine at a molar ratio relative to isoleucine of about 0.4-0.8, preferably of about 0.4-0.7, more preferably of about 0.5-0.7, more preferably of about 0.5-0.6 and even more preferably of about 0.6. In certain embodiments the molar ratios of L-tryptophan, L-proline and L-methionine relative to L-isoleucine are as defined above. The total amino acid content in the basal cell culture medium may be about 100-1000 mM, preferably about 200 to about 900, more preferably about 300 to about 800, and even more preferably about 400 to about 700 mM.

Preferably the amino acid ratios for L-leucine, L-phenylalanine, L-threonine and L-valine, and optionally further for L-tyrosine, L-lysine, L-tryptophane, L-proline and/or L-methionine relative to L-isoleucine are within 30%, 25%, 20% or 10% of the ratios provided for feed medium 6.2 in table 6.

More specific exemplary amino acid ratios of the feed medium (feed medium 6.2) of the present invention are provided in the table B below in direct comparison to amino acid ratio in selected commercial feed media.

TABLE B

Amino acid ratios for each compound with reference isoleucine (Ile) for feed medium.

| Amino acid (AA) | Amino acid ratio (concentration AA/concentration reference AA isoleucine [(mM)/(mM)]) | | |
| --- | --- | --- | --- |
| | Feed DMEM_F12 | Feed RPMI | Feed medium 6.2 |
| L-Alanine | 0.1 | — | — |
| L-Arginine | 1.7 | 2.5 | 1.0 |
| L-Asparagine | 0.1 | 0.9 | 3.2 |
| L-Aspartic Acid | 0.1 | 0.4 | 0.2 |
| L-Cysteine | 3.7 | 0.3 | 0.7 |
| L-Glutamic Acid | 0.1 | 0.4 | 0.3 |
| L-Glutamine | 11.0 | — | — |
| L-Glycine | 0.6 | 0.8 | 1.1 |
| L-Histidine | 0.4 | 0.3 | 0.6 |
| L-Isoleucine | 1.0 | 1.0 | 1.0 |
| L-Leucine | 1.1 | 1.0 | 3.2 |

TABLE B-continued

Amino acid ratios for each compound with reference isoleucine (Ile) for feed medium.

| Amino acid (AA) | Amino acid ratio (concentration AA/concentration reference AA isoleucine [(mM)/(mM)]) | | |
| --- | --- | --- | --- |
| | Feed DMEM_F12 | Feed RPMI | Feed medium 6.2 |
| L-Lysine | 1.2 | 0.6 | 1.6 |
| L-Methionine | 0.3 | 0.3 | 0.6 |
| L-Phenylalanine | 0.5 | 0.2 | 0.9 |
| L-Proline | 0.4 | 0.5 | 1.4 |
| L-Serine | 0.6 | 0.8 | 3.2 |
| L-Threonine | 1.1 | 0.4 | 1.8 |
| L-Tryptophan | 0.1 | 0.1 | 0.5 |
| L-Tyrosine | 0.3 | 0.4 | 0.8 |
| L-Valine | 1.1 | 0.5 | 1.6 |

The feed medium is added as a concentrated feed medium to the basal cell culture medium or the culture medium. For example, the feed medium may be added at about 10-50 ml/L/day, preferably at about 15 to 45 ml/L/day, more preferably at about 20-40 ml/L/day and even more preferably at about 30 ml/L/day based on the culture starting volume (CSV). The rate (volume/day) for addition of the feed medium to the cell culture in ml/L/day (volume in ml added per liter of culture starting volume in the vessel per day) is to be understood as an average rate over the feeding period and the added volume may vary between individual additions during the feeding period. Also feeding may be stopped about 1 to 3 days prior to termination of the culture and/or harvest. It is preferable to add a small volume to avoid dilution of other nutrients in the cell culture and to maintain the culture volume as constant as possible. The feed medium may be added continuously, several times a day, daily or every second day. Preferably, said feed medium is added starting on day 0, day 1 or day 2 every day or every second day.

The basal cell culture medium and/or the feed medium of the invention are serum-free and preferably chemically defined or chemically defined and protein-free. Further the basal cell culture medium and the feed medium of the invention are suitable for culturing mammalian cells, i.e., they are a basal mammalian cell culture medium and a mammalian feed medium, respectively. The basal cell culture medium and the feed medium of the invention is suitable for culturing all kinds of mammalian cells, such as rodent or human cells, wherein rodent cells are preferred. More preferably the mammalian cell is a Chinese hamster ovary cell (CHO), such as a CHO-K1 cell, a CHO-DG44 cell, a DuxB11 cell or a CHO GS deficient cell, most preferably the cell is a CHO-DG44 cell or a CHO GS deficient cell.

The basal cell culture medium comprising the amino acid ratio of the invention may further comprise the iron choline citrate at a concentration as described for the basal cell culture medium herein below. Similarly, the feed medium comprising the amino acid ratio of the invention may further comprise the iron choline citrate at a concentration as described for the feed medium herein below.

Culture Media and Iron Carrier

In mammalian cell culture, iron is required as a trace element. In vivo, iron is bound primarily by ferritin and transferrin in serum. A typical iron source in cell culture media is transferrin. In advanced serum-free or even protein-free mammalian cell culture media, several aspects related to iron need to be solved, such as the identification of a suitable iron carrier, the poor bioavailability of iron, the identification of adequate physiological concentration ranges (with minimal/no negative effects on e.g. cell viability due to the presence of harmful free radicals in vitro with respect to the underlying toxicity of ferric compounds), the complex binding behavior (iron can bind to a plurality of substances within a medium formulation and thereby can easily become biologically unavailable for the cell culture), oxidation status, and optimal cell culture performance (e.g. titer).

In the present invention the chemical compound iron choline citrate is provided as a novel iron-carrier in mammalian cell culture with improved characteristics compared to established iron-carriers used in cell cultivation.

Thus, in another aspect the invention provides a basal cell culture medium for culturing mammalian cells comprising iron choline citrate at a concentration of about 0.1 to 5.0 mM, about 0.2 to 2.0 mM, about 0.2 to 1.0 mM or about 0.4 to 1.0 mM.

In yet another aspect, the invention provides a feed medium comprising iron choline citrate at a concentration of about 0.4 to 5.0 mM, about 0.4 to 1.0 mM, or about 0.5 to 1 mM, preferably about 0.5 to 0.6 mM.

The concentrations of iron choline citrate in the basal medium and the feed medium are based on iron choline citrate with a molar iron: choline: citrate ratio of 2:3:3 (ferric choline citrate, CAS-Number 1336-80-7, molecular weight Mw=991,5 g/mol+/−49.57 g/mol due to 5% crystal water content, iron complex with iron content of about 10.2-12.4%, molecule ratio for iron: choline: citrate of 2:3:3, molecule formula $C_{33}H_{57}Fe_2N_3O_{24}$). However, other iron choline citrate structures are encompassed by the invention and may be used at equimolar amounts based on the iron concentration, e.g. iron: choline: citrate at a ratio of 1:1:1, molecular weight of Mw=348.11 g/mol. This means for example that 1 mM iron choline citrate with a molar iron: choline: citrate ratio of 2:3:3 equates to 2 mM iron choline citrate with a molar iron:choline:citrate ratio of 1:1:1.

The use of iron choline citrate as iron carrier results in increased product titers. Additionally, compared to other iron sources that are established as iron carriers such as iron citrate, the novel iron carrier iron choline citrate is typically chemically characterized by a higher purity compared to iron citrate. The higher potential lot-to-lot variability of established iron carriers such as iron citrate can cause negative effects in manufacturing of biopharmaceuticals (e.g. reproducibility in manufacturing is negatively affected). Iron choline citrate can be used in both basal and/or feed medium, preferably iron choline citrate is added to both the basal medium and the feed medium. Compared to other iron sources used in cell culture media such as iron (III) phosphate or iron (III) pyrophosphate, the use of iron choline citrate leads to an improved culture performance, e.g., significantly higher product titers. The basal cell culture medium comprising iron choline citrate according to the invention may further comprise the novel amino acid ratio of the basal medium according to the invention, as described above. Similarly, the feed medium comprising the iron choline citrate according to the invention may further comprise the novel amino acid ratio of the feed medium according to the invention as described above.

The basal cell culture medium and/or the feed medium of the invention are serum-free, preferably chemically defined or chemically defined and protein-free. Further the basal cell culture medium and the feed medium of the invention are suitable for culturing mammalian cells, i.e., they are a basal mammalian cell culture medium and a mammalian feed medium, respectively. The basal cell culture medium and the feed medium of the invention is suitable for culturing all kinds of mammalian cells, such as rodent or human cells, wherein rodent cells are preferred. More preferably the mammalian cell is a Chinese hamster ovary cell (CHO), such as a CHO-K1 cell, a CHO-DG44 cell, a DuxB11 cell or a CHO GS deficient cell, most preferably the cell is a CHO-DG44 cell or a CHO GS deficient cell.

Culture Media and Other Components

A cell culture medium to culture mammalian cells may further comprise essential nutrients and components such as vitamins, trace elements, salts, bulk salts, lipids or lipid precursors and carbohydrates in a preferably buffered medium. Also growth factors may be added to the basal cell culture medium or the feed medium, e.g., recombinant insulin-like growth factor (IGF) or recombinant insulin.

Non-limiting examples for suitable vitamins are biotin (B7), calcium pantothenate, cyanocobalamin (B12), folic acid, myoinositol, niacinamid (B3), pyridoxal hydrochloride, pyridoxine hydrochloride, riboflavin (B2) and/or thiamine (B1). Non-limiting examples for trace elements are ammonium molybdate, ammonium vanadate, cupric sulfate, nickel sulfate, sodium selenite, sodium silicate, and zinc sulfate and/or zinc chloride. Non-limiting examples of lipid precursors are choline chloride, ethanolamine, glycerol, inositol, linoleic acid, fatty acids, phospholipids or cholesterol-related compounds.

Further, salts may be, without being limited thereto, calcium chloride, calcium nitrate, magnesium chloride, magnesium sulfate, potassium chloride and/or sodium chloride. One function of the salt is to adjust the osmolarity in the medium. Preferably the osmolarity of a basal cell culture medium does not go beyond an optimal range of typically between 280-350 mOsmo/kg. Typically the osmolarity of a concentrated feed medium is <2000 mOsmo/kg, preferably <1500 mOsmo/kg, more preferably <1000 mOsmo/kg. The osmolarity of the feed medium may be higher, but should not increase the osmolarity in the cell culture upon addition beyond the optimal range of 270-550 mOsmo/kg, preferably of 280-450 mOsmo/kg, more preferably of 280-350 mOsmo/kg.

Preferably, the feed medium of the present invention in any of its embodiments has reduced or low salt content. A reduced or low salt content means, e.g., a total salt concentration of about 100 mM or less, preferably of about 50 mM or less (e.g. a feed medium without sodium chloride, and a reduced concentration of potassium chloride). A reduced low salt content in the feed medium of the present invention is especially preferred when the feed medium is combined with the basal cell culture medium of the present invention for use as regular growth medium.

The most important contributors to osmolarity are sodium ions, chloride ions, and bicarbonate as well as glucose and other carbon sources e.g. amino acids. For the medium developer it is a challenge to create a high concentrated nutrient mixture and a powder formulation for manufacturing that meets the following requirements: preferably a x-fold concentrate of basal medium composition (positive impact for supply chain management and regulatory aspects), provide essential nutrients and nutrients that cannot be synthesized by the cell itself in adequate amounts (preferably in as rational-balanced composition), overcome solubility aspects for feed concentrates, remove bulk salts due to osmolarity reasons, avoid toxic ranges, design a powder formulation that requires an carbon carrier for galenic reasons. Furthermore, for a common fed-batch process the feed medium needs to be concentrated to minimize the culture volume over the cultivation period. The size of the bioreactor may actually cause feeding constrains that allow only total feed dosages of approximately 30% (25-35%) of the culture starting volume.

Carbohydrates may be, but are not limited to glucose, mannose, galactose, fructose, sucrose or glucosamine etc. These carbohydrates can be added directly to the basal cell culture medium and/or the feed medium or may be added separately to the cell culture. Other energy sources include, but are not limited to sodium pyruvate.

Mammalian cells should be cultured at a neutral pH, such as from about pH 6.5 to about pH 7.5, preferably from about pH 6.6 to about pH 7.3, more preferred at a pH of about 7. Hence buffering agents should be added to the basal cell culture medium. For the feed medium the pH may be slightly outside said range, as long as the addition of the feed medium does not bring the pH of the cell culture outside this range, since the feed medium is added as a concentrate. Preferred ranges for the pH in a feed medium are from about 6 to about 8. Suitable buffering agents include, but are not limiting to Hepes, phosphate buffers (e.g., potassium phosphate monobasic and potassium phosphate dibasic and/or sodium phosphate dibase anhydrate and sodium phosphate monobase), phenol red, sodium bicarbonate and/or sodium hydrogen carbonate.

Generally, the feed medium comprises nutrients that are consumed during cell culture, such as amino acids and carbohydrates, while salts and buffers are of less importance. Some salts may therefore be omitted entirely from a feed medium.

Cell Culture Performance

The basal cell culture medium and/or the feed medium of the present invention or the cell culture medium platform comprising the chemically defined basal medium and the chemically defined feed medium of the invention result in improved cell culture performance. The term "improved cell culture performance" as used herein comprises, e.g., significantly improved product titers, improved cell growth (e.g. viable cell counts, cell viability), and favorable phenotypic behavior of a cell culture process such as reduced overflow metabolism of unwanted and toxic by-products (e.g. reduced lactate formation). It also contributes to reduced osmolarity levels in a cell cultivation process.

The basal cell culture medium and/or the feed medium of the present invention meet the cell specific requirements and metabolic needs of a mammalian cell culture during the time course of cell cultivation. In other words it meets (i) the cell specific needs of a mammalian cell, (ii) in a cell cultivation system, (iii) throughout the lifecycle of a cultivation run (which is about 10-20 days). Mammalian cells in culture have different nutritional requirements in different phases of a cell culture process. Yet, ideally, only one optimal basal medium and only one (or quite few) optimal feed medium/media need to be designed to enable the design of robust, safe, and efficient bioprocesses. The basal medium and/or feed medium provided herein fulfill this need.

The basal cell culture medium and/or the feed medium of the present invention have improved cell culture performance. Non limiting examples for improved cell culture performance are increase of product titers, improved viable cell concentrations and/or cell viabilities. Also the cell expansion may be improved, which is needed for the inoculation train in a scale-up procedure. For example, cultivation scales are stepwise increased from thaw of a cell bank (mL scale) to the production scale (>10.000 L scale). The better the growth in each N-x stage is (with N-stage meaning the final production scale and N-x meaning the cell expansion stages before final production stage usually in batch mode), the faster and the better each transfer to the next stage can occur. Specifically, better cell growth and higher viable cell concentrations allow that N-x cultivations can be performed with reduced run times (hence faster). Better cell growth and higher viable cell concentrations also result in improved transfers resulting in an overall improved performance. For example, when a certain N-x stage should be inoculated with a certain seeding cell density and the viable cell concentration is high, a relatively low volume of cell culture needs to be transferred from one stage to the next (transfer of inoculum volume per CSV is defined as spit ratio, usually 1:5 to 1:20 is common). This means that at the same time only a reduced volume of "used" cell culture medium is transferred from one stage to the next and a maximal volume of "new" media can be added to the next stage (constant overall cultivation volumes). This also results in improved overall cell culture performance in the final N-stage (e.g. increased product titer). With the novel basal cell culture medium and feed medium provided in the present invention all of these stages are improved. The positive effects of the novel iron carrier iron choline citrate and/or the novel amino acid ratios are not limited to basal medium and feed medium in the final production stage. It is also shown that the positive effects of the media platform apply to the N-x stages, in particular for the amino acid ratios. These positive effects are also maintained in the case of media modifications in the N-x stages. For example, typically MTX (methotrexate) is provided in early stages of the inoculation train in order to maintain the selection pressure in mammalian cell culture using recombinant cell lines such as CHO cell lines, preferably CHO-DG44 cell lines. Also in such examples, the application of the basal cell culture medium and/or feed medium or the media platform of the invention results in significantly improved viable cell concentrations.

Cell Culture/Addition of Feed Medium

The addition of a nutrient concentrate named "feed medium" is required for the standard fed-batch application in contrast to the common batch fermentation, where no concentrated feed medium is added to the culture during the entire cultivation. In contrast to a batch application, it is well known that the cell culture performance e.g. maximal viable cell count, final product titer, metabolic waste accumulation is significantly improved in a fed-batch process due to the replenishment of nutrients, vitamins, salts and other components. Typically the maximal amount of feed solution added to the culture during the cultivation time depends on technical, but also on metabolism-driven aspects: the maximal volume of the bioreactor constrains the total feed volume to be added, whereas a non-technical feed dosage is applied to meet the real cellular nutrient demand at any time during the cultivation. Furthermore, dependent on the cell line and process mode, the feed addition can be added continuously e.g. in small scale 2-80 L (development, less work intense) with a constant feed rate of, e.g., 5-60 ml feed/L/d or with a non-continuous (large scale manufacturing, more work intense) approach e.g. in 2000-10.000 L large scale to minimize the risk of contamination. Typical intervals for feed additions during an e.g. 11-day fed-batch cultivation can vary between several times a day, daily or every 2-4 days, and often depend on the actual nutrient level, growth phase, culture conditions such as pH or the nutrient demand of the culture.

Lactate/Carbon Dioxide/Glucose

In most cell cultures a non-ideal nutrient combustion for major carbon can be determined due to an overflow-metabolism. This means, that the major carbon source glucose is utilized ineffectively and by this contributes to an increase of organic acids e.g. lactic acid. The increased level of lactic acid can contribute to a pH drop below 6.65 and this would negatively affect the buffer capacity of the culture medium and thus the culture viability. For such reason, the $CO_2$ concentration in the culture atmosphere is reduced at the beginning of the exponential growth phase in order to minimize the acid level in the culture medium.

Cell Lines and Cell Culture

The basal cell culture medium and/or the feed medium or the medium platform of the present invention can be applied to all mammalian cell lines. However, the media of the present invention may further be suitable for other eukaryotic cells, such as yeast, plant or insect cells. The mammalian cell according to the invention may be oocytes, embryonic stem cells, hematopoietic stem cells or any type of differentiated cells. Preferably, the mammalian cell is a human, simian, murine, goat, bovine, sheep, pig cell or rodent cell line such as rat, rabbit or hamster. The mammalian cell may be an isolated primary cell or a cell line. Preferred cell lines or "host cells" for the production of recombinant biopharmaceuticals are human, monkey, or rodent cell lines (mice, rat or hamster). Preferred human cells are PER.C6 or HEK 293 cells.

More preferred are rodent cells, such as hamster cells, preferably BHK21, BHK TK-, Chinese Hamster ovary cells (CHO), CHO-K1, CHO-DXB11 (also referred to as CHO-DUKX or DuxB11), CHO-DUKX B1, CHO-S, CHO-DG44 and CHO glutamine synthetase (GS) deficient cells or the derivatives/progenies of any of such cell lines. Particularly preferred are CHO-DG44, CHO-DUKX, CHO-K1, CHO-S, CHO-DG44 GS deficient cell lines and BHK21, and even more preferred CHO-DG44 cells, CHO GS deficient cells (such as a CHO-K1 GS deficient cell) and CHO-DUKX cells. Furthermore, murine myeloma cells, preferably NS0 and Sp2/0 cells or the derivatives/progenies of any of such cell lines are also known as production cell lines for biopharmaceutical proteins.

All cells and cell lines may be used in all kind of cell cultivations, e.g., ranging from plastic microtiter plates (nL to mL scale) to industrial scale stainless steel bioreactors (L to kL scale), they also include any type of disposable system and all kinds of process control strategies from non-controlled systems to fully controlled systems comprising e.g. advanced online monitoring and advanced control strategies. Suitable culture conditions for mammalian cells are known in the art. Mammalian cells may be for example cultured in suspension or attached to a solid surface.

Non-limiting examples of mammalian cells, which can be used with the media of the present invention are summarized in Table C.

TABLE C

Suitable exemplary mammalian production cell lines

| CELL LINE | REFERENCE NUMBER |
|---|---|
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-DUKX (= CHO duk⁻, CHO/dhfr⁻) | ATCC CRL-9096 |

TABLE C-continued

Suitable exemplary mammalian production cell lines

| CELL LINE | REFERENCE NUMBER |
|---|---|
| CHO-DUKX B11 | ATCC CRL-9010 |
| CHO-DG44 | Urlaub et al., Cell 33 (2), 405-412, 1983; Life Technologies A1097101 |
| CHO Pro-5 | ATCC CRL-1781 |
| CHO-S | Life Technologies A1136401; CHO-S is derived from CHO variant Tobey et al. 1962 |
| Lec13 | Stanley P. et al, Ann. Rev. Genetics 18, 525-552, 1984 |
| V79 | ATCC CCC-93 |
| HEK 293 | ATCC CRL-1573 |
| COS-7 | ATCC CRL-1651 |
| HuNS1 | ATCC CRL-8644 |
| Per.C6 | Fallaux, F. J. et al, Human Gene Therapy 9 (13), 1909-1917, 1998 |
| CHO-K1 | ATCC CCL-61, ECACC 85051005 |
| CHO-K1/SF | ECACC 93061607 |
| CHO-K1 GS | glutamine synthetase (GS) deficient cells derived from CHO-K1 |
| CHOZN GS | GS deficient cells derived from CHO-K1 (SAFC ECACC 85051005) |

Said production cells are cultivated preferentially under conditions that allow the cells to proliferate. Furthermore, said production cells are cultivated preferentially under conditions, which are favorable for the expression of the desired gene(s) and/or the protein of interest. The protein of interest is than isolated from the cells and/or the cell culture supernatant. Preferably the protein of interest is recovered from the culture medium as a secreted polypeptide, or it can be recovered from host cell lysates if expressed without a secretory signal.

Typically, it is necessary to purify the protein of interest from other recombinant proteins, host cell proteins and contaminants in a way that substantially homogenous preparations of the protein of interest are obtained. As a first step cells and/or particulate cell debris may be removed from the culture medium or lysate. Typically, the product of interest is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin such as DEAE.

Use of the Culture Medium

The basal cell culture medium or the feed medium of the invention can be used as a growth medium, as an inoculum medium, as medium for cell expansion or for cell line development, including transfection, amplification or both. Further, the basal cell culture medium or the feed medium may be used, preferably in combination, for producing a protein of interest from a mammalian cell expressing said protein of interest.

Specifically the basal medium and the feed medium of the invention may be used in a method of culturing a mammalian cell comprising the following steps: a) providing mammalian cells, b) culturing the cells in the basal cell culture medium of the invention, and c) optionally adding the feed medium of the invention to the basal cell culture medium; wherein the cells are cultured under conditions that allow the cells to proliferate. Preferably the feed medium is also used in said method.

The basal medium and the feed medium of the invention may further be used in a method of producing a protein of interest comprising the following steps: a) providing mammalian cells comprising a gene of interest encoding the protein of interest, b) culturing the cells in the basal cell culture medium of the invention, and c) optionally adding the feed medium of the invention to the basal cell culture medium, and d) optionally separating and/or isolating and/or purifying said protein of interest from the cell culture; wherein the cells are cultured under conditions that allow expression of the protein of interest. Preferably the feed medium is used in said method. The feed medium may be added to the cells cultured in the basal cell culture medium at about 10-50 ml/L/day, preferably at about 15-45 ml/L/day, more preferably at about 20-40 ml/L/day and more preferably at about 30 ml/L/day based on the culture starting volume (CSV), wherein the medium may be added continuously or as a bolus several times a day, two times a day, once per day, every second day or every third day. Preferably the feed medium is added starting on day 0, 1, 2 or 3. The rate (volume/day) for addition of the feed medium to the cell culture in ml/L/day (feed volume in ml added per liter of culture starting volume in the vessel per day) is to be understood as an average rate over the feeding period and the added volume may vary between individual additions during the feeding period. Also, feeding may be stopped about 1 to 3 days prior to termination of the culture and/or harvest.

Separating the protein of interest from the cell culture can be done by e.g., centrifugation, filtration or any other method known in the art for separating the supernatant comprising the protein from cells or cell debris. This may include lysis if the protein is produced intracellularly. Purification of the protein of interest from the cell culture means isolating one or a few proteins from a complex mixture, such as a cell culture supernatant or a lysate by methods known in the art, such as precipitation, chromatography or gel electrophoresis.

The basal medium and the feed medium of the invention may be used in a large-scale cell culture, preferably a cell culture of 100 L or more, more preferably of 1000 L or more or even more preferably of 10000 L or more.

The protein of interest may be an antibody, an enzyme, a cytokine, a lymphokine, an adhesion molecule, a receptor, or derivatives or fragments thereof, and any other polypeptide that can serve as agonist or antagonist and/or have therapeutic or diagnostic use or can be used as research reagent. The protein of interest may be for example an antibody, such as Rituximab, or an Fc-fusion protein. Preferably the antibody is a monoclonal IgG1 antibody with a heavy and light chain having the amino acid sequence of SEQ ID NO: 1 and SEQ ID NO:2 or with a heavy and light chain having the amino acid sequence of SEQ ID NO: 3 and SEQ ID NO:4. The Fc-fusion protein preferably has the amino acid sequence of SEQ ID NO: 5.

Proteins of interest may also be proteins/polypeptides, which are used to change the properties of host cells within the scope of so-called "Cell Engineering", such as e.g. anti-apoptotic proteins, chaperones, metabolic enzymes, glycosylation enzymes and the derivatives or fragments thereof, but are not restricted thereto.

Especially, desired proteins/polypeptides or proteins of interest are without being limited thereto, e.g., insulin, insulin-like growth factor (IGF1), hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1, VEGF and nanobodies. Also included is the production of erythropoietin or any other hormone growth factors and any other polypeptides that can serve as agonists or antagonists and/or have therapeutic or diagnostic use. The method according to the invention can also be advantageously used for production of antibodies, such as monoclonal, polyclonal, multispecific and single chain antibodies, or fragments derived thereof, e.g. Fab, Fab', F(ab')2, Fc and Fc'-fragments, heavy and light immunoglobulin chains and their constant, variable or hypervariable region as well as Fv- and Fd-fragments.

The term "antibody", "antibodies", or "immunoglobulin(s)" as used herein relates to proteins selected from among the globulins, which are formed as a reaction of the host organism to a foreign substance (=antigen) from differentiated B-lymphocytes (plasma cells). They serve to defend specifically against these foreign substances. There are various classes of immunoglobulins: IgA, IgD, IgE, IgG, IgM, IgY, IgW. Preferably the antibody is an IgG antibody, more preferably an IgG1 antibody. The terms immunoglobulin and antibody are used interchangeably. Antibody includes a polyclonal, monoclonal, monospecific, bi-specific, multi-specific, a single chain antibody, an antigen-binding fragment of an antibody (e.g., an Fab or F(ab')2 fragment), a disulfide-linked Fv, etc. Antibodies can be of any species and include chimeric and humanized antibodies. "Chimeric" antibodies are molecules in which antibody domains or regions are derived from different species. For example the variable region of heavy and light chain can be derived from rat or mouse antibody and the constant regions from a human antibody. In "humanized" antibodies only minimal sequences are derived from a non-human species. Often only the CDR amino acid residues of a human antibody are replaced with the CDR amino acid residues of a non-human species such as mouse, rat, rabbit or llama. Sometimes a few key framework amino acid residues with impact on antigen binding specificity and affinity are also replaced by non-human amino acid residues. Antibodies may be produced through chemical synthesis, via recombinant or transgenic means, via cell (e.g., hybridoma) culture, or by other means.

Immunoglobulins are tetrameric polypeptides composed of two pairs of a heterodimer each formed by a heavy and light chain. Stabilization of both the heterodimers as well as the tetrameric polypeptide structure occurs via interchain disulfide bridges. Each chain is composed of structural domains called "immunoglobulin domains" or "immunoglobulin regions" whereby the terms "domain" or "region" are used interchangeably. Each domain contains about 70-110 amino acids and forms a compact three-dimensional structure. Both heavy and light chain contain at their N-terminal end a "variable domain" or "variable region" with less conserved sequences which is responsible for antigen recognition and binding. The variable region of the light chain is also referred to as "VL" and the variable region of the heavy chain as "VH".

The term "Fab fragment(s) "(Fragment antigen-binding=Fab) or "Fab" consist of the variable regions of both antibody heavy and light chains (VH and VL) which are held together by the adjacent constant regions (CH1 and CL). These may be formed by protease digestion, e.g. with papain, from conventional antibodies, but similar Fab fragments may also be produced in the meantime by genetic engineering. Further antibody fragments include "F(ab')2 fragments" or "F(ab')2", which may be prepared by proteolytic cleaving with pepsin or by genetic engineering in which both Fab arms of an antibody are still linked via inter-heavy chain disulfide bridges located within the hinge region.

The immunoglobulin fragments composed of the CH2 and CH3 domains of the antibody heavy chain are called "Fc fragments", "Fc region" or "Fc" because of their crystallization propensity (Fc=fragment crystallizable). These may be formed by protease digestion, e.g. with papain or pepsin from conventional antibodies but may also be produced by genetic engineering. The N-terminal part of the Fc fragment might vary depending on how many amino acids of the hinge region are still present.

The term "Fc-fusion protein" describes polypeptides which contain as a fusion partner a natural or modified (e.g. substitutions, deletions, insertions) Fc region of an immunoglobulin. Fc fusion proteins can be either naturally occurring proteins (e.g. antibodies) or engineered recombinant proteins (e.g. TNF receptor-Fc fusion protein or a VH region fused to an Fc region). The Fc-fusion proteins can exist either as monomers or as multimers whereby polypeptides can have identical or different sequences, might contain linker sequences between the two fusion partners and/or part of the hinge region or modified hinge regions or the polypeptide is fused directly to the CH2 domain.

Using genetic engineering methods it is possible to produce shortened antibody fragments which consist only of the variable regions of the heavy (VH) and of the light chain (VL). These are referred to as "Fv fragments" (Fragment variable=fragment of the variable part) or "Fv". Since these Fv-fragments lack the covalent bonding of the two chains by the cysteines of the constant chains, the Fv fragments are often stabilized. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a "single-chain-Fv" or "scFv". Examples of scFv-antibody proteins of this kind are known from the prior art. In addition, more than one VH and/or VL region can be linked together.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucine-zipper domains. However, there are also strategies in which the interaction between the VH/VL regions of the scFv is used for the multimerisation (e.g. dia-, tri- and pentabodies). By diabody the skilled person means a bivalent homodimeric scFv derivative. The shortening of the linker in a scFv molecule to 5-10 amino acids leads to the formation of homodimers in which an inter-chain VH/VL-superimposition takes place. Diabodies may additionally be stabilized by the incorporation of disulphide bridges. Examples of diabody-antibody proteins are known from the prior art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a linker region. Examples of minibody-antibody proteins are known from the prior art.

By triabody the skilled person means a: trivalent homotrimeric scFv derivative. ScFv derivatives wherein VH-VL is fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures. In a preferred embodiment of the present invention, the gene of interest is encoded for any of those desired polypeptides mentioned above, preferably for a monoclonal antibody, a derivative or fragment thereof.

The term "antibody derived molecule(s)" is used interchangeably with "antibody derived fragments" or "antibody fragments" and refers to polpypeptides which contain only part(s) of one or more antibody domain(s) or region(s) and/or complete domain(s) or region(s). The antibody fragments can be either a) forming a molecule on their own, b) linked with each other in different combinations, c) fused to non-antibody sequences, d) fused or linked to non-polypeptide (e.g. radionucleotides) or d) any combination of the above. These polypeptides can exist either as monomers or as multimers whereby polypeptides can have identical or different sequences.

EXAMPLES

Materials and Methods

Cell Line

CHO cell lines (CHO-DG44) were adapted to serum-free media conditions and further transfected with DNA to produce recombinant products such as monoclonal antibodies, fusion proteins or bi/multi-specific proteins that are relevant for industrial manufacturing. Specifically, two proprietary BI HEX (Boehringer-Ingelheim High Expression) CHO-DG44 derived CHO cell lines that were independently adapted to serum-free media (named HEX I and HEX II) expressing different IgG constructs were used. These cells are DHFR$^-$ (dihydrofolate-reductase) deficient and methotrexate is used as selection marker. If not otherwise stated the cells used in the experiments are CHO-DG44 (HEX II) cells expressing Rituximab as recombinant protein with a heavy chain having the amino acid sequence of SEQ ID NO: 1 and a light chain having the sequence of SEQ ID NO: 2, which is secreted into the culture medium. This cell line is referred to as CHO2, CHO-DG44 Rituximab or CHO2 (CHO-DG44) Rituximab in the following.

Analytical Methods

Cell concentrations and cell viabilities were determined by the trypan blue exclusion method using a CEDEX (Type 5.00, version 2.2) automated cell analyzer (Roche Innovatis, Bielefeld, Germany). The concentrations of produced recombinant proteins in the medium, such as IgG antibodies were quantified by a Konelab 60i (Thermo Scientific, Dreieich, Germany) analyzer based on photometrical methods or by the use of a HPLC method. The Konelab 60i instrument was also used for the quantification of metabolites such as glucose, lactic acid (lactate), glutamine, glutamate, and ammonium in the cell culture supernatants. Amino acid concentrations were determined by use of a GC 6890N/FID gas chromatograph (Agilent Technologies GmbH & Co.KG, Waldbronn, Germany). Amino acid analysis was performed by the EZ-faast protocol from Phenomenex (Aschaffenburg, Germany). Osmolarity profiles were analyzed by an osmomat auto device (Gonotec GmbH, Berlin, Germany). This method is based on the cryoscopic freezing point of a particular solution, which is proportional to the amount of dissolved particles. Dissolved carbon dioxide $pCO_2$, dissolved oxygen $pO_2$ and pH were determined on a daily basis with a Rapidlab 248/348 instrument (Siemens Healthcare Diagnostics GmbH, Eschborn, Germany). These instruments and the required methods are well known in the art and used for process monitoring and control in biopharmaceutical process development and manufacturing.

Shake Flask Cultivation

Shake flask (Corning B.V. Life Sciences, Amsterdam, Netherlands) experiments were generally performed in small scale, with a working volume in the range of 60-500 ml in batch mode (no feed addition during cultivation) or in fed-batch mode (with a standard feed rate of 30 ml/L/d nutrient feed addition during cultivation). Viable cell concentration at inoculation was typically set to $0.3 \times 10^6$ cells/ml in every experiment. The shake flasks cultivations were derived from the same inoculum pre-culture (thawing, expansion of cells in a seed train, with respect to cell age) to ensure comparability between different experimental settings if required. For cell cultivation a standard shake flask incubator (Infors AG, Bottmingen, Switzerland) was used at a shaking rate of 120 rpm, a temperature set point of 37° C., and humidity was set to 70%. The analytical methods as described above were used to measure the standard process parameter on a daily basis, which are total and viable cell count, cell viability, metabolite concentrations and other relevant cell culture parameters such as dissolved oxygen $pO_2$ (DO), dissolved carbon dioxide $PCO_2$ (DCO) content or pH. This was done routinely throughout the cultivation to monitor and control the cultivation conditions for each experimental setup. In fed batch experiments, a concentrated feed solution was added in fed-batch experiments as a bolus addition of 1.8 ml feed per day to a culture starting volume of 60 ml (corresponding to 30 ml/L/d nutrient feed rate based on the culture starting volume), starting on day 2, in an uncontrolled shake flasks system.

Batch and Fed-Batch Mode

For the production of recombinant proteins and antibodies, typically fed-batch processes are used in the final production stage, while batch cultivations are mainly performed in the cell expansion stages prior to the final production stage. A series of batch cultures is referred to as seed train during cell expansion, meaning that cells are transferred in each expansion step into cultivations vessels with larger cultivation volumes. Batch processes in the final production stage do generally not result in high productivity and are therefore rarely used for manufacturing recombinant proteins. In fed-batch processes concentrated feed medium is added during cultivation to compensate for replenishment of nutrients with fresh medium. These processes achieve a higher productivity and are therefore used predominantly in recombinant protein production. In contrast to the batch mode, a replenishment of nutrients by adding concentrated feed medium also reduces inhibition of cell growth by unwanted metabolic by-products such as lactate or ammonium. Typically fed-batch processes are started at a volume much lower than the maximal capacity of a stirred tank so that concentrated nutrient solutions can be added over the bioreactor cultivation time.

Bioreactor Cultivation

The bioreactor experiments were performed in a controlled 2-L system (Boehringer-Ingelheim proprietary multifermenter system) with a start volume of 1.8 L or in a controlled 48-mini-bioreactor system with a starting volume of maximal 15 ml. The fully controlled bioreactors were performed in batch or fed-batch mode. In fed-batch a concentrated feeding solution was continuously added by a feed pump from cultivation usually from day 1-3 onwards with a feeding rate of 30 ml/L/d (based on the culture starting volume). The seeding density was set to $0.3 \times 10^6$ cells/ml similar to the shake flasks system. The expansion of cells over a longer time frame followed a standard seed train protocol for cell growth and culture splits in order to ensure phenotypic stability. This procedure ensures comparability between different experimental settings at different time points. For a typical bioreactor cultivation, a standard process format consists of a pH range from 7.10-6.95 (+/−0.25) including a pH shift from day 3, a DO set point of 30-60% (air saturation), a constant stirring rate of 140 rpm (4-blade rushton turbine stirrer), and a temperature set point of 36.5-37° C. The analytical methods as described above were used to determine the major culture parameters such as cell count, cell viability, and major carbon metabolite concentrations to provide an ideal nutrient supply to the cell culture. In contrast to the shake flask experiments, in the bioreactor systems pH and $pO_2$ is monitored online. The offline process parameters and set-points were fully controlled by a control software (Siemens, Munich Germany) using an automatic closed-loop system for monitoring, e.g., the pH control, nutrient feed addition, temperature control, stirring and gassing.

Example 1

CHO2 (CHO-DG44) Rituximab cells were cultured in a RPMI based basal medium with RPMI amino acid (AA) ratios versus optimized amino acid (AA) ratios with different total cumulative amounts of amino acids. The medium composition for medium 4 (medium 4.0, 4.1, 4.2 and 4.3) having RPMI AA ratios and medium (medium 5.0, 5.1 and 5.2) having optimized AA ratios with total cumulative amounts of amino acids ranging from 22 mM-66 mM (37 mM only in medium 4) are shown in Table 1 and the corresponding amino acid ratios in Table 2.

Minor variations in total AA concentrations are due to variations in molecular weight and minimal variation of used amino acid powders. The aim of this experiment was to demonstrate the impact of optimized amino acid ratios at different total cumulative amino acid levels. The experiment was performed in batch mode in duplicates (N=2).

TABLE 1

Compositions of Media 4.0, 4.1, 4.2 and 4.3 and Media 5.0, 5.1 and 5.2

|  | Basal medium 4 | Basal medium 5 | Unit |
|---|---|---|---|
| WFI | 0.800 | 0.800 | l/l |
| AA premixed powder (RPMI AA ratios)* | 3.08 (37 mM; medium 4.0) <br> 3.73 (45 mM; medium 4.1) <br> 5.58 (67 mM; medium 4.2) <br> 1.86 (23 mM; medium 4.3) |  | g/l |
| AA premix powder (optimized AA ratios)** |  | 4.23 (44 mM; medium 5.0) <br> 6.34 (66 mM; medium 5.1) <br> 2.11 (22 mM; medium 5.2) | g/l |

TABLE 1-continued

Compositions of Media 4.0, 4.1, 4.2 and 4.3 and Media 5.0, 5.1 and 5.2

| | Basal medium 4 | Basal medium 5 | Unit |
|---|---|---|---|
| Powder GM RPMI 86638 (table 1b) | 4.37 | 4.37 | g/l |
| NaHCO$_3$ | 3.0 | 3.0 | g/l |
| Monoethanolamin stock sol. (12.22 g/l stock solution) Sigma Aldrich Chemie | 800 | 800 | μl/l |
| Iron choline citrate (991.5 g/mol); Dr. Paul Lohmann GmbH KG | 0.2 | 0.2 | g/l |
| Selenic acid (25.79 mg/l stock sol.) | 100.0 | 100.0 | μl/l |
| Putrescine × 2HCl [mg/l] | 4.8 | 4.8 | mg/l |
| Insulin (5 g/l stock sol.) | 2 | 2 | ml/l |
| Chemical defined lipids (Gibco Life Technol. 92_0239DK) | 5.0 | 5.0 | ml/l |
| Hepes | 3.57 | 3.57 | g/l |
| NaCl | 6.00 | 6.00 | g/l |
| MgSO$_4$ | 0.049 | 0.049 | g/l |
| KCl | 0.40 | 0.40 | g/l |
| Ca(NO$_3$)$_2$*4H$_2$O | 0.10 | 0.10 | g/l |
| Glucose | 1.50 | 1.50 | g/l |
| Pluronic | 1.00 | 1.00 | g/l |
| 40% NaOH | adjust pH to 7.1 | adjust pH to 7.1 | ml/l |
| Water for injection (WFI) | add 1.0 | add 1.0 | l/l |
| Total glucose | 5.00 | 5.00 | g/l |

*Gln, Ile and Cys were added separately using a stock solution
**Gln and Ile were added separately using a stock solution TABLE 1a Amino Acid Ratios for Medium 4 (non-optimized) and Medium 5 (optimized)

| Amino Acid | Medium 4 (RPMI AA molar ratios) | Medium 5 (optimized AA molar ratios) |
|---|---|---|
| L-Alanine | — | — |
| L-Arginine | 2.5 | 2.1 |
| L-Asparagine | 0.9 | 1.8 |
| L-Aspartic Acid | 0.4 | 1.3 |
| L-Cysteine | 1.9 | 1.6 |
| L-Glutamic Acid | 0.4 | 0.9 |
| L-Glutamine | — | 46.4 |
| L-Glycine | 0.8 | 24.7 |
| L-Histidine | 0.3 | 0.9 |
| L-Isoleucine | 1.0 | 1.0 |
| L-Leucine | 1.0 | 1.7 |
| L-Lysine | 0.6 | 2.2 |
| L-Methionine | 0.3 | 0.5 |
| L-Phenylalanine | 0.2 | 0.7 |
| L-Proline | 0.5 | 2.3 |
| L-Serine | 0.8 | 2.1 |
| L-Threonine | 0.4 | 1.5 |
| L-Tryptophan | 0.1 | 0.4 |
| L-Tyrosine | 0.4 | 2.1 |
| L-Valine | 0.5 | 1.5 |

TABLE 1b

Composition Powder GM RPMI 86638

| COMPONENT | [g/L] |
|---|---|
| Sodium phosphate dibasic (anhyd.) | 0.8 |
| Choline chloride | 0.003 |
| i-Inositol | 0.035 |
| L-Glutathione reduced | 0.001 |
| Biotin | 0.0002 |
| Cyanocobalamin (Vitamin B12) | 0.000005 |
| D-Calcium pantothenate | 0.00025 |
| Folic Acid | 0.001 |
| Niacinamide | 0.001 |
| Para-aminobenzoic acid | 0.001 |
| Pyridoxine × HCl | 0.001 |
| Riboflavin | 0.0002 |
| Thiamine × HCl | 0.001 |
| D-Glucose | 3.5 |
| Ethanolamine × HCl | 0.01563 |
| Putrescine × 2HCl | 0.0048 |
| Sodium selenite | 0.000003458 |
| Sum g/L | 4.37 |

Materials and Methods:

The RPMI basal medium used in this experiment is based on the commercially available RPMI medium R8755 (Mediatech catalog no. 90022PB or Sigma Aldrich catalog no. R8755) that was originally developed at Roswell Park Memorial Institute in 1966 by Moore and his co-workers (SAFC, Biosciences product information). For serum-free use it has been supplemented as shown in table 1 containing sodium chloride (NaCl 6.0 g/L), potassium chloride (KCl 0.4 g/L), magnesium sulfate (MgSO$_4$ 0.0488 g/L) at a cumulative sum of bulk salts of 108.4 mmol/L.

The batch experiment was performed in 500 ml shake flasks with a starting volume of 125 ml. CHO2 (CHO-DG44) Rituximab cells were seeded at 0.3×10$^6$ cells/ml in medium 4, 4.1, 4.2 or 4.3 (RPMI AA ratios) and medium 5, 5.1 or 5.2 (optimized AA ratios). The shake flasks cultures were incubated at 36.5° C. in an incubator with 5% CO$_2$ at day 0-3 and 3% CO$_2$ from day 4 until the end of the cultivation.

The amino acid cysteine was provided in the powder formulation of medium 5, but was added separately from a stock solution in medium 4. For monitoring and control of the cultures, total cells, viable cells, viability, product concentration, glucose concentration, lactic acid concentration, ammonium concentration and osmolarity were measured up to day 7.

Results:

FIG. 1 (A-D) shows the results for cells cultured in RPMI medium with RPMI ratios (filled square) and optimized AA ratios (filled circles) i.e. viable cells concentration, viability, product concentration and lactate concentration at a total AA concentration of 44 mM. Highest viable growth and product concentration was achieved in cultures with optimized AA ratios at different cumulative AA concentrations of 44 mM (FIGS. 1A and C) and 66 mM (FIGS. 1E and G). For example, the product concentration was about 2.3-fold higher in cell cultures with optimized AA ratios (FIG. 10) at days 5 and 7, with a maximal product concentration of 166 mg/L compared to a maximal product concentration of 72 mg/L for cells grown in medium containing RPMI ratios. This was accompanied by a higher number of viable cells (FIG. 1A, up to $2.82 \times 10^6$ c/ml in medium 5 and $1.13 \times 10^6$ c/ml in medium 4.1). Viability profile for both cultures was in good agreement to each other and showed a clear decrease from day 3 onwards from 98% down to 25% viability on day 7 (FIG. 1 B). The glucose concentration, ammonium concentration and osmolarity showed a similar tendency in both cultures. For example, glucose concentration was maintained greater than 1.0 g/L over the cultivation period for all cultures to avoid any limitation, and pH was maintained in typical ranges for cell culture process. This demonstrates that all cultures were provided in sufficient amounts with major carbon sources such as glucose for cell growth, metabolism and product formation. As expected, the profile of the metabolic waste product lactate showed a growth dependent pattern, i.e. increased cell concentrations contribute to higher amounts of the metabolic waste product lactate (FIG. 1 D). It should be noted that the lactic acid production is not always growth-associated and can be further understood as an indicator for efficient glucose utilization (e.g. FIG. 4J).

Similar results were obtained at a total amino acid concentration of 66 mM (FIG. 1 E-H) for cells cultured in medium containing RPMI ratios (filled square) and optimized AA ratios (filled circles). The product concentration was about 3-fold higher in cell cultures with optimized AA ratios (Figure G) at days 5 and 7, with a maximal product concentration of 311 mg/L compared to a maximal product concentration of 96 mg/L for cells grown in medium containing RPMI AA ratios. This was accompanied by an increased number of viable cells (Figure E, up to $3.44 \times 10^6$ c/ml in medium 5.1 and $1.32 \times 10^6$ c/ml in medium 4.2). Viability profile for both cultures show a similar pattern, but cultures in medium 5.1 show a prolonged viability by approximately 1 day on day 5 (94% vs. 70% medium 4.2). Viability of both cultures show a clear decrease from day 3 onwards from 98% down to 55% and 25% viability on day 7 (FIG. 1 F). For lactate concentration, glucose concentration, ammonium concentration and osmolarity as well as for the pH progress a similar trend was observed as described above for cultures with a total amino acid concentration of 44 mM. Overall viable cell concentration and product concentration was higher at a higher total amino acid concentration (compare 66 mM (FIGS. 1 E and G) versus 44 mM (FIGS. 1A and C)), particularly for cells cultured with optimized AA ratios (product concentration for medium containing RPMI ratios: medium 4.2 (66 mM) vs. medium 4.1 (44 mM), day 5: 96-72 mg/l=+24 mg/l; product concentration for medium containing optimized AA ratios: medium 5.1 (66 mM) vs. medium 5.0 (44 mM) vs., day 5: 290-166 mg/l=+123 mg/l).

A similar trend could also be observed for 22 and 36 mM total amino acid concentration (FIG. 11). The maximal product concentration of approximately 45 mg/l (22 mM, medium 4.3, RPMI AA ratios; filled triangle right) increased to a maximal product concentration of 65 mg/l (36 mM, medium 4.0, RPMI AA ratios; filled cross) with increasing total amino acid concentration. However, this effect is smaller than the effect associated with the optimized amino acid ratio if one compares a maximal product concentration of 117 mg/l (22 mM, medium 5.2, and optimized AA ratios; filled square) vs. 45 mg/l (22 mM, medium 4.3, RPMI ratios) as shown in FIG. 11.

As can be taken from FIG. 1J, optimized AA ratios at the lowest tested total amino acid concentration of 22 mM (filled square) resulted in higher productivity (maximal product concentration 117 mg/l, optimized AA ratios, 22 mM) than RPMI AA ratios at the highest tested total amino acid concentration of 66 mM (filled circles, maximal product conc. 96 mg/ml, RPMI AA ratios). Thus, the highest productivity was achieved using media with optimized AA ratios, with a maximal product concentration of 117 mg/L (22 mM, optimized AA ratios; FIGS. 1I, J), 166 mg/l (44 mM, optimized AA ratios, FIG. 10) and 290 mg/l (66 mM, optimized AA ratios, FIG. 1 E). This shows that optimizing the AA ratios strongly increases productivity and that this can only be compensated to a very small extend by simply increasing the total AA concentration.

Example 2

Based on the optimized amino acid ratios in the basal medium 5 (RPMI based), several amino acids were varied as a single component-approach in their molar concentration by +/−20% and +/−40% (calculation is based on molar percentage for optimized AA ratios). Then, the performance was compared to the control cultures grown in medium 5.3 (identical to medium 5.0, but all amino acids were added individually as stock solutions). All required amino acids were provided by concentrated stock solutions to design a different medium composition. Thus, the media had a comparable total cumulative amino acid amount of approximately 43-44 mM, but different amino acid ratios. In one experiment the variation of single amino acid concentrations (single component-approach for L-arginine, L-asparagine, L-aspartate, L-histidine, L-leucine, L-lysine, L-methionine, L-phenylalanine, L-proline, L-serine, L-threonine, L-tryptophan, L-tyrosine, L-valine) by +20% and −20% vs. control medium 5.3 was tested. A similar approach was performed for variations of single amino acid concentrations (L-arginine, L-asparagine, L-aspartate, L-histidine, L-isoleucine, L-leucine, L-lysine, L-methionine, L-phenylalanine, L-proline, L-serine, L-threonine, L-tryptophan, L-tyrosine, L-valine) by +40% and −40% compared to control. The experiment was performed in batch mode with a RPMI based medium. Variation of AA by +/−20% or +/−40% is indicated as (20) or (40) for the specific medium used.

Materials and Methods:

This experiment was performed in 250 ml shake flasks with a starting volume of 75 ml and 100 ml. In all cultures CHO2 (CHO-DG44) Rituximab cells were seeded at $0.3 \times 10^6$ cells/ml in the control medium 5.3 (N=3) and the modified medium 5.3.1(20) (N=2) (single amino acid concentration varied by +/−20%), and medium 5.3.1(40) (single amino acid concentration varied by +/−40%). The shake flasks were incubated at 36.5° C. in an incubator (5% $CO_2$ atmosphere was provided from day 0 to 3 followed by 3% $CO_2$ until the end of the cultivation). Glucose was fed on day 2 and on day 4 and also on demand to keep the final glucose concentration between 2.5 g/l and 4.5 g/l. L-glutamine was also added on demand.

The medium 5.3 (identical to medium 5.0, but all amino acids were added individually as stock solutions) served as the basis for this experiment. In total, 14 amino acids were tested for the +/−20% single component-approach: L-arginine, L-asparagine, L-aspartate, L-histidine, L-leucine, L-lysine, L-methionine, L-phenylalanine, L-proline, L-serine, L-threonine, L-tryptophan, L-tyrosine and L-valine. In total 7 amino acids were not tested: L-alanine, L-cysteine/L-cystine, L-glutamine, L-glutamate, L-glutamine, L-isoleucine and L-glycine. In total 15 amino acids were tested for the +/−40% single component-approach: L-arginine, L-asparagine, L-aspartate, L-histidine, L-leucine, L-lysine, L-methionine, L-phenylalanine, L-proline, L-serine, L-threonine, L-tryptophan, L-tyrosine, L-valine and L-isoleucine. In total 6 amino acids were not tested: L-alanine, L-cysteine/L-cystine, L-glutamine, L-glutamate, L-glutamine and L-glycine.

The amino acids not tested were qualified as metabolic waste that are produced in excess in a cell culture (L-alanine, L-glycine, L-glutamate); are considered to be chemically instable due to oxidation of the compound or were not considered as being an essential compound for enhanced growth, especially after a cell peak e.g. L-glutamine.

Medium 5.3 was dissolved in water to form a 1.2-fold concentrate without amino acids to prepare Medium 5.3.1 (20) for which all amino acids were added separately from stock solutions and adjusted with water. Medium 5.3.1(40) was prepared as a 1.25-fold concentrate from Medium 5.3 for which all amino acids were added separately from stock solutions and adjusted with water.

Results:

The variation of single amino acid ratios showed that a reduction of L-leucine, L-phenylalanine, L-threonine, L-valine or L-isoleucine in the medium with optimized AA ratios by 40% resulted in reduced productivity (FIG. 2J and N). A small reduction in productivity was also observed when L-phenylalanine, L-valine or L-leucine was reduced by 20% (FIG. 2C and E-G).

For example, as shown in FIG. 2J, the average product concentration ranges from 129-184 mg/L on day 5 for the control medium 5.3 (optimized AA ratios) and the modified medium 5.3.1(40) (single amino acid reduced by −40%) and from 127-186 mg/L on day 7. This wide range in final titer illustrates that the final product concentration is similar in most media, but reduced in 5 cultures compared to the maximal control titer of 180 mg/L on day 7 (FIG. 2J and 2N). The maximal product concentration of 180 mg/L in the control medium 5.3 (optimized AA ratios) is 180 mg/L, which is reduced in the modified media 5.3.1(40), with L-phenylalanine, L-valine, L-leucine, L-threonine or L-isoleucine reduced by −40%, to a maximal product concentration in the range of 129-149 mg/L on culture day 5. A similar trend can be seen on day 7 with a product concentration of 179 mg/L in the control medium 5.3 and of 127-143 mg/L in the five modified media.

Reducing L-leucine, L-phenylalanine, L-threonine, L-valine or L-isoleucine in the medium with optimized AA ratios by 40% further resulted in reduced viable cell concentrations, accompanied by a decrease in viability and an increase in waste metabolite (lactate) production following day 3 (FIGS. 2H, 2L, 2M, 2O). No difference in viable cell concentration, cell viability or lactate production was observed when these amino acids were reduced by only 20% (see FIGS. 2A, 2B, 2D). A decrease of the viable cell concentration and viability occurred almost in all cultures as expected due to the common nutrient depletion and lack of feed addition in batch mode (FIGS. 2A, 2B, 2H, 2I, 2L and 2M). Glucose was maintained above critical levels and lactate production followed a growth-associated kinetic as expected in all cultures (FIG. 2K and O). Further no effect was observed on any of the other parameters measured such as osmolartiy, $PCO_2$ and pH.

The results show that reducing some of the amino acids negatively influences the viable cell concentration and/or product formation.

No effect on productivity, viable cell concentration, cell viability or lactate concentration was observed in medium with amino acids increased by 20 or 40% (data not shown).

Example 3

Based on the optimized amino acid ratios and the amino acids identified in example 2 in basal medium 5 (RPMI based), additional amino acids were varied as a single component-approach in their molar concentration by −40% in a different medium background. This medium containing the optimized AA ratios is further optimized for serum-free recombinant protein production and is chemically defined and is superior to the modified RPMI medium used in the previous experiments. In this experiment, single amino acids were reduced in a batch mode to demonstrate the effect of optimized amino acid ratios in basal medium under controlled bioreactor conditions for pH, dissolved oxygen (DO) and temperature.

Based on the optimized amino acid ratios in the basal medium 6.2, single amino acids L-lysine, L-methionine, L-proline, L-tryptophan or L-tyrosine were reduced in their molar concentration by 40%, or L-tyrosine and L-lysine were both reduced by 20% or 40%. The resulting performance was compared against the control culture medium containing the optimized AA ratios. Compared were cells cultivated in control medium 6.2 (optimized AA ratios, AA added as premixed powder) and control medium 6.4.1 (optimized AA ratios, AA added individually from stock solutions) with cells cultivated in medium 6.4.9-35 medium 6.4.15 (modified AA ratio, AA added individually from stock solutions). All tested medium compositions had a comparable total cumulative amino acid concentration of approximately 44 mM.

Materials and Methods:

Compared were cells cultured in control medium 6.2 (optimized AA ratios, AA added as premixed powder) and control medium 6.4.1 (optimized AA ratios, AA added individually from stock solutions) with cells cultured in medium 6.4.9 (L-lysine and L-tyrosine −20%), medium 6.4.10 (L-lysine and L-tyrosine −40%), medium 6.4.11 (L-tyrosine −40%), medium 6.4.12 (L-lysine −40%), medium 6.4.13 (L-methionine −40%), medium 6.4.14 (L-tryptophan −40%), medium 6.4.15 (L-proline −40%). All tested medium compositions had a comparable total cumulative amino acid concentration of 44-45 mM. All required amino acids were provided by concentrated stock solutions and added to medium 6.4.0 (identical to medium 6.2 and 6.4.1, but without amino acids) to prepare the different medium compositions 6.4.1 and The experiment was performed in a 48-miniaturized bioreactor system with a starting volume of 14 ml. In all cell cultures CHO2 (CHO-DG44) Rituximab cells were seeded in the respective medium at $0.3 \times 10^6$ cells/ml. The bioreactors were incubated at 36.5° C. for the entire cultivation period and dissolved $CO_2$ was controlled between 2-15% to prevent toxic concentrations based on the pH set-point of $(7.20-6.80)+/-0.2$. Control cultures and experimental runs were performed in duplicates (N=2).

gistic effect (FIG. 3C, filled cross). Reducing L-methionine, L-proline or L-tryptophan in the medium likewise resulted in a reduced product concentration on day 8 (265 mg/L, 274 mg/L, 277 mg/L, respectively). In summary, the results show that the medium with the optimized amino acid ratios resulted in the best productivity out of the tested media.

TABLE 2

Composition of Basal Medium (6.2, 6.3 and 6.4.0 without AA)

| Components | Medium 6.2 | Medium 6.3 | Medium 6.4.0 | Unit |
| --- | --- | --- | --- | --- |
| Total AA | 44 mM | 45 mM | 0 mM | |
| WFI | 0.8 | 0.8 | 0.6 | l/l |
| AA premixed powder (optimized AA ratios)* | 5.74 | — | — | g/l |
| AA premixed powder (RPMI ratios)* | | 4.83 | — | g/l |
| Medium 6 powder without AA | 10.10 | 10.10 | 10.10 | g/l |
| NaHCO3 | 4.5 | 4.5 | 4.5 | g/l |
| Iron choline citrate (ICC; MW = 991.5 g/mol) Dr. Paul Lohmann GmbH KG | 0.2 | 0.2 | 0.2 | g/l |
| L-Ornithine × HCL | 7.653 | 7.653 | 7.653 | mg/l |
| Putrescine × 2HCl [mg/l] | 5.237 | 5.237 | 5.237 | mg/l |
| Insulin (5 g/L stock sol.) (pharma Biocon)** | 2 | 2 | 2 | ml/l |
| Glucose | 5.00 | 5.00 | 5.00 | g/l |
| Succinic acid | 1.50 | 1.50 | 1.50 | g/l |
| Taurine | | | 0.0011495 | g/l |
| L-Hydroxy-proline | | | 0.0011248 | g/l |
| 40% NaOH | on demand | on demand | on demand | ml/l |
| WFI | add 1.0 | add 1.0 | add 0.8 | l/l |

*includes taurine and L-hydroxy-proline
**insulin may be substituted with insulin-like growth factor (IGF) at a final concentration of 50 µl/l TABLE 2a Amino Acid Ratios for Basal Medium 6.2 (optimized AA, AA premixed powder), 6.3 (non-optimized AA), 6.4.0.1 (optimized AA, control, AAs added separately)

| Amino Acids (AA) | Medium 6.2 | Medium 6.3 | Medium 6.4.0.1 |
| --- | --- | --- | --- |
| Total AA | 44 mM | 45 mM | 44 mM |
| L-Alanine | — | — | — |
| L-Arginine | 2.13 | 2.5 | 2.1 |
| L-Asparagine | 1.82 | 0.9 | 1.8 |
| L-Aspartic acid | 1.31 | 0.4 | 1.3 |
| L-Cysteine | 1.57 | 1.9 | 1.6 |
| L-Glutamic acid | 0.89 | 0.4 | 0.9 |
| L-Glutamine | 46.40 | 46.4 | 46.40 |
| L-Glycine | 24.70 | 24.7 | 24.7 |
| L-Histidine | 0.91 | 0.3 | 0.9 |
| L-Isoleucine | 1.00 | 1.0 | 1.0 |
| L-Leucine | 1.66 | 1.0 | 1.7 |
| L-Lysine | 2.24 | 0.6 | 2.2 |
| L-Methionine | 0.51 | 0.3 | 0.5 |
| L-Phenylalanine | 0.72 | 0.3 | 0.7 |
| L-Proline | 2.27 | 0.5 | 2.3 |
| L-Serine | 2.08 | 0.8 | 2.1 |
| L-Threonine | 1.46 | 0.4 | 1.5 |
| L-Tryptophan | 0.37 | 0.1 | 0.4 |
| L-Tyrosine | 2.09 | 0.3 | 2.1 |
| L-Valine | 1.49 | 0.5 | 1.5 |

Results:

In the control culture (optimized AA ratios, medium 6.4.0.1) a maximal product concentration of 317 mg/L was measured on day 8. In all test cultures the maximal product concentration was reduced compared to the control culture, ranging from 249 to 279 mg/L on day 8. Specifically, reducing L-lysine or L-tyrosine in the medium resulted in a product concentration of 268 mg/L and 279 mg/L on day 8, respectively. Interestingly, reducing both L-lysine and L-tyrosine by 40% resulted in an even lower product concentration of 249 mg/L, indicating an additive or even syner- The growth profiles showed comparable results for the test media and for the control media (FIG. 3A and 3B). The maximal viable cell concentration was a few days earlier in some of the cultures compared to the control culture (filled squares) and even slightly higher. For example, the viable cell concentration for all cultures ranged from a peak cell density of $3.7 \cdot 10^6$ cells/ml on day 4 to a lower cell density of $2.8 \cdot 10^6$ cells/ml on day 6 (control). Viability profiles for all cultures show a similar tendency with a sharp decrease on culture day 6. However, viability was even slightly higher in some of the test cultures towards the end of the culture period. Overall, the higher productivity in the control culture could be explained by a higher cell specific productivity. Metabolites and pH profiles were routinely monitored on a daily basis, but did not show any differences between the cultures.

Example 4

It was further found that the combination of the novel amino acid ratios in both basal medium and feed medium showed the best performance. Optimizing the amino acid ratios had not only an effect in basal medium (in batch mode), but also in the feed medium (fed-batch mode). Cells were incubated in basal medium with optimized AA ratios or RPMI AA ratios and fed with either feed medium with optimized AA ratios or RPMI AA ratios.

Example 4A

The impact of basal medium and feed medium was analyzed by culturing CHO2 (CHO-DG44) Rituximab cells in media with optimized amino acid ratios (optimized AA ratios, medium 6.2 and feed 6.2) or non-optimized amino acid ratios (RPMI AA ratios, medium 6.3 and feed 6.3) in a fed-batch mode in all four combinations at a standard feed rate of 30 ml/L/d based on the culture starting volume for all cultures. Basal and feed medium 6.2 containing optimized AA ratios are further optimized for serum-free recombinant protein production and are chemically defined and are superior to the modified RPMI media used. In another experiment (in 2-L bioreactor system, Example 4C), the final glucose concentration in the feed solution (feed medium 6.2.1 and feed medium 6.3.1) was increased to minimize the number of glucose additions and operator work by adding stock solutions (Table 3).

Materials and Methods:

Basal medium 6.2 and medium 6.3 were identically designed comprising about 44 mM total amino acids, but different amino acid ratios (Tables 2 and 2a). Likewise feed medium 6.2 and feed medium 6.3 were identically designed comprising about 508-511 mM total amino acids, but different amino acid ratios (Tables 3 and 6). In order to avoid an increased osmotic pressure, the glucose concentration in the feed medium 6.2 and 6.3 was reduced to a final concentration of 42 g/l. Glucose was further added on demand to maintain glucose >1 g/L during the experimental course.

The experiment was performed in a 48-miniaturized bioreactor system with a starting volume of 14 ml. In all cultures CHO2 (CHO-DG44) Rituximab cells were seeded at $0.3 \times 10^6$ cells/ml in test medium or in control medium as follows: basal medium 6.2 and feed medium 6.2 (optimized AA ratios, AA added as premixed powder), basal medium 6.3 and feed medium 6.3 (RPMI AA ratios, AA added as premixed powder). The bioreactors were incubated at 36.5° C. for the entire cultivation period and dissolved $CO_2$ was controlled between 2-15% to prevent toxic concentrations based on the pH set-point of (7.20-6.80)+/−0.2.

TABLE 3

Composition of Feed Media 6.2 and 6.2.1 (with optimized AA) and Media 6.3 and 6.3.1 (without optimized AA)

| Component (total AA) | Feed 6.2/6.2.1* | Feed 6.3/6.3.1 | Unit |
|---|---|---|---|
| Total AA conc. | 508 | 511 | mM |
| WFI | 0.7 | 0.7 | l/l |
| NaHCO3 | 1.5 | 1.5 | g/l |
| AA premixed powder (optimized AA ratios) | 71.38 | | g/l |
| AA premixed powder (RPMI AA ratios) | | 77.63 | g/l |
| Feed medium 6 powder without AA** | 12.57 | 12.57 | g/l |
| Insulin (5 g/L stock sol.) (pharma Biocon)*** | 10 | 10 | ml/l |
| Iron choline citrate (ICC; MW = 991.5 g/mol) Dr. Paul Lohmann GmbH KG | 0.56 | 0.56 | g/l |
| L-Ornithine × HCL | 7.65 | 7.65 | mg/l |
| Putrescine × 2HCl [mg/l] | 185.022 | 185.022 | mg/l |
| Glucose | 35.4/58.4 | 35.4/58.4 | g/l |
| L-Glutamine | 0 | 0 | g/l |
| Succinic acid | 5.26 | 5.26 | g/l |
| 40% NaOH | on demand | on demand | ml/l |
| WFI | add 1.0 | add 1.0 | l/l |
| Total glucose | 42/65 | 42/65 | g/l |

*Difference between feed medium 6.2 and 6.2.1 and feed medium 6.3 and 6.3.1 is the total glucose content.
**Feed medium 6 powder without AA contains 6.6 g glucose.
***Insulin may be substituted with IGF at a final concentration of 250 µg/l Results:

The effect of optimized amino acid ratios in basal medium and feed medium for IgG1 antibody (Rituximab) production in a controlled mini-bioreactor system in fed-batch (n=2) are shown in FIG. 4C. The maximal product concentration of 2786 mg/L on day 10 (2677 mg/L on day 12) was achieved with optimized amino acid ratios in both, basal and feed medium. Using a basal medium with RPMI AA ratios, but a feed medium with optimized AA ratios led to a considerably lower maximal product concentration of 2126 mg/L on day 12. Productivity was even further decreased in cultures using a basal medium with optimized AA ratios and a feed medium with RPMI AA ratios, resulting in a final titer of 1662 mg/L on day 12. Lowest product concentration was achieved with non-optimized amino acid ratios in both, basal and feed medium with a product concentration of 1577 mg/L on day 12.

Use of basal medium with non-optimized AA ratios followed by feed medium with optimized AA ratios slightly delayed viable cell concentrations, but reached almost comparable maximum viable cell concentrations. Compared to the respective cell culture using basal medium with optimized AA ratios the cell specific productivity was also slightly reduced (132.91 mg/$10^6$ cells vs. 161.3 mg/$10^6$ cells). Likewise the productivity was slightly delayed, particularly in earlier days (days 4-8) and remained lower over time. This shows that optimized AA ratios are beneficial for cell productivity in both, the basal medium and the feed medium.

This is accompanied with an increase in viable cell concentrations and viability for cultures in medium using optimized AA ratios, preferably in both the basal and the feed medium. Maximal viable cell concentrations for cell cultured in medium having optimized amino acid ratios in basal medium and in feed medium were found to be $16.6 \times 10^6$ cells/ml on day 8. Culturing cells in a basal medium with RPMI AA ratios and a feed medium with optimized AA ratios resulted in almost the same maximal viable cell concentration of $16.0 \times 10^6$ cells/ml (day 10), however, about two days later. Thus, non-optimized AA ratios in the basal medium seem to delay viable cell proliferation. Culturing cells in a feed medium with RPMI AA ratios severely reduced the maximum viable cell concentration to $13.3 \times 10^6$ cells/ml (basal medium with optimized AA ratios) or $11.5 \times 10^6$ cells/ml (basal medium with RPMI AA ratios) on day 8. Thus, optimized AA ratios in the feed medium seem to support higher viable cell concentrations.

A similar trend was also observed for viability (FIG. 4B), with an earlier and more severe decrease in viability in cultures without optimized AA ratios in the feed medium. No significant impact was observed for any of the other measured parameters.

In summary, the effect of a basal medium without optimized AA ratios seems to result in a reduced cell specific productivity, which cannot be totally compensated by using an optimized feed medium. Use of feed medium without optimized AA ratios on the other hand resulted in a reduced number of viable cells (FIG. 4A) and viability (FIG. 4B). Thus, feed medium with optimized AA ratios improved viability and viable cell concentration and thereby increased productivity, but also showed an effect on cell specific productivity (161.2 mg/$10^6$ cells vs. 124.9 mg/$10^6$ cells). In contrast to that, results for growth, viability and final titer also revealed that the maximal growth and maximal product concentration were clearly impacted by optimized AA ratios in basal medium and feed medium.

Example 4B

The impact of basal medium and feed medium was also analyzed using optimized amino acid ratios (optimized AA ratios, basal medium 6.2 and feed 6.2) or non-optimized amino acid ratios (RPMI AA ratios, medium 6.3 and feed 6.3) in a fed-batch mode in all four combinations at reduced feed rates in an uncontrolled shake flask system (pH and dissolved oxygen not controlled). The standard fed-batch feeding rate was adjusted from 30 ml/L/d (control) to 20 ml/L/d and 8 ml/L/d to avoid overfeeding and hence masking an effect.

Materials and Methods:

CHO2 (CHO-DG44) Rituximab cells were seeded at $0.3 \times 10^6$ cells/ml in basal and feed medium 6.2 (optimized AA ratios) or in basal and feed medium 6.3 (RPMI AA ratios). Feed medium 6.2 and feed medium 6.3 contained a metabolically adjusted glucose concentration of 42 g/l to ensure comparable metabolic profiles (e.g. glucose) of shake flask experiments and 2 L bioreactors. Viable cells, viability, product concentration, glucose concentration, lactic acid concentration, ammonium concentration and osmolarity were measured as described above according to the sample intervals. Experiments and controls were performed in duplicates (N=2).

In this experiment 500 ml shake flasks with a starting volume of 60 ml were used to culture cells in basal and feed medium with or without optimized AA ratios. The shake flasks cultures were incubated at 36.5° C. in an incubator (8% $CO_2$ from day 0 to 2 and 5% $CO_2$ from day 2, and 3% $CO_2$ from day 3 until the end of the cultivation). Feed rate was set to 20 ml/L/d for days 1 to 5 and 8 ml/L/d for days 5 to 11. Feed solution was added every 2 days to the culture with the aim to prevent glucose overfeeding and minimize osmotic pressure caused by an increased glucose level. The feed rate was calculated as follows e.g. 30 ml/L/d *0.06 L=1.8 ml feed/day=3.6 ml feed/2 days, metabolically adjusted feed rate 20 ml/L/d=1.2 ml/d=2.4 ml feed/2 days. Glutamine was maintained >0.1 g/L over the cultivation, mainly replenished from an increased L-glutamine concentration in the basal medium at start, but not from feed medium.

Results:

Effect of optimized amino acid ratios in medium and feed for IgG1 antibody (Rituximab) production in uncontrolled shake flask system in fed-batch mode at reduced feed rate (N=2).

The effect of basal medium can be seen if one compares the maximal product concentration of 897 mg/L (filled diamond) in cultures with non-optimized amino acid ratios in basal medium 6.3 and optimized amino acid ratios in feed medium 6.2 with 1049 mg/L (filled square) in cultures with optimized amino acid ratios in basal medium 6.2 and optimized amino acid ratios in feed medium 6.2, both at reduced feed rates (FIG. 4F). Having non-optimized amino acid ratios in the basal medium therefore resulted in delayed and reduced product formation. The maximal product concentration of 641 mg/L (filled circle) in cultures with optimized amino acid ratios in basal medium 6.2 and with non-optimized amino acid ratios in feed medium 6.3 was higher than the maximal product concentration of 468 mg/L (filled triangle) in cultures with non-optimized amino acid ratios in basal medium and in feed medium (FIG. 4F). This result clearly demonstrates the positive impact of optimized amino acids in basal medium on maximal product titer.

Furthermore, the maximal product concentration of 1049 mg/L was achieved in cultures with optimized amino acid ratios in basal medium and feed medium, which was reduced to 641 mg/L when using a feed medium with non-optimized AA ratios at reduced feed rates (FIG. 4F). A similar tendency for product production was found for cells cultured in basal medium without optimized AA ratios and a feed medium with optimized AA ratios (897 mg/L) or a feed medium without optimized AA ratios (468 mg/L). This means that there is a strong positive impact of optimized amino acids in feed medium on maximal product performance, however, best results were achieved when using optimized AA ratios in both the basal and the feed medium.

The viability profile followed a similar trend with a sharp decrease from 96% on day 5 for all cultures (FIG. 4E). The maximal viable cell concentration ranged from 3.8-9.6 $10^6$ cells/ml on day 5-6 (FIG. 4D). In general, a feed medium with optimized AA ratios increased viable cell concentration (FIG. 4D). This result was in line with the improved viability (FIG. 4E).

Furthermore, optimized amino acid ratios in the basal medium had a positive effect on cell proliferation. This may be taken from a comparison of the viable cell concentration for cells cultured in basal medium with ($7.27 \times 10^6$ cells/ml, filled circle) or without ($3.8 \times 10^6$ cells/ml, filled triangle) optimized amino acid ratios and feed medium without optimized amino acid ratios on day 5. This result illustrates the positive effect of an optimized basal medium on maximal growth performance.

When feed medium with optimal AA ratios was used, the maximal viable cell concentration was comparable for a basal medium without optimized AA ratios ($9.6 \times 10^6$ cells/m, filled diamond) and with optimized AA ratios ($7.9 \times 10^6$ cells/ml, filled square). The feed effect can be described if one compares the maximal growth of cells cultured with optimized amino acid ratios in basal medium and with optimized amino acid ratios in feed medium ($7.9 \times 10^6$ cells/ml, filled square) or without optimized AA ratios in the feed medium ($7.2 \times 10^6$ cells/ml, filled circle). Likewise, when using a basal medium without optimized AA ratios, the maximal viable cell concentration was $9.6 \times 10^6$ cells/ml for cells cultured in feed medium with optimized AA ratios and this was reduced to $3.9 \times 10^6$ cells/ml for cells cultured in feed medium without optimized AA ratios (FIG. 4D).

Generally, there are two major aspects that are in good agreement to the viable cell growth. First, the highest remaining viability of 37-40% was achieved on day 9 for cultures with optimized amino acid ratios in feed (with or without optimized amino acid ratios in basal medium). Secondly, the viability drop down from day 5 onwards was shifted by approximately one day for the cultures with optimized amino acids in the feed medium. These results clearly show that a higher viability and a prolongation of the viability profile can be obtained with optimized basal medium and feed medium.

Example 4C

The impact of basal medium and feed medium with and without optimized amino acid ratios was further tested in a standard fed-batch format in an up-scaled fully controlled 2-L bioreactor system.

The 2 L bioreactor system is a representative model for large scale bioreactors for commercial manufacturing (up to 12,000 L scale and beyond). The standard fed-batch feeding rate of 30 ml/L/d was applied and feed solution was fed in a continuous mode starting from day 2 to day 14. Other process parameters were set to our platform conditions for successful scale-up based on our experience, i.e. oxygen transfer, shear force, $CO_2$ removal, pH range, agitation and power input per volume. The medium combinations were tested in duplicates (N=2).

Materials and Methods:

The experiment was performed in a fully controlled 2 L bioreactor system with a starting volume of 1.8 L. CHO2 (CHO-DG44) Rituximab cells were seeded at $0.3 \times 10^6$ cells/ ml in all cultures using basal medium 6.2 (optimized AA ratios) or basal medium 6.3 (RPMI AA ratios) and feed medium 6.2.1 (optimized AA ratios and adapted glucose concentration of 65 g/l) or feed medium 6.3.1 (RPMI AA ratios and adapted glucose concentration of 65 g/l). The bioreactors were incubated at 36.5° C. for the entire cultivation and dissolved $CO_2$ was controlled between 2-15% to prevent toxic concentrations based on the pH set-point of (6.95 on days 0-3 and 6.80 on days 3-day 14)+/−0.20.

Glucose concentration in the feed solution was optimized to a final concentration of 65 g/l in order to minimize osmotic pressure caused by glucose over feeding, but also to reduce the number of glucose additions from stock solutions if necessary. The design of feed medium 6.2 and feed medium 6.2.1 was identical except for the final glucose concentration. Likewise feed medium 6.3 and feed medium 6.3.1 were identical except for the final glucose concentration.

Viable cells, viability, product concentration, glucose concentration, lactic acid concentration, ammonium concentration and osmolarity were measured as described above according to the sample intervals. The feed media contained glucose, but no L-glutamine, thus glutamine was added from a stock solution on demand to keep the glutamine concentration in the range of 0.1-0.4 g/l. Glucose level was to be maintained at >2 g/L for the entire cultivation. Experiments were performed in duplicates (N=2).

Results:

In general, results of the 2 L system were in good agreement to the findings from the previous shake flasks experiments with respect to maximal titer and viable growth. For example, the maximal product concentration of 2213 mg/L (filled squares) was achieved with optimized amino acid ratios in basal medium and feed medium (FIG. 4I). Culturing cells without optimized amino acid ratios in the feed medium reduced the maximal product concentration to 1654 mg/L (filled circles) as shown in FIG. 4I. Culturing cells in basal medium without optimized amino acid ratios strongly delayed product formation. A similar maximal product concentration of 2213 mg/L (optimized amino acid ratios in basal and feed medium) vs. 2144 mg/L (optimized amino acid ratios only in the feed medium) was obtained due to the positive effect of optimized feed medium. However, the product formation kinetics were clearly different due to the impact of non-optimized basal medium. Thus, for optimal product concentrations optimized amino acid ratios are required to be present in both, the basal and the feed medium.

These observations were in good agreement with the viable cell concentrations. The maximal viable cell peak of $12.7 \times 10^6$ cells/ml was achieved with optimized amino acid ratios in basal medium and feed medium compared to the maximal cell peak of $8.7 \times 10^6$ cells/ml with either non-optimized amino acid ratios in basal medium or feed medium (FIG. 4G). The maximal viable growth peak of $12.7 \times 10^6$ cells/ml was due to a combined effect on viable cell concentration of optimized amino acid ratios in basal medium and feed medium for fed-batch cultures. Further, the effect of basal medium and the effect of feed can be seen if one compares the exponential growth phase from day 4-9 for the cultures without optimized AA in basal medium and with optimized AA in feed medium vs. a culture with optimized AA in basal medium and without optimized AA in feed medium. FIG. 4G shows that the growth kinetic for optimized basal medium was steeper compared to non-optimized basal medium although both cultures achieved a similar maximal cell peak of approximately $8.6 \times 10^6$ cells/ml. In contrast, the slower growth kinetic with non-optimized basal medium, but optimized feed medium led to a prolongation of viable cells from day 10 to 14.

The viability profile followed a similar trend as discussed above. A maximal viability over a prolonged run time could be attributed to the feed effect (compare the viability of 79% vs. 49-54% on day 14) (FIG. 4H). Viability profiles for cells with optimized AA ratios in basal medium and in feed medium or with optimized AA ratios in basal medium and without optimized AA ratios in feed medium followed a similar trend. Other measured parameters such as metabolites and pH did not show any significant differences.

Example 4D

The impact of optimized AA ratios in basal medium and feed medium was further investigated (optimized AA ratios in RPMI basal medium 3.9 and RPMI feed medium 3 or non-optimized amino acid ratios RPMI AA ratios in RPMI basal medium 3.1 and RPMI feed medium 2) in a RPMI environment in fed-batch mode for all four combinations using CHO2 (CHO-DG44) Rituximab cells. RPMI is a commercial medium with a known composition.

The total amino acid concentration in RPMI basal cell culture medium and RPMI feed medium increased with adjusting the amino acid ratio to the optimized amino acid ratio of the invention. To rule out that the observed effects were simply due to an increased overall amino acid concentration, in a separate experiment RPMI basal cell culture medium and RPMI feed medium was adjusted with different amino acid ratios (spent media optimized amino acid ratio).

Material and Methods:

The RPMI basal medium used in this experiment is based on the commercially available RPMI medium R8755 (Mediatech catalog no. 90022PB or Sigma Aldrich catalog no. R8755) that was originally developed at Roswell Park Memorial Institute in 1966 by Moore and his co-workers (SAFC, Biosciences product information). For serum-free use it has been supplemented as shown in table 4.

This experiment was performed in 250 ml shake flasks with a starting volume of 100 ml. All cultures were seeded in shake flasks at $0.3 \times 10^6$ cells/ml in the specific media compositions: control RPMI medium 3.1 (without optimized AA ratios, total AA 10.0 mM), RPMI medium 3.9 (with optimized amino acid ratios, total AA −15.2 mM), RPMI feed medium −2 (without optimized amino acid ratios, total AA 124 mM), RPMI feed medium-3 (with optimized amino acid ratios, total AA 548 mM), RPMI medium 3.5 (RPMI medium 3.1+AA, spent media optimization, total AA 12 mM), RPMI feed medium 3.5 (RPMI feed-2+AA, spent media optimization, total AA 140 mM). The 7 amino acids added for spent media optimization of the basal medium were L-methionine, L-phenylalanine, L-proline, L-threonine, L-tryptophan, and L-tyrosine×2Na×2H$_2$O and L-valine each added at 30 mg/l and the amino acids added for spent media optimization of the feed medium were L-cysteine, L-methionine, L-proline, L-threonine, L-tyrosine×2Na×2H$_2$O and L-valine each added at 360 mg/l. Basal medium 3.1, 3.5 and 3.9 was fortified with plant hydrolysate to support initial growth at the beginning of the cultivation. For this reason the hydrolysate was not provided in the feeding solutions. As may be taken from the experiments above (see medium 4 and medium 5) basal RPMI based medium may also be used without Hypep.

Shake flasks were incubated at 36.5° C. in an incubator (5% $CO_2$ atmosphere was provided from day 0 to 3 followed by 3% $CO_2$ until the end of the cultivation). Feeding solution was added every second day at a feed rate of 30 ml/L/d from day 2-4 and at a reduced feed rate of 3 ml/L/d from day 5-8. Glucose was fed on demand to maintain the actual glucose concentration between 2-4 g/l over the cultivation period. Total cells, viable cells, viability, product concentration, glucose concentration, lactic acid concentration, ammonium concentration and osmolarity were measured every second day until the end of cultivation to monitor and control the experimental progress. Experiments were performed in duplicates (N=2).

TABLE 4

Composition of RPMI Basal Medium 3.1 (non-optimized AA), 3.9 (optimized AA), 3.5 (spent media analysis)

| Components | Medium 3.1 | Medium 3.9 | Medium 3.5 | Unit |
|---|---|---|---|---|
| WFI | 0.800 | 0.800 | 0.800 | l/l |
| RPMI 1640 (Product No. Sigma-Aldrich R8755) | 10.40 | 10.40 | 10.40 | g/l |
| AA supplementation for spend media analysis (met, phe, pro, thr, trp, tyr, val) | — | — | 0.21 | g/l |
| AA supplementation - optimized ratios | | 0.8883 | | |
| NaHCO$_3$ | 3.0 | 3.0 | 3.0 | g/l |
| Monoethanolamine (12.216 g/l stock sol.) Sigma-Aldrich Chemie | 800 | 800 | 800 | μl/l |
| Iron choline citrate (ICC; 991.5 g/mol) Dr. Paul Lohmann GmbH KG | 0.2 | 0.2 | 0.2 | g/l |
| Fe-Citrate (10 g/l stock sol) | 0.0 | 0.0 | 0.0 | ml/l |
| Selenic acid (25.79 mg/l stock sol.) | 100.0 | 100.0 | 100.0 | μl/l |
| Putrescine × 2HCl | 4.8 | 4.8 | 4.8 | mg/l |
| Insulin (5 g/l stock sol.) | 2 | 2 | 2 | ml/l |
| chem. defined Lipids (Gibco Life Technol. 92_0239DK) | 5.0 | 5.0 | 5.0 | ml/l |
| Hepes | 3.57 | 3.57 | 3.57 | g/l |
| Glucose | 1.50 | 2.17 | 1.50 | g/l |
| L-Glutamine total | 0.85 | 0.70 | 0.85 | g/l |
| Pluronic | 1.00 | 1.00 | 1.00 | g/l |
| HyPep 1510 (Kerry Sheffield) | 4.0 | 4.0 | 4.0 | g/l |
| 40% NaOH | as needed (adjust to pH = 7.1 +/−0.1) | as needed (adjust to pH = 7.1 +/−0.1) | as needed (adjust to pH = 7.1 +/−0.1) | ml/l |
| WFI | add 1.0 L | add 1.0 L | add 1.0 L | l/l |

TABLE 4a

Amino Acid Ratios of Basal Medium RPMI 1640 (original), Basal Medium 3.1, 3.9, Medium 3.5 (spent media analysis), and Medium 6.2

| Amino Acid | RPMI 1640 | Medium 3.1 | Medium 3.9 | Medium 3.5 | Medium 6.2 |
|---|---|---|---|---|---|
| Total AA conc. | 6.3 mM | 10.0 mM | 15.2 mM | 12 mM | 44 mM |
| L-Alanine | — | — | — | — | — |
| L-Arginine | 2.5 | 2.5 | 2.5 | 2.5 | 2.1 |
| L-Asparagine | 1.0 | 1.0 | 1.8 | 1.0 | 1.8 |
| L-Aspartic acid | 0.4 | 0.4 | 1.3 | 0.4 | 1.3 |
| L-Cysteine | 1.0 | 1.0 | 2.2 | 1.0 | 1.6 |
| L-Glutamic acid | 0.4 | 0.4 | 0.9 | 0.4 | 0.9 |
| L-Glutamine | 5.4 | 15.3 | 12.6 | 15.3 | 46.4 |
| L-Glycine | 0.4 | 0.4 | 0.4 | 0.4 | 24.7 |
| L-Histidine | 0.2 | 0.2 | 0.9 | 0.2 | 0.9 |
| L-Isoleucine | 1.0 | 1.0 | 1.0 | 1.0 | 1.0 |
| L-Leucine | 1.0 | 1.0 | 1.7 | 1.0 | 1.7 |
| L-Lysine | 0.6 | 0.6 | 2.3 | 0.6 | 2.2 |
| L-Methionine | 0.3 | 0.3 | 0.5 | 0.8 | 0.5 |
| L-Phenylalanine | 0.2 | 0.2 | 0.7 | 0.7 | 0.7 |
| L-Proline | 0.5 | 0.5 | 2.3 | 1.1 | 2.3 |
| L-Serine | 0.8 | 0.8 | 2.1 | 0.8 | 2.1 |
| L-Threonine | 0.4 | 0.4 | 1.5 | 1.1 | 1.5 |
| L-Tryptophan | 0.1 | 0.1 | 0.4 | 0.5 | 0.4 |
| L-Tyrosine | 0.3 | 0.3 | 2.1 | 0.6 | 2.1 |
| L-Valine | 0.5 | 0.5 | 1.5 | 1.1 | 1.5 |

TABLE 5

Composition of RPMI Feed Medium-2 (non-optimized AA), -3 (optimized AA), -3.5 (spent media analysis)

| Component | Feed-2 | Feed-3 | Feed-3.5 | Unit |
|---|---|---|---|---|
| WFI | 0.700 | 0.700 | 0.700 | l/l |
| RPMI Feed premix 83480CP (w/o L-Gln, L-Cys and cystine, with RPMI AAs) 12x | 41.58 | 41.58 | 41.58 | g/l |
| L-Cysteine × HCl × H$_2$O | 3.12 | 2.60 | 3.12 | g/l |
| Cystine × 2 HCl | 390.90 | 390.90 | 750.90 | mg/l |
| AA supplement for feed medium-3 (optimized AA) | — | 61.75 | — | g/l |
| AA supplement for spend media analysis (met, pro, trp, tyr, val) | — | — | 1.80 | g/l |
| Insulin (5 g/l stock sol.) | 10 | 10 | 10 | ml/l |
| Fe-citrate (10 g/l stock sol) | 25.00 | 25.00 | 25.00 | ml/l |
| Selenic acid (25.79 mg/l stock sol.) | 100.00 | 100.00 | 100.00 | μl/l |
| L-Glucose | 26.00 | 26.00 | 26.00 | g/l |
| L-Glutamine | 8.00 | 8.00 | 8.00 | g/l |
| 40% NaOH | on demand | on demand | on demand | ml/l |

TABLE 5-continued

Composition of RPMI Feed Medium-2 (non-optimized AA), -3 (optimized AA), -3.5 (spent media analysis)

| Component | Feed-2 | Feed-3 | Feed-3.5 | Unit |
|---|---|---|---|---|
| WFI | add 1.0 | add 1.0 | add 1.0 | l/l |
| Total Glucose | 50.00 | 50.00 | 50.00 | g/l |
| Total Glutamine | 8.00 | 8.00 | 8.00 | g/l |

TABLE 5a

RPMI Feed premix (1x) 83480CP, without bulk salts*:

| COMPONENT | [mg/L] | COMPONENT | [mg/L] |
|---|---|---|---|
| L-Arginine | 200 | L-Lysine × HCl | 40 |
| L-Asparagine × H2O | 56.8 | L-Methionine | 15 |
| L-Aspartic Acid | 20 | Niacinamide | 1 |
| D-Biotin | 0.2 | L-Phenylalanine | 15 |
| D-calcium pantothenate | 0.25 | L-Proline | 20 |
| Choline Chloride | 3 | PABA (Para-aminobenzoic acid) | 1 |
| Cyanocobalamin | 0.005 | Pyridoxine × HCl | 1 |
| D-Glucose (dextrose anhyd.)** | 2000 | Riboflavin | 0.2 |
| Folic acid | 1 | L-Serine | 30 |
| L-Glutamic acid | 20 | Sodium phosphate (dibasic) | 800 |
| L-Glutathione, reduced | 1 | Thiamine × HCl | 1 |
| L-Glycine | 10 | L-Threonine | 20 |
| L-Histidine | 15 | L-Tryptophan | 5 |
| Hydroxy L-proline | 20 | L-Tyrosine 2Na × 2H$_2$0** | 14.4 |
| myo-inositol | 35 | L-Valine | 20 |
| L-Isoleucine | 50 | | |
| L-Leucine | 50 | Sum mg/L | 3464.4 |

*Omitted bulk salts: Calcium dinitrate × 4H$_2$O, magnesium sulfate, potassium chloride, sodium chloride and sodium hydrogen carbonate
**Added separately

TABLE 6

Amino Acid Ratios of RPMI Feed-2 (non-optimized) and RPMI Feed-3 (optimized AA), RPMI Feed Medium 3.5 (spent media analysis), Feed Medium 6.2 and 6.2.1 (optimized AA) and Feed Medium 6.3 and 6.3.1 (non-optimized AA)

| Amino Acid | Feed 2 | Feed 3 | Feed 3.5 | Feed 6.2/ 6.2.1 | Feed 6.3/ 6.3.1 |
|---|---|---|---|---|---|
| Total AA conc. | 124 mM | 548 mM | 140 mM | 508 mM | 511 mM |
| L-Alanine | — | — | — | — | — |
| L-Arginine | 3.01 | 0.97 | 3.01 | 0.97 | 2.49 |
| L-Asparagine | 0.99 | 3.22 | 0.99 | 3.22 | 0.87 |
| L-Aspartic Acid | 0.39 | 0.23 | 0.39 | 0.23 | 0.39 |
| L-Cysteine | 4.44 | 0.80 | 4.94 | 0.68 | 0.34 |
| L-Glutamic Acid | 0.36 | 0.26 | 0.36 | 0.26 | 0.36 |
| L-Glutamine | 11.97 | 2.55 | 11.97 | — | — |
| L-Glycine | 0.35 | 0.29 | 0.35 | 1.12 | 0.76 |
| L-Histidine | 0.25 | 1.73 | 0.25 | 0.57 | 0.25 |
| L-Isoleucine | 1.00 | 1.00 | 1.00 | 1.00 | 1.00 |
| L-Leucine | 1.00 | 3.22 | 1.00 | 3.22 | 1.00 |
| L-Lysine | 0.57 | 1.70 | 0.57 | 1.60 | 0.57 |
| L-Methionine | 0.26 | 0.58 | 0.79 | 0.58 | 0.26 |
| L-Phenylalanine | 0.24 | 0.86 | 0.24 | 0.86 | 0.24 |
| L-Proline | 0.46 | 1.35 | 1.14 | 1.35 | 0.46 |
| L-Serine | 0.75 | 3.23 | 0.75 | 3.23 | 0.75 |
| L-Threonine | 0.44 | 1.84 | 1.10 | 1.84 | 0.44 |
| L-Tryptophan | 0.06 | 0.45 | 0.06 | 0.45 | 0.06 |
| L-Tyrosine | 0.14 | 0.03 | 0.45 | 0.83 | 0.41 |
| L-Valine | 0.45 | 1.57 | 1.12 | 1.57 | 0.45 |

In the spent medium analysis commercial available RPMI medium was modified and fortified with various nutrient supplementations to avoid nutrient limitations and to ensure improved growth and product formation in the fed-batch experiment. For this purpose AA supplements were added to the medium according to the medium recipe for medium 3.1. An amino acid analysis was performed for samples taken from the cell culture supernatant on days 4 and 7, except for L-arginine. As a result it was found that the concentration of the following seven amino acids was below 15 mg/L: L-valine, L-threonine, L-proline, L-methionine, L-phenylalanine, L-tyrosine and L-tryptophan. Based on this prior art spent media analysis, these amino acids were additionally supplemented in a basal medium (RPMI medium 3.5). Specifically, the amino acids L-methionine, L-phenylalanine, L-proline, L-threonine, L-tryptophan, L-tyrosine, and L-valine were additionally provided each at 30 mg/L in the basal medium (Tables 4 and 4a). In the feed medium, the amino acids L-methionine, L-threonine, L-proline, L-cystine, L-tyrosine and L-valine were additionally provided each at 360 mg/L (Tables 5 and 6).The experiment was basically performed as described above using RPMI basal cell culture medium with or without optimized amino acid ratios and a RPMI feed medium with and without optimized amino acid ratios. Additionally cells were incubated with RPMI basal medium and feed medium comprising spent media amino acid ratios in either the RPMI basal cell culture medium or in the RPMI feed medium or in both.

Results:

In summary, the effect of the optimized AA ratios in RPMI basal cell culture medium and/or in RPMI feed medium on cell culture performance in fed-batch mode was investigated using CHO2 (CHO-DG44) cells producing the antibody Rituximab. Specifically, cell viability (FIG. 4L, O), viable cells (FIG. 4K, N), product titer (FIG. 4M, P) and lactate concentration (data not shown) were monitored.

The major effect of optimized feed medium or basal medium could be seen in the final product concentration and also in the product kinetics (slope of curve) as indicated in FIG. 4M.

For example, the product titer of cells cultured in RPMI basal cell culture medium and RPMI feed medium both comprising the optimized amino acid ratios were higher (259 mg/L) compared to control cells cultured in RPMI basal cell culture medium and RPMI feed medium without optimized amino acid ratios (162 mg/L), as shown in FIG. 4M. In a culture with optimized AA ratios in the basal medium, but non-optimized AA ratios in the feed medium, the maximal product titer was reduced to 171 mg/ml. Interestingly, the effect of optimized amino acid ratios in the feed medium was similar up to day 4 (167 mg/L vs. 161 mg/L) and only differed at later culture days. Furthermore, in the case of non-optimized basal medium, the product formation and curve kinetic (slope of the curve) was delayed and resulted in a maximal product concentration of approximately 152-162 mg/L on day 8 (without optimized AA ratios in basal medium and with or without optimized AA in feed medium).

A similarly positive effect could be observed for the viable cell concentration and viability using the RPMI media system (RPMI basal cell culture medium and RPMI feed medium). Highest viable cell concentrations with a maximal viable cell concentration of approximately 3.5×10$^6$ cells/ml (FIG. 4K) and highest cell viabilities (FIG. 4L) were achieved when the optimized amino acid ratios were used in both, RPMI basal cell culture medium and RPMI feed medium. If the optimized amino acid ratios were only applied in the basal cell culture medium a sharp decrease in viable cell concentration (FIG. 4K) and viability (FIG. 4L) was observed from day 6 onwards. The maximal viable cell concentration was lower (FIG. 4K and N) for cells cultured in basal cell culture medium without optimized AA ratios and feed medium with optimized AA ratios ($2.2 \times 10^6$ cells/ml) and even lower for cells cultured in basal cell culture medium and feed medium, both without the optimized amino acid ratios (maximal viable growth up to $1.70 \ 10^6$ cells/ml, day 4). In summary, this example demonstrates the superiority of the optimized amino acid ratio on cell culture performance in a RPMI based medium, namely product titer, viable cell concentrations and cell viability.

Similar results were obtained in the other experiment including the same media and a medium supplemented with AAs according to the spent media analysis.

As mentioned above, adjusting the optimized amino acid ratios in RPMI basal cell culture medium significantly improved product titers compared to the unmodified RPMI media system. Product titer in cell culture comprising the optimized amino acid ratios in both, basal and feed medium was higher compared to control without any implementation of optimized amino acid ratios in RPMI (titer of 0.406 g/L vs. 0.173 g/L). Hence by adjusting amino acid ratios according to the optimized amino acid ratios in both basal medium and feed medium, the product titer was increased by a factor of about 2.3 in a commercial media system such as RPMI. Product titer in RPMI basal cell culture medium comprising optimized amino acid ratios and RPMI feed medium without amino acid adjustment was higher compared to the controls without implementation of optimized amino acid ratios in basal and feed medium (titer of 0.267 g/L vs. 0.173 g/L). Product titer in a culture with optimized amino acid ratios only in the RPMI feed medium was almost comparable to the control without any novel amino acid ratios implemented in either basal medium or feed medium (titer of 0.159 g/L vs. 0.173 g/L). Again, this result demonstrates that the optimized amino acid ratios should be applied from the beginning of a cultivation experiment, i.e. in both basal and feed medium. In this setting, application of optimized amino acid ratios only in feed medium was not sufficient to achieve maximal product titers.

The product titer in RPMI with spent media amino acid ratios in both basal medium and feed medium was higher (0.302 g/L, open square) compared to the control without any amino acid ratio adjustment (0.173 g/L, filled diamond), but lower compared to the optimized amino acid ratios in RPMI medium and in RPMI feed medium (0.406 g/L, filled square). Furthermore, product titer with spent media amino acid adjustment in RPMI basal medium, but not in RPMI feed medium (0.193 g/L, open circle) was higher compared to the control without optimized amino acid ratios in basal or feed medium (0.173 g/L, filled diamond), but clearly lower compared to the optimized amino acid ratios in RPMI basal culture medium only (titer 0.267 g/L, filled circle) (FIG. 4 P).

Thus the effect of spent media amino acid ratio adjustment in basal cell culture medium and in feed medium (maximal titer 302 mg/L) was reduced compared to the impact on overall cell culture performance of the optimized amino acid ratios in basal cell culture medium and in feed medium (maximal titer of 406 mg/L). For spent media amino acid ratio adjustment only in the basal medium, but not in the feed medium a maximal titer of only 193 mg/L was obtained.

According to the titer, the viable cell concentration that is achieved for all cultures follows a similar trend with a maximal cell peak on day 4. Most cultures have a maximal viable cell concentration of approximately $3.5 \times 10^6$ cells/ml, except for cultures without any supplementation in the basal medium ($1.7$-$2 \times 10^6$ cells/ml). The viable growth with highest viable cell numbers over time was achieved with cells in optimized amino acid ratios in both basal medium and feed medium. This result demonstrates a combined effect of optimized basal medium and optimized feed as shown in FIG. 4N and P.

The viability profile (FIG. 4O) follows a similar trend with a breakdown on day 4 for most of the cultures except for the culture with optimized AA ratios in basal medium and feed medium. This finding is in good agreement to the viable growth pattern as shown in FIG. 4N. No significant impact of the media on other parameters such as metabolites and pH was observed.

Example 5

It was found that certain amino acids have an impact on cell metabolism with respect to the maximal product concentration, viable cell concentration and viability. The impact of varying these amino acids was further analyzed in combination in fed-batch mode with a serum-free, chemically defined medium. The variation of the amino acids was investigated within two AA groups that are a) L-phenylalanine, L-valine, L-leucine, L-threonine, L-isoleucine (5 AAs) and b) L-phenylalanine, L-valine, L-leucine, L-threonine, L-isoleucine, L-tyrosine, L-lysine (7 AAs). The amino acids were then varied in basal medium and feed medium by +/−20% and +/−40% in a positive or negative alternating mode based on the optimized amino acid ratios from the control (basal medium 6.4.0.1 and feed medium 6.4). Alternating mode means that the first AA is increased, the second AA is decreased, the third AA is increased etc. in the same direction in basal medium and in feed medium by 20% or 40% (calculated on a molar basis). The alternating mode is described by the usage of small letters (reduction by −20% or −40%, e.g. his, tyr) and capital letters (increase by +20% or +40%, e.g. HIS, TYR). In order to provoke a strong cellular response with respect to maximal growth and product formation, the nutrient feeding rates was reduced in some experiments.

Materials and Methods:

CHO2 (CHO-DG44) Rituximab cells were cultured in fed-batch in medium 6.4.0.1 and feed medium 6.4 (with optimized amino acid ratios) at a standard feed rate and a reduced feed rate. The experiment was separated into 3 approaches testing AA variations in combination that are a) variation of 5 AAs in basal medium and feed medium by +/−40%, b) variation of 7 AAs in basal medium and feed medium by +/−40%, and c) variation of 7 AAs in basal medium and feed medium by +/−20% or +/−40% at a reduced feed rate.

For the 5 AA set-up the amino acids L-phenylalanine, L-valine, L-leucine, L-threonine, L-isoleucine were varied by +/−40% in a positive or negative alternating mode (capital or non-capital AA letters) compared to control with optimized amino acid ratios in both basal and feed medium. Media used were: Basal medium 6.4.3 (5 amino acids PHE, val, LEU, thr, ILE varied by +/−40%, positive), basal medium 6.4.4 (5 amino acids phe, VAL, leu, THR, ile varied by +/−40%, negative), feed medium 6.4.3 (5 amino acids PHE, val, LEU, thr, ILE varied by +/−40%, positive), feed medium 6.4.4 (5 amino acids phe, VAL, leu, THR, ile varied by +/−40%, negative).

For the 7 AAs set-up the following media were used: Basal medium 6.4.5 (7 amino acids PHE, val, LEU, thr, ILE, tyr, LYS varied by +/−20%, positive), basal medium 6.4.7 (7 amino acids PHE, val, LEU, thr, ILE, tyr, LYS varied by +/−40%, positive), basal medium 6.4.8 (7 amino acids phe, VAL, leu, THR, ile, TYR, lys varied by +/−40%, negative), feed medium 6.4.5 (7 amino acids PHE, val, LEU, thr, ILE, tyr, LYS varied by +/−20%, positive), feed medium 6.4.7 (7 amino acids PHE, val, LEU, thr, ILE, tyr, LYS varied by +/−40%, positive), feed medium 6.4.8 (7 amino acids phe, VAL, leu, THR, ile, tyr, lys varied by +/−40%, negative). It should be added that due to solubility reasons L-tyrosine was not increased in the alternated mode of feed medium 6.4.8, which was only relevant for a 7 AA variation by +40% not for a 20% AA variation. Except for feed medium 6.4.8, lacking the increased tyr concentration, the variations of the amino acids used in the feed medium were the same as in the basal medium in all cultures.

The experiment was performed in a miniaturized bioreactor system with a starting volume of 14 ml. In all cell cultures CHO2 (CHO-DG44) Rituximab cells were seeded at $0.3 \times 10^6$ cells/ml in basal medium for fed-batch cultivation. The bioreactors were incubated at 36.5° C. for the entire cultivation and dissolved pCO2 was controlled between 2-15% to prevent toxic concentrations based on the pH set-point of (7.20-6.80)+/−0.2. The standard feed rate of 30 ml/L/d was applied to cultures with a 5 AA variation by +/−40% (FIG. 5A-C) and 7 AA variation by +/−40% (FIG. 5D-F). A reduced feed rate of 20 ml/L/d on days 1-5 and 8 ml/L/d on days 6-11 was applied to cultures with 7 AA variation by +/−20% and +/−40% (Figure G-I). Feed solution was added continuously to the culture and attention was paid to prevent glucose overfeeding and minimize osmotic pressure caused by an increased glucose addition. For example, feed medium 6.4.3, feed medium 6.4.4, feed medium 6.4.7 or feed medium 6.4.8 contained a reduced glucose concentration of 42 g/l. All feed media contained glucose, but no L-glutamine, thus glutamine was added from a stock solution on demand to keep the glutamine concentration in the range of 0.1-0.4 g/l. Glucose was also added on demand to keep the glucose level >2 g/L for the entire cultivation. Viable cells, viability, product concentration, glucose concentration, lactic acid concentration, ammonium concentration and osmolarity were measured as described above according to the sample intervals. Experiments and controls were performed in duplicates (N=2).

Results:

The combined variation of 5 AAs or 7 AAs (+/−40% at a standard feed rate) and especially the combined variation of 7 AAs at a reduced feed rate (7 AAs+/−20% and +/−40% at a reduced feed rate) in a medium with otherwise optimal AA ratios reduced the productivity and viable growth in cell cultures.

Variation of 5 AAs: The highest maximal product concentration of 1909 mg/L was achieved on day 10 in control cultures (optimized AA ratios in basal and feed medium) (FIG. 5C). For variations of 5 AAs, the maximal product concentration was reduced by alternately varying 5 AAs in both directions to 1523 mg/L (phe, VAL, leu, THR, ile+/−40%, alternating mode) and 1799 mg/L (PHE, val, LEU, thr, ILE+/−40%, alternating mode), respectively. Interestingly, the product formation showed a different kinetic (slope of curve), as may be seen from the product titer on day 10 with 1909 mg/L (control) vs. 1523 mg/L vs. 1498 mg/L (PHE, val, LEU, thr, ILE and phe, VAL, leu, THR, ile, respectively, +/−40%, alternating mode). A combined variation of 5 AAs by +/−20% showed a maximal product concentration that was only slightly reduced to (phe, VAL, leu, THR, Ile varied by +/−20%, 1806 mg/l on day 10) or comparable to (PHE, val, LEU, thr, ILE varied by +/−20%, 2058 mg/L on day 12) control cultures (data not shown). The results indicate that the variation of five amino acids in combination by only +/−20% had no significant impact on product formation or on the maximal product titer.

The viable cell concentration profile followed a similar trend for all cultures (control versus test cultured varied by +/−40%) with a maximal viable peak density in the range of $13.8-19.4 \times 10^6$ cells/ml on day 8 (FIG. 5A). A maximal viable cell density of $19.4 \times 10^6$ cells/ml was observed in control cultures with optimized AA ratios in basal medium (basal medium 6.4.0.1) and feed medium (feed medium 6.4). The maximal viable cell concentration in cultures with varied amino acid ratios were considerably lower (PHE, val, LEU, thr, ILE by +/−40%, viable cell concentration of $13.8 \times 10^6$ cells/ml; phe, VAL, leu, THR, ile+/−40%, viable cell concentration of $15.3 \times 10^6$ cells/ml) (FIG. 5A). The viable growth of the test cultures with varied amino acids by +/−20% (5 AA) was comparable to the control cultures with optimized amino acid ratios (data not shown).

Furthermore, the viability profile of all cultures was fairly comparable showing a decline in viability for all cultures starting on day 8. Interestingly, in one of the cultures with the amino acid ratios of 5 AAs varied by +/−40% (PHE, val, LEU, thr, ILE), the viability remained rather high at 56% at the end of the cultivation period (days 11-14), compared to a viability of 13% for the control culture on day 14 (FIG. 5B). For test cultures with the amino acid ratios of 5 AAs varied by +/−20% all curves were comparable to control (data not shown).

Variation of 7 AAs: Similar results were obtained with the variation of 7 amino acids (L-phenylalanine, L-valine, L-leucine, L-threonine, L-isoleucine, L-tyrosine, L-lysine) by +/−40%. For example, the product concentration of 1618 mg/L (phe, VAL, leu, THR, ile, tyr, lys by +/−40%, alternating mode) or 1456 mg/L (PHE, val, LEU, thr, ILE, tyr, LYS by +/−40%, alternating mode) on day 10 was reduced compared to the maximal product concentration of 1909 mg/L measured in control cultures on day 10 (FIG. 5F). This result was in good agreement with the results obtained with the 5 AA variations. Altering 7 AAs by +/−20% resulted in a comparable maximal product concentration of 1861 mg/l (7 AA PHE, val, LEU, thr, ILE, tyr, LYS varied by +/−20%) or a slightly reduced maximal product concentration with 1622 mg/l (7 AA phe, VAL, leu, THR, ile, tyr, lys varied by +/−20%, negative alternating mode) compared to control cultures with a maximal product concentration of 1909 mg/l on day 10 (data not shown). This means that the variation of 7 amino acids by +/−20% only had a minor effect on product formation and maximal product concentration in a cell culture.

The maximal viable cell concentration ranged from $14.4-19.4 \times 10^6$ cells/ml on day 8 (FIG. 5D). The viable growth of the test cultures with 7 varied amino acids was comparable to the viable growth of the cultures with medium comprising 5 varied amino acids varied by +/−40% (compare FIGS. 5A and D). Likewise, the viability for 7 AA varied by +/−40% was comparable to the cultures with 5 AA varied by 40% (compare FIGS. 5B and 5E). Again one culture (7 amino acids PHE, val, LEU, thr, ILE, tyr, LYS, varied by +/−40%) showed a higher viability of 45% compared to control at the end of cultivation.

Altering 7 AAs by +/−20% resulted in a comparable growth profile for all cultures including control cultures with a similar maximal peak cell density on day 8 of 18.9-20.1× $10^6$ cells/ml (data not shown).

Also the viability profile was comparable for all cultures that remained rather high with 95% until culture day 8, but then dropped below 30% at the end of the culture period (data not shown).

Variation of 7 AA with reduced feed rate: To potentiate the effect cells were additionally cultured in a fed-batch mode using a reduced feed rate. Compared were control cultures with a standard feed rate (medium 6.4.0.1 and feed medium 6.4, standard feeding), control cultures with reduced feed rate (medium 6.4.0.1 and feed medium 6.4 with reduced feed rate) and test cultures with 7 amino acids varied by +/−20% or +/−40% at reduced feed rate. The maximal product concentration in control cultures at a standard feed rate was 1909 mg/l on day 10 (1782 mg/L day 12, filled square) and 1611 mg/l for the control culture with a reduced feed rate (day 12, filled circle) (FIG. 5I). Altering the concentration of 7 amino acids by 20% (PHE, val, LEU, thr, ILE, tyr, LYS; reduced feed rate) resulted in a maximal product concentration of 1448 mg/l (day 12, filled cross). This titer was further reduced in cultures with 7 AAs varied by +/−40% to a maximal product concentration of 1269 mg/L (phe, VAL, leu, THR, ile, Tyr, lys; reduced feed rate, filled triangle) or 999 mg/L (PHE, val, LEU, thr, ILE, tyr, LYS; feed rate reduced, filled X) on day 12. Thus, the variation of the AA ratio of 7 key amino acids reduced the productivity compared to control culture and this was more pronounced when the feed medium was added at a reduced feed rate.

The viable cell concentration showed a comparable trend irrespective of the feed rate (compare FIG. 5D and 5G). The viable cell concentration showed a maximal cell peak between days 6 and 8 (FIG. 5G). For example, control cultures showed a maximal viable cell concentration of 19.4×$10^6$ cells/ml at standard feed rate and this was slightly reduced at a reduced feed rate to 16.5×$10^6$ cells/ml. The maximal cell concentration for cultures with 7 AAs varied by +/−20% (PHE, val, LEU, thr, ILE, tyr, LYS) was approximately 13.5×$10^6$ cells/ml and even lower with about 11×$10^6$ cells/ml for cultures with 7 AAs varied by +/−40%.

The viability profile for all cultures followed a similar trend with a clear decrease starting between days 8 and 10 (FIG. 5H). Other parameters such as glucose, osmolarity or pH progress did not show any significant differences compared to the control cultures.

Example 6

In this fed-batch experiment, the impact of an optimized medium and feed medium on the cell culture performance was demonstrated for several CHO-DG44 cell lines that produce different monoclonal antibodies or a fusion protein as an example for pharmaceutically relevant proteins. The intention is to demonstrate that the optimized cell culture medium (with optimized amino acid ratios in basal medium and with optimized amino acid ratios in feed medium) clearly contributes to an improved productivity for a multipurpose manufacturing site.

Materials and Methods:

This experiment was performed in a miniaturized bioreactor system with a starting volume of 15 ml. All CHO-DG44 cell lines expressing a different therapeutic molecule were seeded at 0.3×$10^6$ cells/ml in basal medium 6.2 and feed medium 6.2, both with optimized AA ratios. The therapeutic molecules expressed in CHO-DG44 cells were Rituximab with a heavy chain having the amino acid sequence of SEQ ID NO: 1 and a light chain having the amino acid sequence of SEQ ID NO:2, mAb6 with a heavy chain having the amino acid sequence of SEQ ID NO: 3 and a light chain having the amino acid sequence of SEQ ID NO: 4, mAb5 and an Fc-fusion protein having the amino acid sequence of SEQ ID NO: 5. The bioreactors were incubated at 36.5° C. for the entire cultivation and dissolved $CO_2$ was controlled between 2-15% to prevent toxic concentrations based on the pH set-point of 6.95 (+/−0.15) and 6.80+/−0.15 from day 3 onwards. For this fed-batch application a platform process for successful scale-up was applied that included a standard feed rate of 30 ml/L/d. This means that the nutrient feed solution was added daily for the entire cultivation from day 1 until the end of cultivation. Glutamine was added from a stock solution on demand to keep the glutamine concentration in the range of 0.1-0.4 g/l. Glucose was also added on demand to keep the glucose level >0.6 g/L for the entire cultivation. Viable cells, viability, product concentration, glucose concentration, lactic acid concentration, ammonium concentration and osmolarity were measured as described above. Experiments and controls were performed in duplicates (N=2).

Results:

The product concentration of several CHO-DG44 cell lines expressing different therapeutic proteins was high for all proteins, but varied slightly. The maximal product concentration varied from 8213 mg/L on day 11 for mAb6 producing cells (FIG. 6C), 4655 mg/L on day 11 for mAb5 producing cells (FIG. 6C), 1778-2061 mg/L on day 11 for Fc-fusion protein and Rituximab producing cells (FIG. 6D). This variation in titer ranging from 1.7 g/l up to >8.2 g/l is accompanied by a variable viable cell concentration and viability. These results demonstrate that different CHO-DG44 cells expressing a variety of different recombinant proteins were able to grow and proliferate in the optimized culture medium in fed-batch mode (FIG. 6A-D).

Example 7

The effect of different concentrations of iron choline citrate on cell culture performance, specifically cell growth and product formation, was investigated in shake flask experiments using medium 6.2a. It was found that (i) iron choline citrate increased product titers and (ii) that the novel compound iron choline citrate is superior compared to commonly used iron carriers such as, for example, iron pyro phosphate, iron phosphate and iron citrate.

Materials and Methods:

The experiment was performed in 250 ml shake flasks with a starting volume of 100 ml. All cultures were seeded at 0.3×$10^6$ cells/ml (CHO2 (CHO-DG44) cells producing Rituximab) in basal medium 6.2a containing iron choline citrate at three different concentrations (0.2 g/1, 1 g/L or 2 g/l) or iron pyro phosphate (0.5 g/1, 0.8 g/1 or 1.3 g/l), or iron phosphate (0.3 g/1, 0.5 g/1, 0.7 g/l) at about equimolar amounts and feed medium 6.2a without iron choline citrate. The concentration ranges of iron pyro phosphate and iron phosphate were chosen to be in the same range (on a molar basis) as iron choline citrate. For example, iron choline citrate at 1.0 g/L (titer of 2.81 g/L) is about equimolar to iron phosphate at 0.3 g/L (titer of 2.29 g/L), and about equimolar to iron pyro phosphate at 1.3 g/L (titer of 2.26 g/L).

Basal medium 6.2a is a precursor medium that is almost identical to basal medium 6.2 except for additionally comprising some non-essential cofactors and nucleotides and containing no succinic acid, putrescine at only 4.8 mg/l and a total amino acid concentration of 40 mM instead of 44 mM. Further Glutamine was added at a lower amount resulting in a ratio relative to isoleucine of 37.42.

In a parallel experiment CHO2 (CHO-DG44) Rituximab cells were cultured in basal medium 6.2a with iron choline citrate at different concentrations (0 g/l, 0.2 g/l, 0.4 g/l or 2 g/l) and feed medium 6.2a containing iron choline citrate at 0.56 g/l or in basal medium 6.2a with iron citrate at 0.1 g/l and feed medium 6.2a containing iron citrate at 0.25 g/l. The concentration of iron citrate (0.1 g/l and 0.25 g/l) was chosen to be about equimolar to iron choline citrate at 0.2 g/l in the basal medium and 0.56 g/l in the feed medium.

Feed medium 6.2a is a precursor medium that is almost identical to feed medium 6.2 except for additionally comprising some non-essential cofactors and nucleotides and slightly higher sodium bicarbonate and containing putrescine at only 33.02 mg/l and a total amino acid concentration of 511 mM instead of 508 mM. Further alanine was additionally present in the medium with a ratio relative to isoleucine of 0.15.

Shake flasks with a starting volume of 60 ml in 250 ml flasks were incubated at 37° C. in an incubator (10% CO2 atmosphere was provided from day 0 to 3 followed by 3% CO2 for one day and 0% CO2 until the end of the cultivation). Feeding solution was added every day at a feed rate of 30 ml/L/d starting on day two. Glucose was fed on demand to maintain the actual glucose concentration between 2-4 g/l over the cultivation period. Total cells, viable cells, viability, product concentration, glucose concentration, lactic acid concentration, ammonium concentration and osmolarity were measured every second day until the end of cultivation to monitor and control the experimental progress. Experiments were performed in duplicates (N=2).

Results:

Product titers with iron choline citrate at 1.0 g/L were significantly higher than control at 0.2 g/L iron choline citrate (titer of 2.81 g/L vs. 2.07 g/L in control) and even slightly higher than product titers with iron choline citrate at 2.0 g/l (titer of 2.67 g/L) (FIG. 7B). Further, product titers were considerably higher with iron choline citrate at 2.0 g/L or 1.0 g/L (titer 2.67 g/L or 2.81 g/L) compared to iron pyro phosphate (titer of 2.24 g/L-2.37 g/L) or iron phosphate (titer of 2.29 g/L-2.38 g/L) at about equimolar amounts (FIG. 7B).

Maximal viable cell concentration was achieved with 2.0 g/L iron choline citrate in basal medium resulting in an improved cell culture performance compared to control (0.2 g/L iron choline citrate in basal medium) and to most commonly used iron carriers tested with different concentrations (FIG. 7A). The viable cell concentration of cells cultured in a basal medium comprising iron phosphate and iron pyrophosphate as iron carriers sharply declined from day 10 to 11 with negative impact on cell culture performance.

Similar results were found in a parallel experiment. Product titers with iron choline citrate at 2.0 g/L were higher than negative control cultures without iron choline citrate (titer of 3.06 g/L vs. 2.19 g/L in negative control) or in cultures with iron choline citrate in the basal medium at 0.4 g/L (titer of 2.87 g/L) or at 0.2 g/L (titer of 2.66 g/L) (FIG. 7C). At lower iron choline citrate concentrations (<1 g/l) the effect seemed to be concentration dependent and a considerable increase in product concentration was achieved when iron choline citrate was added at 0.2 g/L compared to the negative control without iron choline citrate.

Further, product titers with iron citrate at 0.1 g/L were lower than equimolar iron choline citrate at 0.2 g/L (titer of 2.38 g/L vs. 2.66 g/L) (FIG. 7D).

Example 8

The effect of different concentrations of iron choline citrate on cell culture performance, specifically cell growth and product formation, was investigated in shake flask experiments using an RPMI based medium. It was found that (i) iron choline citrate increased product titers and (ii) that the novel compound iron choline citrate is superior compared to commonly used iron carriers such as, iron citrate.

Material and Methods:

The experiment was performed in 250 ml shake flasks with a starting volume of 60 ml. All cultures were seeded at $0.3 \times 10^6$ cells/ml (CHO2 (CHO-DG44) cells producing Rituximab) in basal medium 3.1 containing iron choline citrate at different concentrations (0 g/l, 0.2 g/l, 0.4 g/l, or 2 g/l) or iron citrate (0.1 g/l, 0.2 g/l or 1 g/l) at about equimolar amounts and feed medium 2 containing iron citrate at 0.25 g/l. The concentration of iron citrate of 0.1 g/l, 0.2 g/l and 1 g/l was chosen to be about equimolar to iron choline citrate at 0.2 g/l, 0.4 g/l and 2 g/l in the basal medium, respectively.

Shake flasks were incubated at 37° C. in an incubator (10% CO2 atmosphere was provided from day 0 to 3 followed by 5% CO2 for one day and 0% CO2 until the end of the cultivation). Feeding solution was added every day at a feed rate of 30 ml/L/d starting on day two. Glucose was fed on demand to maintain the actual glucose concentration between 2-4 g/l over the cultivation period. Total cells, viable cells, viability, product concentration, glucose concentration, lactic acid concentration, ammonium concentration and osmolarity were measured every second day until the end of cultivation to monitor and control the experimental progress. Experiments were performed in duplicates (N=2).

Results:

Product titers with iron choline citrate at 2.0 g/L were higher than negative control without iron choline citrate (titer of 0.244 g/L vs. 0.156 g/L in negative control) or in cultures with iron choline citrate in the basal medium at 0.4 g/L (titer of 0.217 g/L) or 0.2 g/L (titer of 0.194 g/L) (see FIG. 8D and compare FIG. 8A, B and C). Thus, the effect of iron choline citrate seemed to be concentration dependent and a considerable increase in product concentration was achieved when iron choline citrate was added at 0.2 g/L compared to the negative control without iron choline citrate.

Further, product titers with iron citrate at 0.1 g/L were lower than equimolar iron choline citrate at 0.2 g/L (titer of 0.184 g/L vs. 0.194 g/L; FIG. 8A). Likewise product titers with iron citrate at 0.2 g/L were lower than equimolar iron choline citrate at 0.4 g/L (titer of 0.200 g/L vs. 0.217 g/L; FIG. 8B) and product titers with iron citrate at 1.0 g/L were significantly lower than equimolar iron choline citrate at 2.0 g/L (titer of 0.201 g/L vs. 0.244 g/L; FIG. 8C).

Overall viable cell concentrations showed similar profiles for iron choline citrate and iron citrate, but equimolar concentration of iron choline citrate vs. iron citrate resulted in higher viable cell concentrations (e.g., titers obtained by equimolar iron citrate with 1.0 g/L (titer 201 mg/L) were clearly lower than those obtained with 2.0 g/l iron choline citrate (titer 244 mg/L)). Further, compared to commercial iron carriers such as iron citrate, the (equimolar) application of iron choline citrate resulted in lower osmolarity values, which is considered to be beneficial for mammalian cell culture with respect to viable cell concentration and cell viability. Compared to negative control (no addition of iron choline citrate) iron choline citrate increased osmolarity only slightly (data not shown). Viable cell concentrations and cell viability were only slightly improved when iron choline citrate was added in increasing concentrations.

Example 9

The effect of iron choline citrate and equimolar iron citrate in media platform 6.2 or an RPMI based medium platform (basal medium 3.1 and feed medium 2) on cell culture performance in fed-batch mode in a 2 L bioreactor, specifically cell growth and product formation, was investigated (CHO2 (CHO-DG44) producing Rituximab). It was found that (i) iron choline citrate increased product titer, (ii) and was superior compared to commonly used iron carriers such as iron citrate. Hence, the positive effects of iron choline were independent of the applied cultivation system (e.g. shake flask experiments or controlled 2 L bioreactors or the medium used).

Material and Methods:

The experiment was performed in a fully controlled 2 L bioreactor system with a starting volume of 1.8 L. CHO2 (CHO-DG44) Rituximab cells were seeded at $0.3 \times 10^6$ cells/ml in all cultures using basal medium 6.2a containing iron choline citrate (0.2 g/l or 2.0 g/l) or iron citrate (1 g/l) and feed medium 6.2a containing iron choline citrate at 0.56 g/l (FIGS. 9A-C) or RPMI based basal medium 3.1 containing iron choline citrate (0.2 g/l or 2.0 g/l) or iron citrate (1 g/l) and RPMI based feed medium 2 containing iron citrate at 0.25 g/l. The concentration range of iron citrate was chosen to be in the same range (on a molar basis) as iron choline citrate. The bioreactors were incubated at 37° C. for the entire cultivation and dissolved $CO_2$ was controlled between 2-15% to prevent toxic concentrations based on the pH set-point of (7.07 on days 0-3 and 6.92 on days 3-day 14)+/−0.17. DO set-point was 60% and feed was added continuously at 30 ml/L/d. Viable cells, viability, product concentration, glucose concentration, lactic acid concentration, ammonium concentration and osmolarity were measured as described above according to the sample intervals. The feed media contained glucose and glucose level was maintained at >2 g/L for the entire cultivation. Glutamine was added from a stock solution on demand to keep the glutamine concentration in the range of 0.1-0.4 g/l. Experiments were performed in duplicates (N=2).

Results:

Product titers with iron choline citrate at 2.0 g/L in basal medium 6.2a were higher compared to control cultures with 0.2 g/L iron choline citrate (titer of 2.04 g/L vs. 1.62 g/L in control) or 1.0 g/L iron citrate (titer of 1.73 g/L) (FIG. 9C). This demonstrates that the effect of iron choline citrate on product titer was superior compared to iron citrate at equimolar concentrations. Whereas product concentrations were increased, viable cell concentrations and cell viability using different concentrations of iron choline citrate or equimolar concentrations of iron citrate were comparable. A slightly faster decrease in viable cell concentration and viability starting on day 8 for cultures treated with iron choline citrate was observed (FIG. 9A and B). The overall osmolarity in cultures using media platform 6.2a was within an acceptable range for all samples (280—approximately 400 mOsmo/kg, day 0-12, data not shown).

Likewise product titers with iron choline citrate at 2.0 g/L in an RPMI based medium were higher compared to control at 0.2 g/L iron choline citrate (titer of 0.257 g/L vs. 0.237 g/L in control) or 0.1 g/l iron citrate (titer of 0.200 g/L) (FIG. 9D). Whereas product concentrations were increased, viable cell concentrations and cell viability in the RPMI based media system at different concentrations of iron choline citrate or equimolar iron citrate were comparable. The overall osmolarity in cultures using the RPMI based media platform was slightly increased (350-440 mOsmo/kg, day 0-12, data not shown).

Example 10

A glutamine synthetase (GS) deficient cell line derived from CHO-K1 (CHO-K1 GS) was transfected in order to express and produce Rituximab as an example protein using a glutamine synthetase-based protein expression system. The growth of this CHO-K1 GS cell line producing Rituximab and the production of Rituximab as an example protein were analysed. It was found that the media with the improved amino acid ratios can also be used for a GS-deficient cell line and that the amount of the produced protein of interest is comparable high to that of other cell lines (see FIG. 6C).

Material and Methods:

This experiment was performed in a miniaturized bioreactor system with a starting volume of 15 ml. The CHO-K1 GS cell line expressing Rituximab was seeded at $0.7 \times 10^6$ cells/ml in basal medium 6.2GS and cultured using feed medium 6.2GS, both with optimized AA ratios. Compared to the basal medium 6.2 and feed medium 6.2 some minor changes were made:

Basal medium 6.2GS: Elimination of glutamine from AA premix powder (optimized AA ratios) due to GS system, change from succinic acid 1.5 g/L to disodium succinate $6H_2O$ 3.43 g/L formulation and increase of iron choline citrate from 0.2 g/L to 1.8 g/L.

Feed medium 6.2GS: Increase of glucose from 35.4 g/L to 83.4 g/L and change from Succinic acid 5.26 g/L to disodium succinate $6H_2O$ 12.0 g/l formulation The therapeutic molecule expressed in CHO-K1 GS cells was Rituximab with a heavy chain having the amino acid sequence of SEQ ID NO: 1 and a light chain having the amino acid sequence of SEQ ID NO:2. The bioreactors were incubated at 34.5° C. for the entire cultivation and dissolved $CO_2$ was controlled between 2-15% to prevent toxic concentrations based on the pH set-point of 6.95 (+/−0.25). For this fed-batch application a platform process for successful scale-up was applied that included a standard feed rate of 30 ml/L/d. This means that the nutrient feed solution was added daily for the entire cultivation from day 1 until the end of cultivation. Glucose was also added on demand to keep the glucose level >0.6 g/L for the entire cultivation. Viable cells, viability, product concentration, glucose concentration, lactic acid concentration, ammonium concentration and osmolarity were measured as described above. Experiments were performed in duplicates (N=2).

Results:

The parameters viable cell density, viability and product concentration of the duplicates from CHO-K1 GS cell line expressing Rituximab were comparable or even better compared to other cell lines. The two small scale bioreactors showed a high preharvest product concentration of 8665 mg/L and 8102 mg/L after the 14 days fed batch cultivation process. These results demonstrate that the glutamine synthetase (GS) deficient cell line derived from CHO-K1 was able to proliferate and to produce a protein of interest at very high titers using the culture medium with the optimized AA ratios (FIGS. 10A-C).

In view of the above, it will be appreciated that the present invention also relates to the following items:

Items

1. A basal cell culture medium for culturing mammalian cells comprising the following amino acids at a molar ratio relative to isoleucine (mM/mM) of:
   L-leucine/L-isoleucine of about 1.2-2.2,
   L-phenylalanine/L-isoleucine of about 0.5-0.9,
   L-tyrosine/L-isoleucine of about 1.5-2.7,
   L-threonine/I-isoleucine of about 1.0-1.9, and
   L-valine/L-isoleucine of about 1.0-1.9,
   wherein the basal cell culture medium has a total amino acid content of about 25 to 150 mM.
2. The basal cell culture medium of item 1, further comprising L-lysine at a molar ratio relative to isoleucine of about 1.6-2.9 (mM/mM).
3. The basal cell culture medium of items 1 or 2, further comprising at least one of the following amino acids at a molar ratio relative to isoleucine (mM/mM) of:
   L-tryptophan/L-isoleucine of about 0.3-0.5,
   L-proline/L-isoleucine of about 1.6-3.0; or
   L-methionine/L-isoleucine of about 0.4-0.7.
4. The basal cell culture medium of item 3, comprising L-tryptophan, L-proline and L-methionine each at the molar ratios according to item 3.
5. A basal cell culture medium for culturing mammalian cells comprising the following amino acids at a molar ratio relative to isoleucine (mM/mM) of:
   L-leucine/L-isoleucine of about 1.3-1.8,
   L-phenylalanine/L-isoleucine of about 0.6-0.9,
   L-tyrosine/L-isoleucine of about 1.7-2.5,
   L-threonine/I-isoleucine of about 1.2-1.8, and
   L-valine/L-isoleucine of about 1.3-1.6,
   wherein the basal cell culture medium has a total amino acid content of about 25 to 100 mM.
6. The basal cell culture medium of items 1 or 5, further comprising L-lysine at a molar ratio relative to isoleucine of about 1.8-2.7 (mM/mM).
7. The basal cell culture medium of items 1, 2, 5 or 6, further comprising at least one of the following amino acids at a molar ratio relative to isoleucine (mM/mM) of:
   L-tryptophan/L-isoleucine of about 0.3-0.5,
   L-proline/L-isoleucine of about 1.6-3.0; or
   L-methionine/L-isoleucine of about 0.4-0.7.
8. The basal cell culture medium of item 7, comprising L-tryptophan, L-proline and L-methionine each at the molar ratios according to item 7.
9. The basal cell culture medium of items 5, further comprising the following amino acids at a molar ratio relative to isoleucine (mM/mM) of:
   (a) L-lysine/L-isoleucine of about 1.8-2.7; and/or
   (b) L-tryptophan/L-isoleucine of about 0.3-0.5,
      L-proline/L-isoleucine of about 1.6-3.0; and
      L-methionine/L-isoleucine of about 0.4-0.7.
10. A basal cell culture medium for culturing mammalian cells comprising the following amino acids at a molar ratio relative to isoleucine (mM/mM) of:
    L-leucine/L-isoleucine of about 1.5-1.8,
    L-phenylalanine/L-isoleucine of about 0.6-0.8,
    L-tyrosine/L-isoleucine of about 1.9-2.3,
    L-threonine/I-isoleucine of about 1.3-1.6, and
    L-valine/L-isoleucine of about 1.3-1.6,
    wherein the basal cell culture medium has a total amino acid content of about 25 to 100 mM.
11. The basal cell culture medium of items 1, 5 or 10, further comprising L-lysine at a molar ratio relative to isoleucine of about 2.0-2.5 (mM/mM).
12. The basal cell culture medium of items 1, 2, 5, 6, 10 or 11, further comprising at least one of the following amino acids at a molar ratio relative to isoleucine (mM/mM) of:
    L-tryptophan/L-isoleucine of about 0.3-0.5,
    L-proline/L-isoleucine of about 1.6-3.0; or
    L-methionine/L-isoleucine of about 0.4-0.7.
13. The basal cell culture medium of item 12, comprising L-tryptophan, L-proline and L-methionine each at the molar ratios according to item 12.
14. The basal cell culture medium of item 10, further comprising the following amino acids at a molar ratio relative to isoleucine (mM/mM) of:
    (a) L-leucine/L-isoleucine of about 2.0-2.5, and/or
    (b) L-tryptophan/L-isoleucine of about 0.3-0.5,
       L-proline/L-isoleucine of about 1.6-3.0; and
       L-methionine/L-isoleucine of about 0.4-0.7.
15. The basal cell culture medium of any one of items 1 to 14, wherein the medium is a serum-free medium, preferably a chemically defined medium or a chemically defined and protein-free medium.
16. The basal cell culture medium of any one of items 1 to 15 additionally comprising iron choline citrate at a concentration of about 0.1 to 5.0 mM, about 0.2 to 2.0 mM, about 0.2 to 1.0 mM or about 0.4 to 1.0 mM.
17. The basal cell culture medium of any one of items 1 to 16, wherein the basal cell culture medium has a total amino acid content of about 30 to about 80, preferably about 35 to about 65, more preferably about 40 to about 50 mM.
18. A basal cell culture medium for culturing mammalian cells comprising iron choline citrate at a concentration of 0.1 to 5.0 mM, about 0.2 to 2.0 mM, about 0.2 to 1.0 mM or about 0.4 to 1.0 mM.
19. A feed medium for culturing mammalian cells comprising the following amino acids at a molar ratio relative to isoleucine (mM/mM) of:
    L-leucine/L-isoleucine of about 2.3-4.2,
    L-phenylalanine/L-isoleucine of about 0.6-1.1,
    L-threonine/I-isoleucine of about 1.3-2.4, and
    L-valine/L-isoleucine of about 1.1-2.0,
    wherein the feed medium has a total amino acid content of about 100 to 1000 mM.
20. The feed medium of item 19, further comprising the following amino acids at a molar ratio relative to isoleucine (mM/mM) of:
    L-tyrosine/L-isoleucine of about 0.6-1.1, and/or L-lysine/L-isoleucine of about 1.1-2.1, preferably L-tyrosine/L-isoleucine of about 0.6-1.1, and L-lysine/L-isoleucine of about 1.1-2.1.
21. The feed medium of items 19 or 20, further comprising at least one of the following amino acids at a molar ratio relative to isoleucine (mM/mM) of:
    L-tryptophan/L-isoleucine of about 0.3-0.6,
    L-proline/L-isoleucine of about 0.9-1.8; or
    L-methionine/L-isoleucine of about 0.4-0.8.
22. The feed medium of item 21, comprising L-tryptophan, L-proline and L-methionine each at the molar ratios according to item 21.
23. A feed medium for culturing mammalian cells comprising the following amino acids at a molar ratio relative to isoleucine (mM/mM) of:
    L-leucine/L-isoleucine of about 2.6-3.9,
    L-phenylalanine/L-isoleucine of about 0.7-1.0, L-threonine/I-isoleucine of about 1.5-2.2, and
L-valine/L-isoleucine of about 1.3-1.9,
wherein the feed medium has a total amino acid content of about 100 to 1000 mM.

24. The feed medium of items 19 or 23, further comprising the following amino acids at a molar ratio relative to isoleucine (mM/mM) of:
L-tyrosine/L-isoleucine of about 0.7-1.0, and/or L-lysine/L-isoleucine of about 1.3-1.9, preferably
L-tyrosine/L-isoleucine of about 0.7-1.0, and L-lysine/L-isoleucine of about 1.3-1.9.

25. The feed medium of items 19, 20, 23 or 24, further comprising at least one of the following amino acids at a molar ratio relative to isoleucine (mM/mM) of:
L-tryptophan/L-isoleucine of about 0.4-0.5,
L-proline/L-isoleucine of about 1.1-1.6; or
L-methionine/L-isoleucine of about 0.5-0.7.

26. The feed medium of item 25, comprising L-tryptophan, L-proline and L-methionine each at the molar ratios according to item 25.

27. The feed medium of item 23, further comprising the following amino acids at a molar ratio relative to isoleucine (mM/mM) of:
(a) L-tyrosine/L-isoleucine of about 0.7-1.0, and L-lysine/L-isoleucine of about 1.3-1.9, and/or
(b) L-tryptophan/L-isoleucine of about 0.4-0.5, L-proline/L-isoleucine of about 1.1-1.6; and L-methionine/L-isoleucine of about 0.5-0.7.

28. A feed medium for culturing mammalian cells comprising the following amino acids at a molar ratio relative to isoleucine (mM/mM) of:
L-leucine/L-isoleucine of about 2.9-3.5,
L-phenylalanine/L-isoleucine of about 0.8-0.9,
L-threonine/I-isoleucine of about 1.7-2.0, and
L-valine/L-isoleucine of about 1.4-1.7,
wherein the feed medium has a total amino acid content of about 100 to 1000 mM.

29. The feed medium of items 19, 23 or 28 further comprising the following amino acids at a molar ratio relative to isoleucine (mM/mM) of:
L-tyrosine/L-isoleucine of about 0.7-0.9, and/or L-lysine/L-isoleucine of about 1.4-1.8, preferably
L-tyrosine/L-isoleucine of about 0.7-0.9, and L-lysine/L-isoleucine of about 1.4-1.8.

30. The feed medium of items 19, 20, 23, 24, 28 or 29, further comprising at least one of the following amino acids at a molar ratio relative to isoleucine (mM/mM) of:
L-tryptophan/L-isoleucine of about 0.4-0.5,
L-proline/L-isoleucine of about 1.2-1.5; or
L-methionine/L-isoleucine of about 0.5-0.6.

31. The feed medium of item 30, comprising L-tryptophan, L-proline and L-methionine each at the molar ratios according to item 30.

32. The feed medium of item 28, further comprising at least one of the following amino acids at a molar ratio relative to isoleucine (mM/mM) of:
(a) L-tyrosine/L-isoleucine of about 0.7-0.9, and L-lysine/L-isoleucine of about 1.4-1.8 and/or.
(b) L-tryptophan/L-isoleucine of about 0.4-0.5, L-proline/L-isoleucine of about 1.2-1.5; and L-methionine/L-isoleucine of about 0.5-0.6.

33. The feed medium of any one of items 19 to 32, wherein the feed medium is a concentrated feed medium for addition to the cell culture at about 10-50 ml/L/day, preferably at about 15-45 ml/L/day, more preferably at about 20-40 ml/L/day and more preferably at about 30 ml/L/day based on the culture starting volume.

34. The feed medium of any one of items 19 to 32, wherein the medium is a serum-free medium, preferably a chemically defined medium or a chemically defined and protein-free medium.

35. The feed medium of any one of items 19 to 34 additionally comprising iron choline citrate at a concentration of about 0.4 to 5 mM, about 0.4 to 1.0 mM or about 0.5 to 1.0 mM, preferably about 0.5 to 0.6 mM.

36. The feed medium of any one of items 19 to 35 further characterized by that it has a low salt content, preferably about 100 mM or less, more preferably 50 mM or less.

37. The feed medium of any one of items 19 to 36, wherein the feed medium has a total amino acid content of about 200 to about 900, preferably about 300 to about 800, more preferably about 400 to about 700 mM 38. A feed medium for culturing cells comprising iron choline citrate at a concentration of about 0.4 to 5 mM, about 0.4 to 1.0 mM or about 0.5 to 1.0 mM, preferably about 0.5 to 0.6 mM.

39. A medium platform for culturing mammalian cells comprising:
a) the basal cell culture medium of items 1 to 18, and
b) the feed medium of items 19 to 38.

40. The cell culture medium of any one of items 1 to 18 or the feed medium of any one of items 19 to 38, wherein the mammalian cell is a rodent or human cell, wherein the rodent cell is preferably a Chinese hamster ovary (CHO) cell such as a CHO-K1 cell, a CHO-DG44 cell, a DuxB11 cell or a CHO GS deficient cell, most preferably the cell is a CHO-DG44 cell or a CHO GS deficient cell.

41. A method of generating a basal cell culture medium comprising:
a) providing a basal cell culture medium, and
b) adding amino acids at or adjusting the amino acid ratios to the final molar ratio according to items 1 to 17.

42. The method of item 41, further comprising a step of adding or adjusting as an iron source iron choline citrate at a concentration of about 0.1 to 5.0 mM, about 0.2 to 2.0 mM, about 0.2 to 1.0 mM, or about 0.4 to 1.0 mM.

43. A method of generating a feed medium comprising:
a) providing a feed medium, and
b) adding amino acids at or adjusting the amino acid ratios to the final molar ratio according to items 19 to 37.

44. The method of item 43, further comprising a step of adding or adjusting as an iron source iron choline citrate at a concentration of about 0.4 to 5 mM, about 0.4 to 1.0 mM or about 0.5 to 1.0 mM, preferably about 0.5 to 0.6 mM.

45. The method of any one of items 41 to 44, wherein the medium is a serum-free medium, preferably a chemically defined medium or a chemically defined and protein-free medium.

46. A method of culturing a mammalian cell comprising the following steps:
a) providing mammalian cells,
b) culturing the cells in the basal cell culture medium of any one of items 1 to 18, and
c) optionally adding the feed medium of any one of items 19 to 38 to the basal cell culture medium;

wherein the cells are cultured under conditions that allow the cells to proliferate.

47. A method of producing a protein of interest comprising the following steps:
   a) providing mammalian cells comprising a gene of interest encoding the protein of interest,
   b) culturing the cells in the basal cell culture medium of any one of items 1 to 18, and
   c) optionally adding the feed medium of any one of items 19 to 38 to the basal cell culture medium, and
   d) optionally separating and/or isolating and/or purifying said protein of interest from the cell culture;
   wherein the cells are cultured under conditions that allow expression of the protein of interest.

48. The method of item 47, wherein the protein of interest is a secreted protein, preferably the protein of interest is an antibody or Fc-fusion protein.

49. The method of any one of items 46 to 48, wherein the mammalian cell is a rodent or human cell, preferably the rodent cell is a Chinese hamster ovary (CHO) cell such as a CHO-K1 cell, a CHO-DG44 cell, a DuxB11 cell or a CHO GS deficient cell, most preferably the cell is a CHO-DG44 cell or a CHO GS deficient cell.

50. The method of any one of items 46 to 49, wherein the feed medium of any one of items 19 to 38 is added to the cells cultured in the basal cell culture medium and wherein
   (a) the feed medium is added at about 10-50 ml/L/day, preferably at about 15-45 ml/L/day, more preferably at about 20-40 ml/L/day and more preferably at about 30 ml/L/day based on the culture starting volume to the basal cell culture medium,
   (b) the feed medium is added starting on day 0, 1, 2 or 3, and/or
   (c) the feed medium is added continuously or as a bolus several times a day, two times a day, once per day, every second day or every third day.

51. The method of any one of items 46 to 50, wherein the cell culture is a large-scale cell culture, preferably a cell culture of a working volume of 100 L or more, more preferably of 1000 L or more or even more preferably of 10000 L or more.

52. A kit of parts comprising the basal cell culture medium of any one of items 1 to 18 and/or the feed medium of any one of items 19 to 39, and optionally a mammalian cell.

53. Use of the basal cell culture medium of any one of items 1 to 18 for producing a protein comprising culturing mammalian cells that produce a protein of interest in said medium for a period of time and conditions suitable for cell growth and protein production, harvesting the protein of interest and recovering the protein from the culture medium or cell lysate.

4. The use of item 53, further comprising feeding the cells with the feed medium of any one of items 19 to 38 during said culture period.

55. Use of the feed medium of any one of items 19 to 39 for producing a protein comprising culturing mammalian cells that produce the protein of interest in the basal cell culture medium of any one of items 1 to 18 for a period of time and conditions suitable for cell growth and protein production, feeding the cells with said feed medium, harvesting the protein of interest and recovering the protein from the culture medium.

56. Use of iron choline citrate as iron carrier in a mammalian cell culture medium, wherein the iron choline citrate is present in the mammalian cell culture medium at a concentration of about 0.2 to 2.0 mM.

The invention claimed is:

1. A medium platform for culturing mammalian cells comprising:
   a) a basal cell culture medium for culturing mammalian cells comprising the following amino acids at a molar ratio relative to isoleucine (mM/mM) of:
   L-leucine/L-isoleucine of 1.2-2.2,
   L-phenylalanine/L-isoleucine of 0.5-0.9,
   L-tyrosine/L-isoleucine of 1.5-2.7,
   L-threonine/l-isoleucine of 1.0-1.9, and
   L-valine/L-isoleucine of 1.0-1.9,
   wherein the basal cell culture medium has a total amino acid content of 25 to 150 mM, and
   b) a feed medium comprising the following amino acids at a molar ratio relative to isoleucine (mM/mM) of:
   L-leucine/L-isoleucine of 2.3-4.2,
   L-phenylalanine/L-isoleucine of 0.6-1.1,
   L-threonine/l-isoleucine of 1.3-2.4, and
   L-valine/L-isoleucine of 1.1-2.0,
   wherein the feed medium has a total amino acid content of 100 to 1000 mM.

2. The medium platform of claim 1, wherein the basal cell culture medium further comprises L-lysine at a molar ratio relative to isoleucine of 1.6-2.9 (mM/mM).

3. The medium platform of claim 1, wherein the basal cell culture medium further comprises at least one of the following amino acids at a molar ratio relative to isoleucine (mM/mM) of:
L-tryptophan/L-isoleucine of 0.3-0.5,
L-proline/L-isoleucine of 1.6-3.0; or
L-methionine/L-isoleucine of 0.4-0.7.

4. The medium platform of claim 1, wherein the basal cell culture medium further comprises iron choline citrate at a concentration of 0.1 to 5.0 mM, 0.2 to 2.0 mM, 0.2 to 1.0 mM or 0.4 to 1.0 mM.

5. The medium platform of claim 1, wherein the feed medium further comprises the following amino acids at a molar ratio relative to isoleucine (mM/mM) of:
L-tyrosine/L-isoleucine of 0.6-1.1, or L-lysine/L-isoleucine of 1.1-2.1, or
L-tyrosine/L-isoleucine of 0.6-1.1, and L-lysine/L-isoleucine of 1.1-2.1.

6. The medium platform of claim 1, wherein the feed medium further comprises at least one of the following amino acids at a molar ratio relative to isoleucine (mM/mM) of:
L-tryptophan/L-isoleucine of 0.3-0.6,
L-proline/L-isoleucine of 0.9-1.8; or
L-methionine/L-isoleucine of 0.4-0.8.

7. The medium platform of claim 1, wherein the feed medium additionally comprises iron choline citrate at a concentration of 0.4 to 5 mM, 0.4 to 1.0 mM or 0.5 to 1.0 mM, or 0.5 to 0.6 mM.

* * * * *

SEQUENCE LISTING

```
<160> NUMBER OF SEQ ID NOS: 5

<210> SEQ ID NO 1
<211> LENGTH: 451
<212> TYPE: PRT
<213> ORGANISM: Artificial Sequence
<220> FEATURE:
<223> OTHER INFORMATION: Rituximab HC

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Rituximab LC

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30
```

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 3
<211> LENGTH: 450
<212> TYPE: PRT
<213> ORGANISM: Artificial Sequence
<220> FEATURE:
<223> OTHER INFORMATION: mAb6 HC

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

-continued

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 4
<211> LENGTH: 214
<212> TYPE: PRT
<213> ORGANISM: Artificial Sequence
<220> FEATURE:
<223> OTHER INFORMATION: mAb6 LC

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 5
<211> LENGTH: 383
<212> TYPE: PRT
<213> ORGANISM: Artificial Sequence
<220> FEATURE:
<223> OTHER INFORMATION: Fc-fusion protein

<400> SEQUENCE: 5

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
            35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
            115                 120                 125

Tyr Leu Gly Ile Gly Asn Gly Thr Gln Ile Tyr Val Ile Asp Pro Glu
            130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
            210                 215                 220
```

```
Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
                260                 265                 270

Ser Lys Ala Lys Gly Gln Pro Arg Glu Pro Gln Val Tyr Thr Leu Pro
            275                 280                 285

Pro Ser Arg Asp Glu Leu Thr Lys Asn Gln Val Ser Leu Thr Cys Leu
        290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
        370                 375                 380
```